US008092991B2

(12) United States Patent
Schatz et al.

(10) Patent No.: US 8,092,991 B2
(45) Date of Patent: Jan. 10, 2012

(54) DE NOVO ENZYMATIC PRODUCTION OF NUCLEIC ACID MOLECULES

(75) Inventors: Octavian Schatz, Altomunster (DE);
Timothy O'Connell, Dusseldorf (DE);
Gudrun Horn, Munich (DE); Heinz Schwer, Buchloe (DE)

(73) Assignee: Cloning Biotechnology GmbH, Martinsreid (DE)

( * ) Notice: Subject to any disclaimer, the term of this patent is extended or adjusted under 35 U.S.C. 154(b) by 507 days.

(21) Appl. No.: 10/587,090

(22) PCT Filed: Jan. 22, 2005

(86) PCT No.: PCT/EP2005/000620
§ 371 (c)(1),
(2), (4) Date: Oct. 14, 2007

(87) PCT Pub. No.: WO2005/071077
PCT Pub. Date: Aug. 4, 2005

(65) Prior Publication Data
US 2009/0298133 A1 Dec. 3, 2009

(30) Foreign Application Priority Data
Jan. 23, 2004 (EP) .................................. 04001462

(51) Int. Cl.
*C12Q 1/68* (2006.01)
*C07H 21/02* (2006.01)
(52) U.S. Cl. .......................................... 435/6; 536/22.1
(58) Field of Classification Search ............. 435/6, 91.2; 536/24.31, 24.32, 24.33
See application file for complete search history.

(56) References Cited

U.S. PATENT DOCUMENTS

| 5,397,698 A | 3/1995 | Goodman et al. |
| 5,508,169 A | 4/1996 | Deugau et al. |
| 5,710,000 A | 1/1998 | Sapolsky et al. |
| 5,770,365 A | 6/1998 | Lane et al. |
| 5,858,656 A | 1/1999 | Deugau et al. |
| 5,888,737 A | 3/1999 | DuBridge et al. |
| 5,981,190 A | 11/1999 | Israel |
| 6,485,944 B1 | 11/2002 | Church et al. |
| 2006/0115850 A1* | 6/2006 | Schatz ............................. 435/6 |
| 2006/0194202 A1* | 8/2006 | Schatz et al. ..................... 435/6 |
| 2008/0044862 A1 | 2/2008 | Schatz et al. |

FOREIGN PATENT DOCUMENTS

| EP | 0245130 | 11/1987 |
| EP | 1 411 122 | 4/2004 |
| EP | 1 411 122 A1 * | 4/2004 |
| WO | WO93/19202 | 9/1993 |
| WO | WO95/17413 | 6/1995 |
| WO | WO96/12014 | 4/1996 |
| WO | WO98/10095 | 12/1998 |
| WO | WO 99/47536 | 9/1999 |
| WO | WO99/47536 | 9/1999 |
| WO | WO 00/75368 | 12/2000 |
| WO | WO 00/75368 A1 * | 12/2000 |
| WO | WO01/61036 | 8/2001 |
| WO | WO 0161036 A2 * | 8/2001 |
| WO | WO01/75180 | 10/2001 |
| WO | WO 03/044193 | 5/2003 |
| WO | EP1411122 | 4/2004 |
| WO | WO 2004/035781 | 4/2004 |

OTHER PUBLICATIONS

Bolli, et al.; *Pyranosyl-RNA:chiroselective self-assembly of base sequences by ligative oligomerization of tetranucleotide-2 ', 3 '-cyclophosphates*, 1997, Chem. Biol. 4(4): 309-320.
Hoare & Koshland; *A method for the quantitative modification and estimation of carboxylic acid groups in proteins*, 1967, J. Biol. Chem. 242(10): 2447-2453.
Sekiya, et al.; *Total Synthesis of a tyrosine suppressor tRNA gene. XV. Synthesis of the promoter region*, 1979, J. Biol. Chem. 254(13): 5781-5786.
Sekiya, et al.; *Total synthesis of a tyrosine suppressor transfer RNA gene. XVI. Enzymatic joinings to form the total 207-base pair-long DNA*, 1979, J. Biol. Chem. 254(13): 5787-5801.
Xiong et al: "Non-polymerase-cycling-assembly-based chemical gene synthesis: Strategies, methods, and progress", Biotechnology Advances, Elsevier Publishing, Barking, GB, vol. 26, No. 2, Nov. 7, 2007, pp. 121-134, XP022426820.
Eugen Uhlmann: "An alternative approach in gene synthesis: use of long selfpriming oligodeoxynucleotides for the construction of double-stranded DNA", Gene, vol. 71, Nov. 15, 1988, pp. 29-40, XP000941756.
Wlodek Mandecki et al.: "A totally synthetic plasmid for general cloning, gene expression and mutagenesis in *Escherichia coli*", Gene, vol. 94, Sep. 28, 1990, pp. 103-107, XP000941757.
Van Den Brulle, et al.: "A novel solid phase technology for high-throughput gene synthesis", Biotechniques vol. 45, No. 3, 2008, pp. 340-343.
Padgett KA et al: I"Creating seamless junctions independent of restriction site in PCR cloning", Gene, Elsevier Biomedical Press. Amsterdam, NL, vol. 168, No. 1, Feb. 2, 1996, pp. 31-35, XP004042930.
Kato K: "Description of the entire mRNA population by A3' end cDNA fragment generated by class IIS restriction enzymes", Nucleic Acids Research, Oxford University, Press, Surrey, GB, vol. 23, No. 18, Sep. 1, 1995, pp. 3685-3690, XP002008304.

(Continued)

*Primary Examiner* — Prabha Chunduru

(57) ABSTRACT

The present invention relates to methods for making a nucleic acid molecule and methods for ligating oligonucleotides. The method includes ligating a first at least partially double-stranded oligonucleotide that has a first and second single-stranded overhang to a second at least partially double-stranded oligonucleotide that has a recognition site for a type IIS restriction enzyme, a modification allowing the oligonucleotide to be coupled to a surface, and a single-stranded overhang. The ligation product can be cleaved with a type IIS restriction enzyme, thereby releasing an elongated fragment having two single-stranded overhangs. These steps can be repeated by using the elongated fragment in a subsequent ligation to another at least partially double-stranded oligonucleotide that has a type IIS restriction enzyme recognition site.

13 Claims, 20 Drawing Sheets

OTHER PUBLICATIONS

Shibata Y et al: Cloning full-length, Cap-Trapper-selected cDNAs by using the single-strand linker ligation method. II, Biotechniques, vol. 30, No. 6, Jun. 2001, pp. 1250-1254, XP002197302.

Unrau Paul et al: "Non-cloning amplification of specific DNA fragments from whole genomic DNA digests using DNA, indexers'", Gene, Elsevier Biomedical Press. Amsterdam, NL, vol. 145, No. 2, 1994, pp. 163-169, XP002149819.

Velculescu VE et al: "Serial Analysis of Gene Expression" Science, American Association for the Advancement of Science US, vol. 270, No. 5235, Oct. 20, 1995, pp. 484-487, XP001024449.

Shao-Chi Huang et al., "Binding of biotinylated DNA to Streptavidin-Coated Polystryrene Latex." 222 Analytical Biochemistry (1994) 441-449.

Roberts, R.J. and D. Macelis (1999) REBASE-restriction enzymes and methylases. Nucleic Acids Res 27:312-3.

* cited by examiner

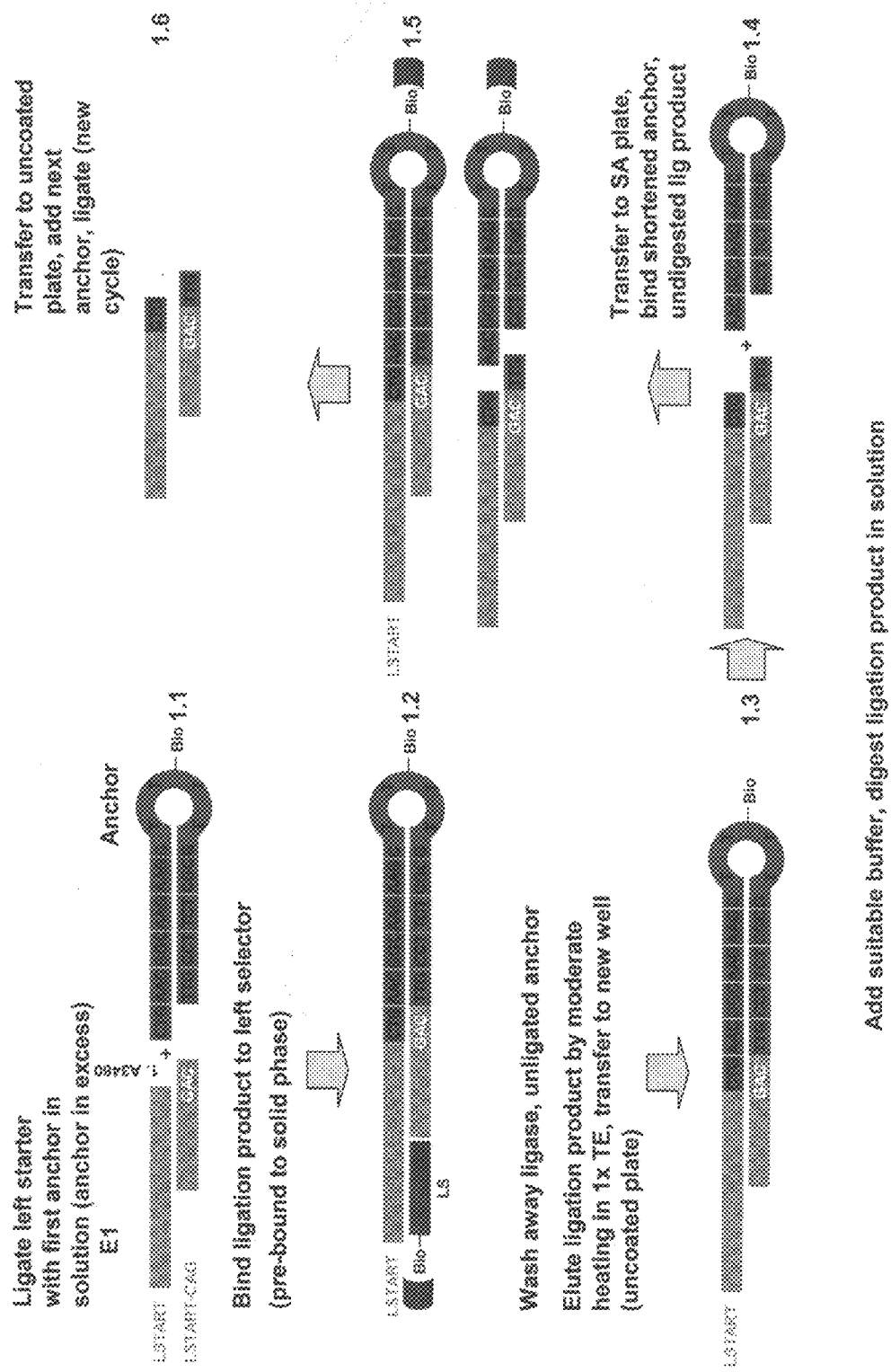

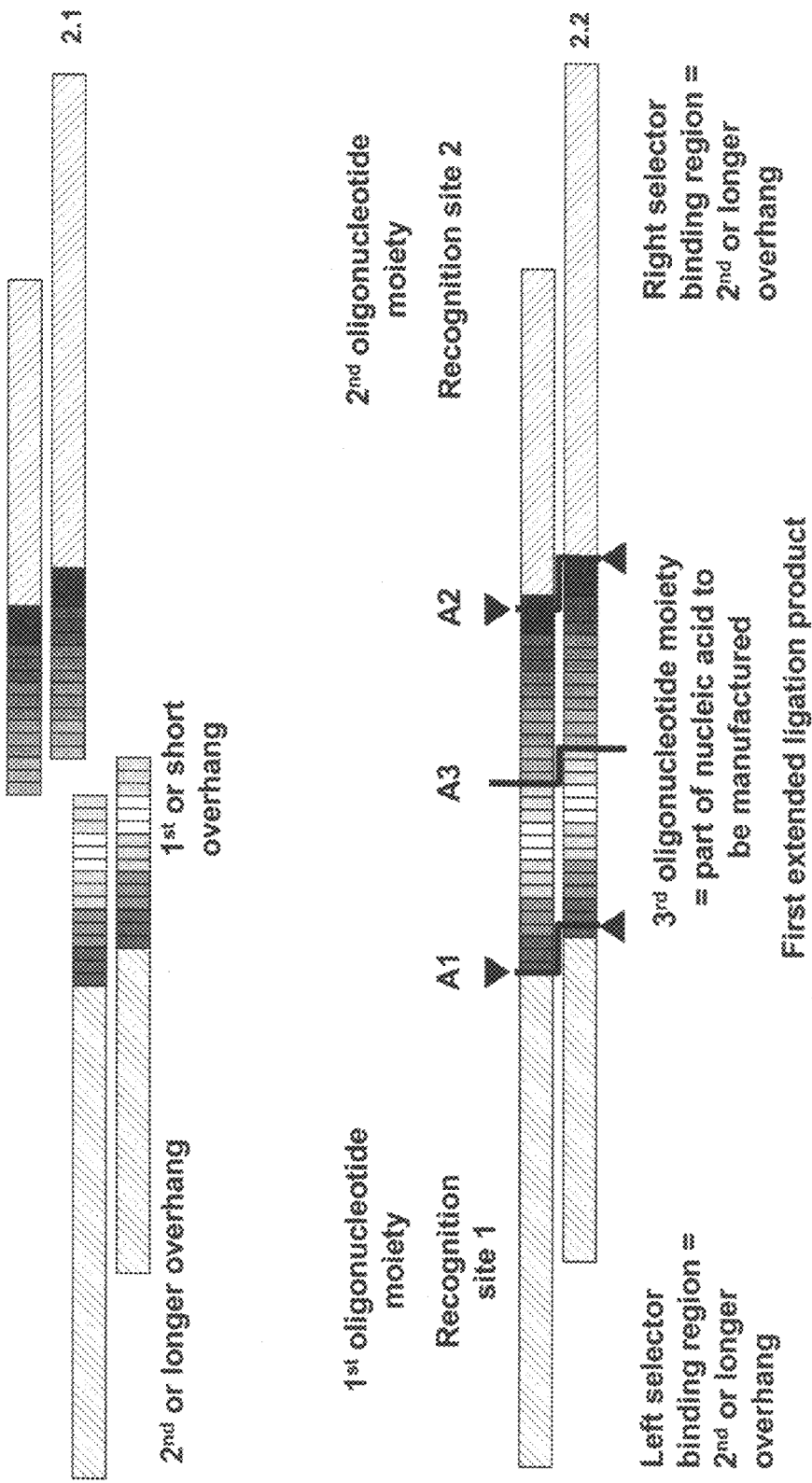
Fig. 2 – Structure of a double-selectable first order transposition product and its elongation block precursors

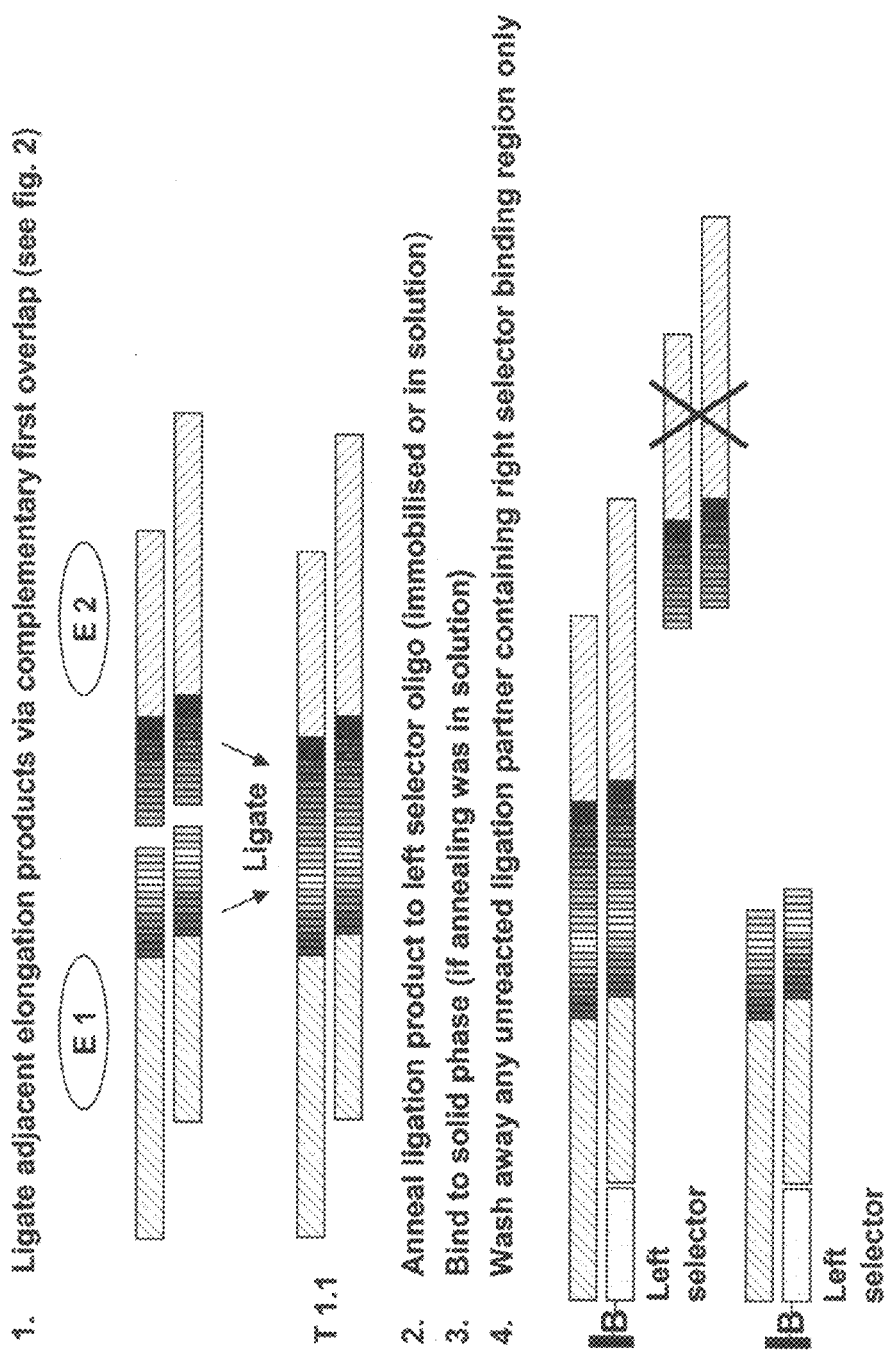

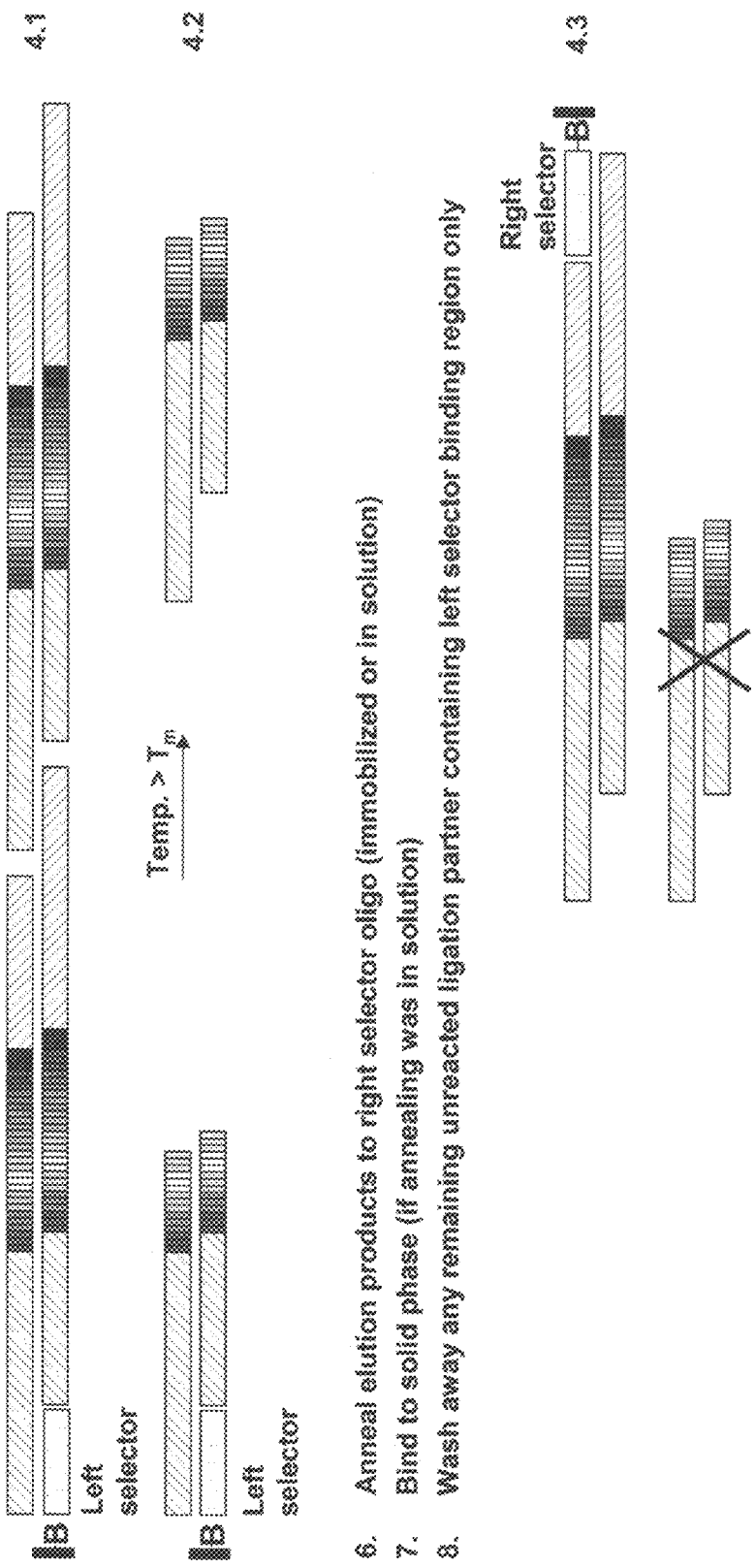

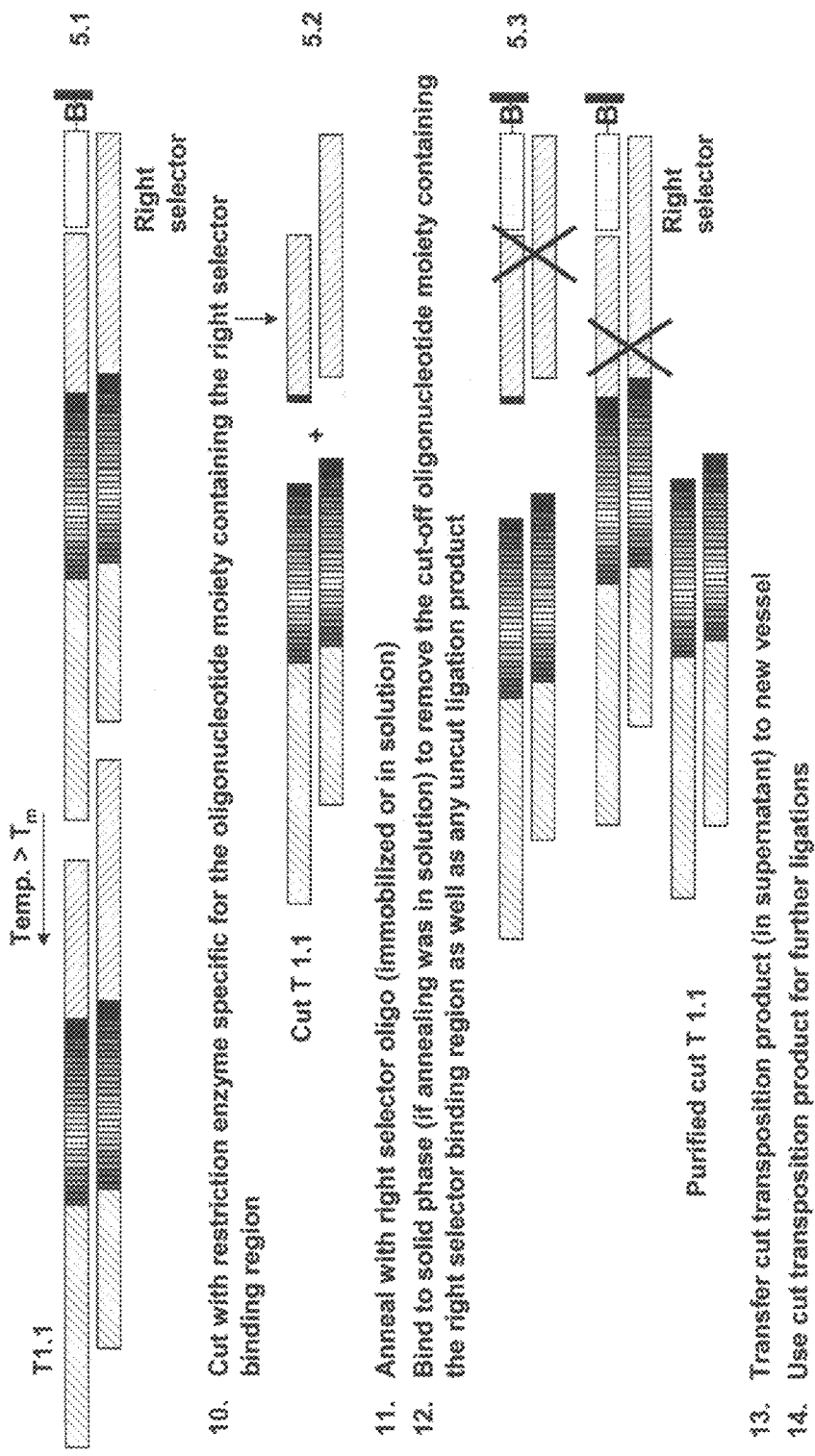

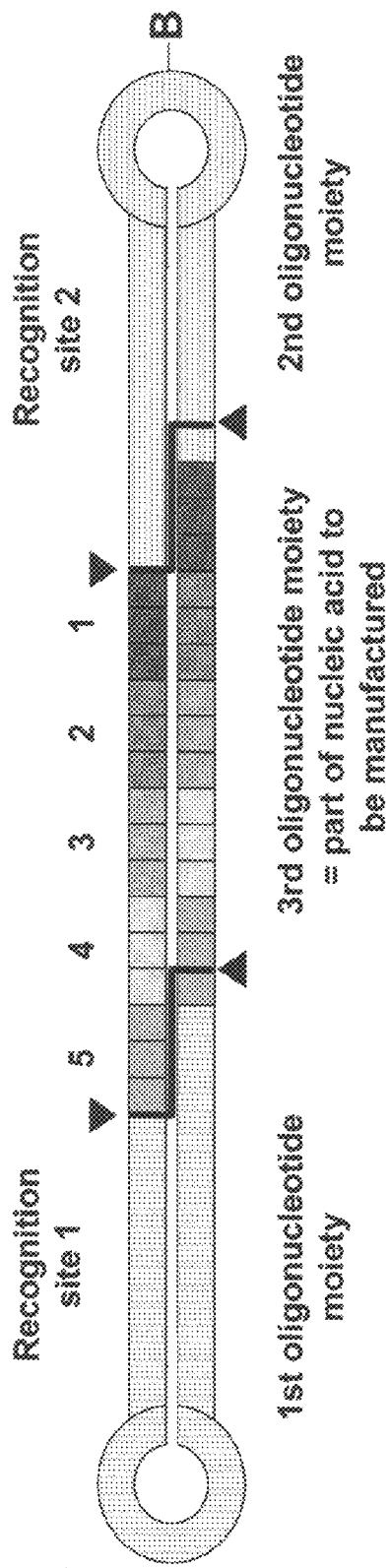

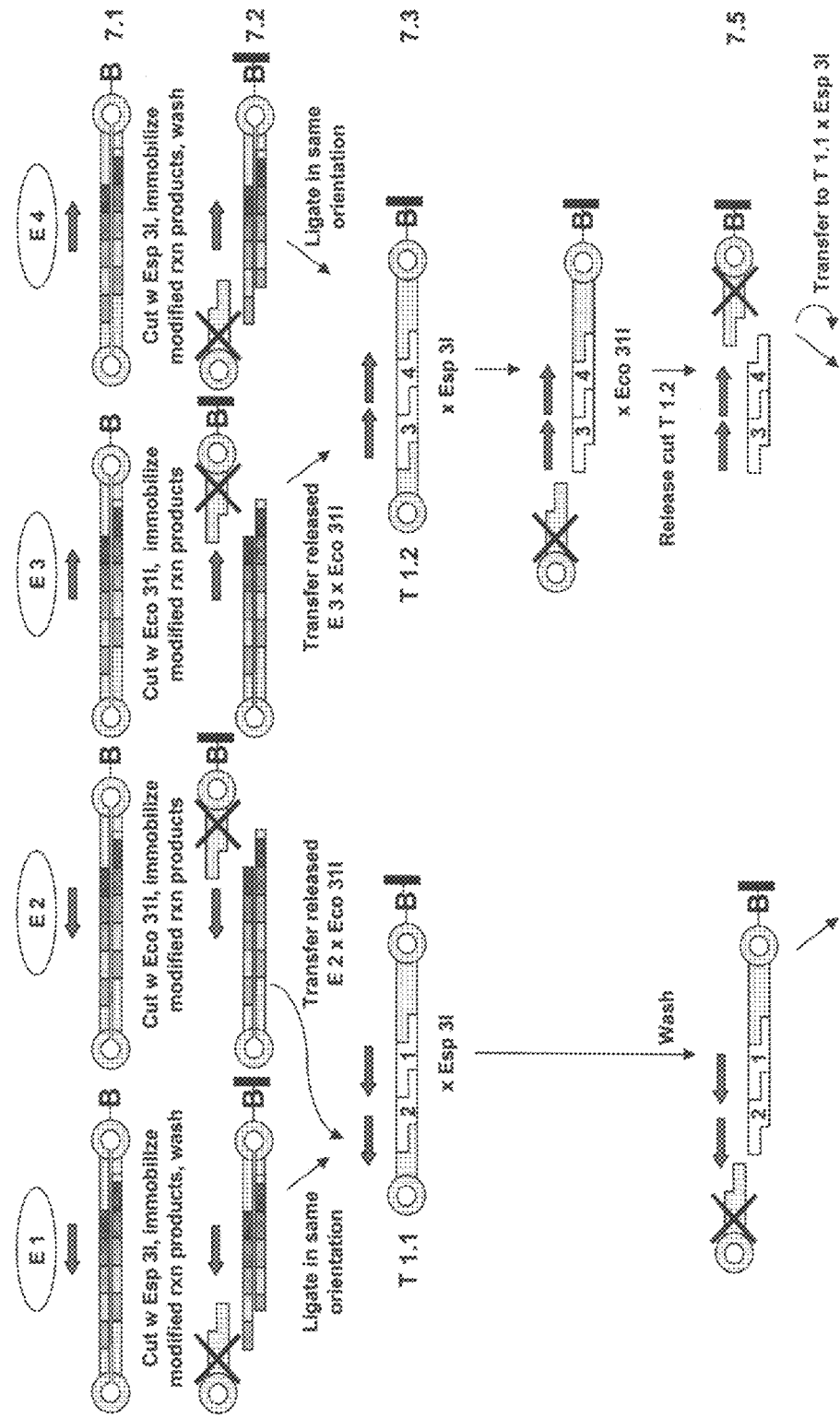

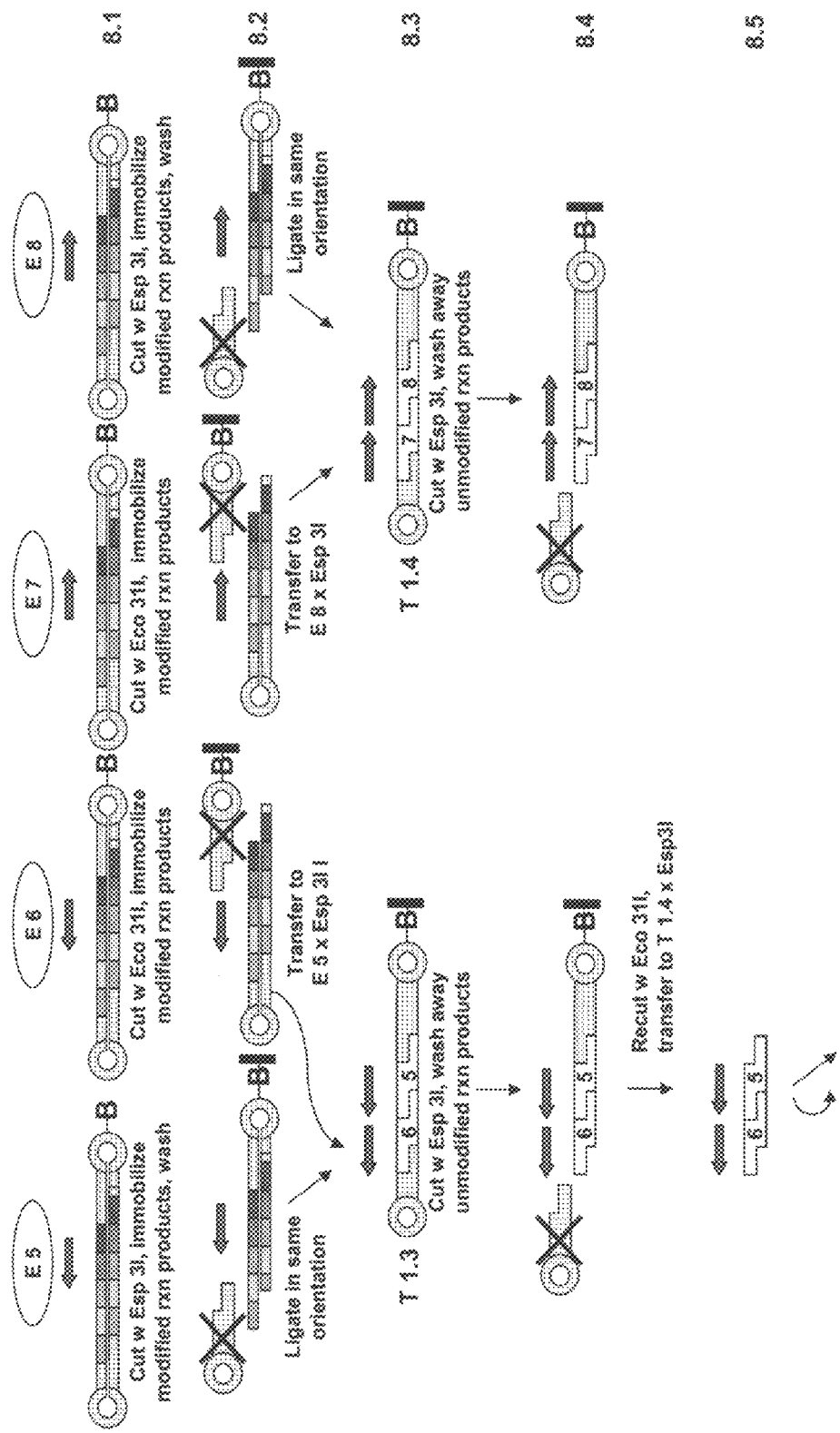
Fig. 8 – S-HIT procedure (Esp-Eco)

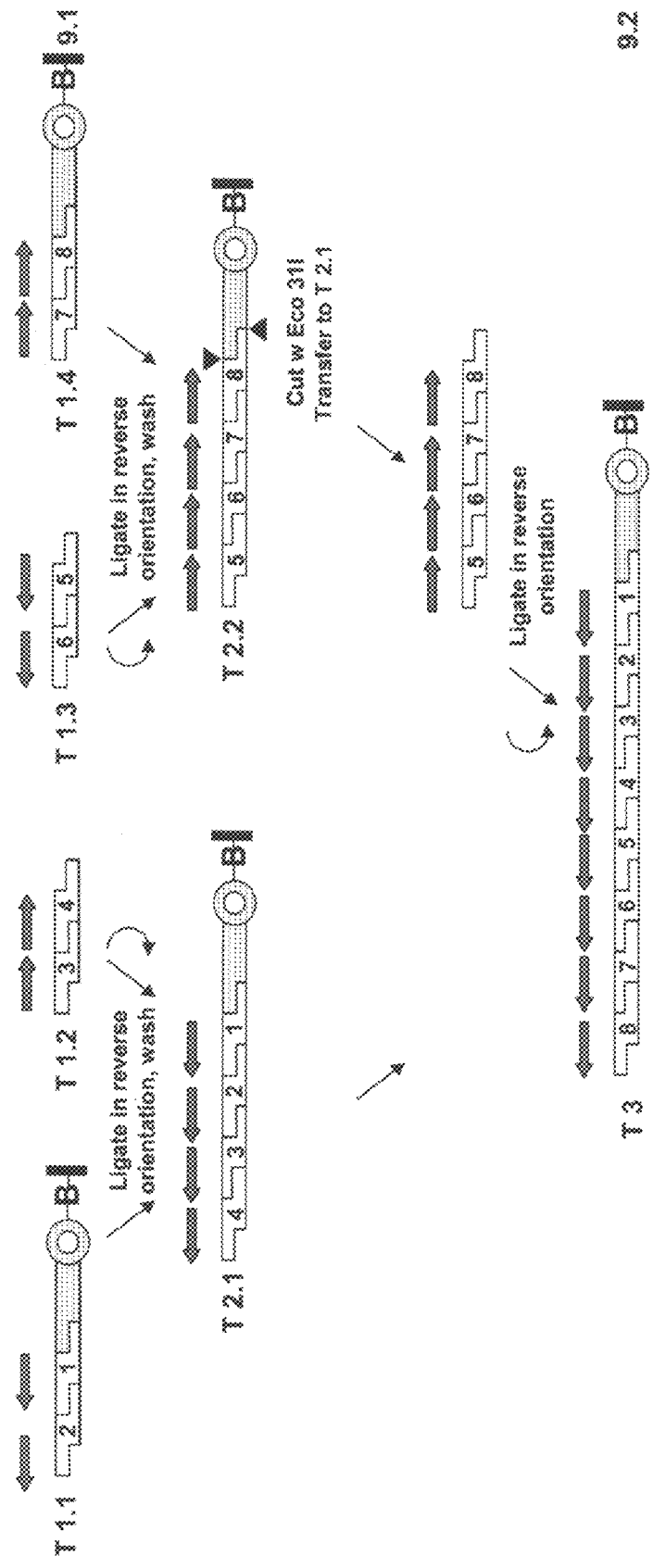

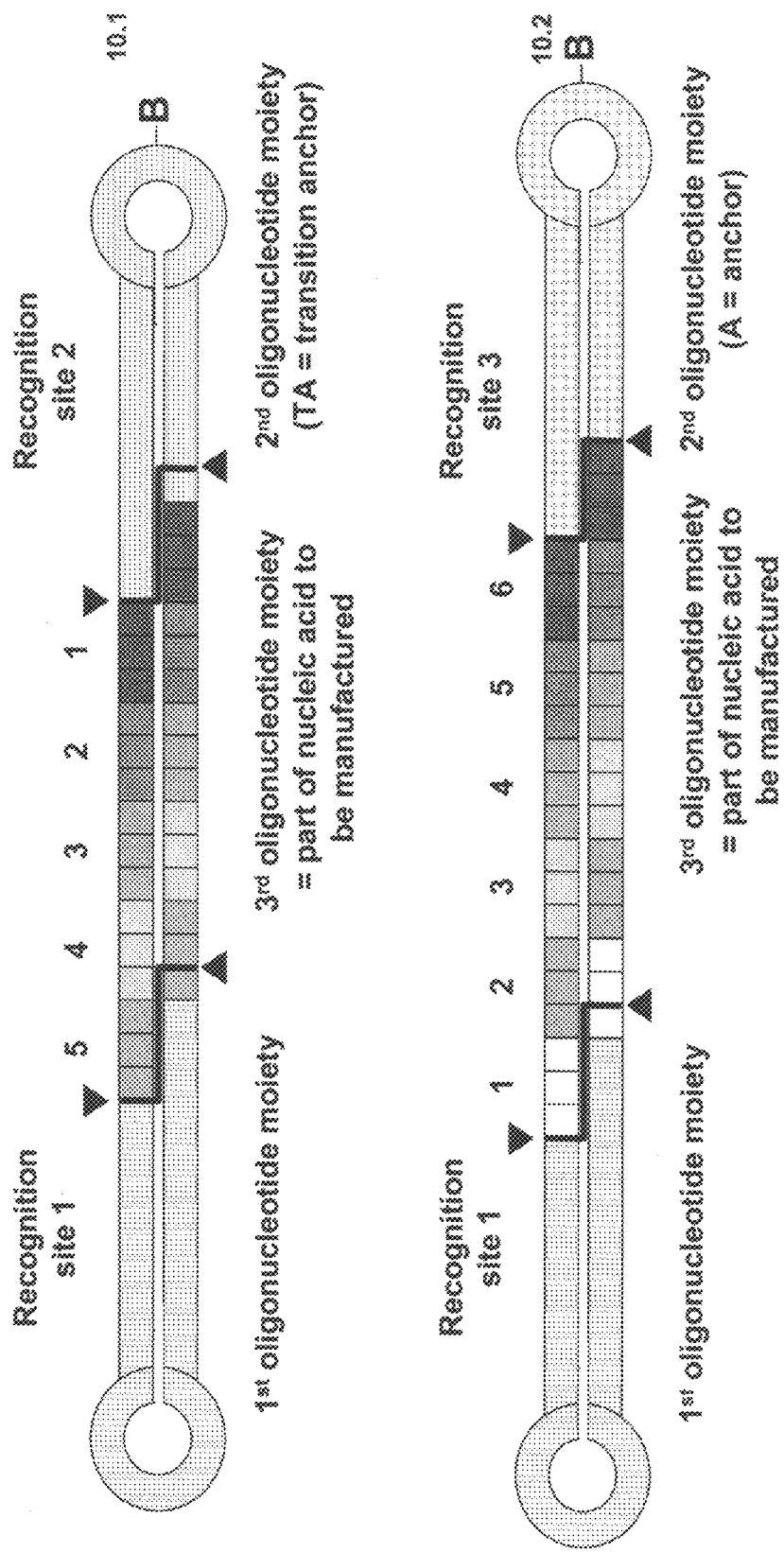

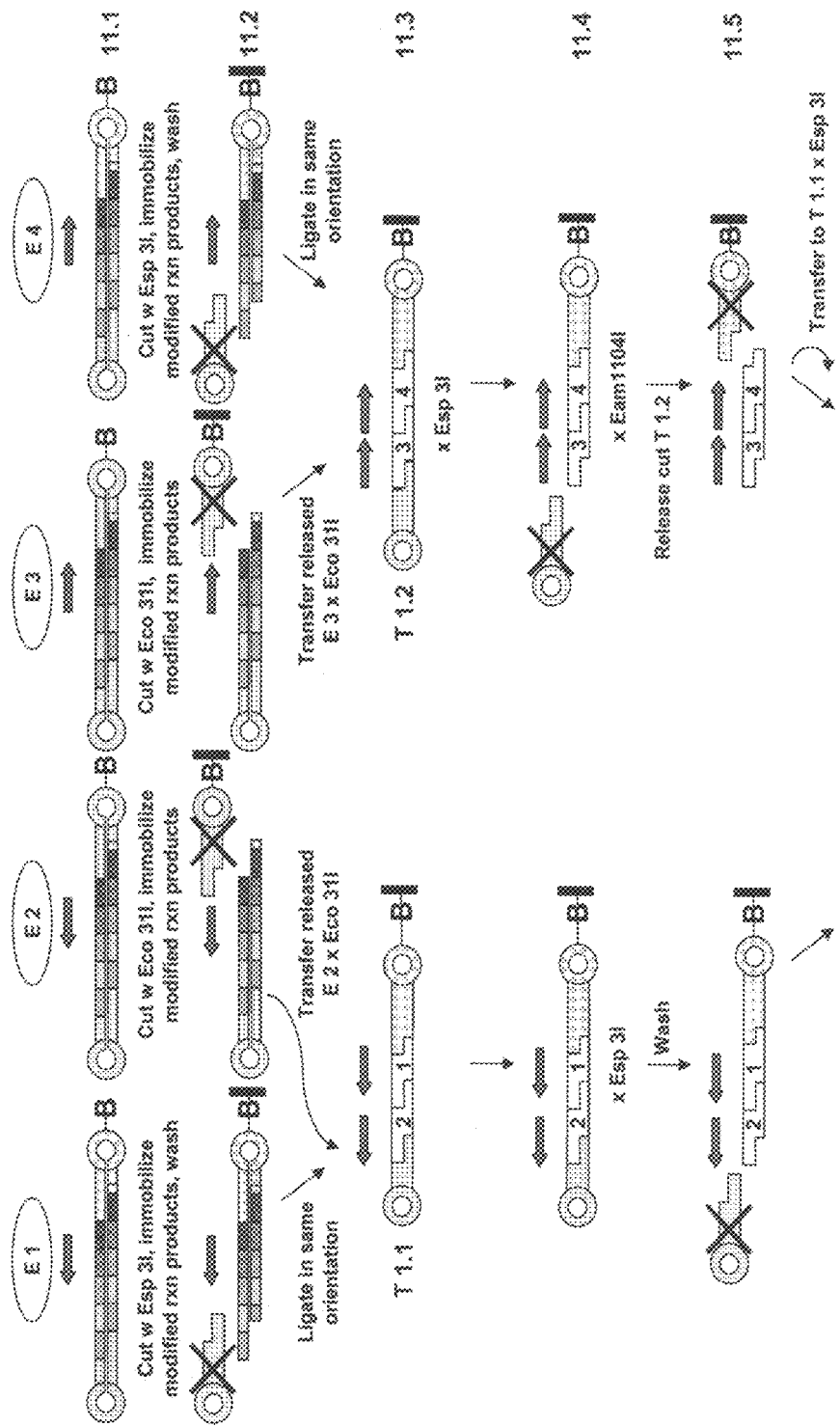
Fig. 11 – S-HIT procedure (Esp-Eam)
Elongation blocks E1 – E4 (arrows = orientation in target sequence)

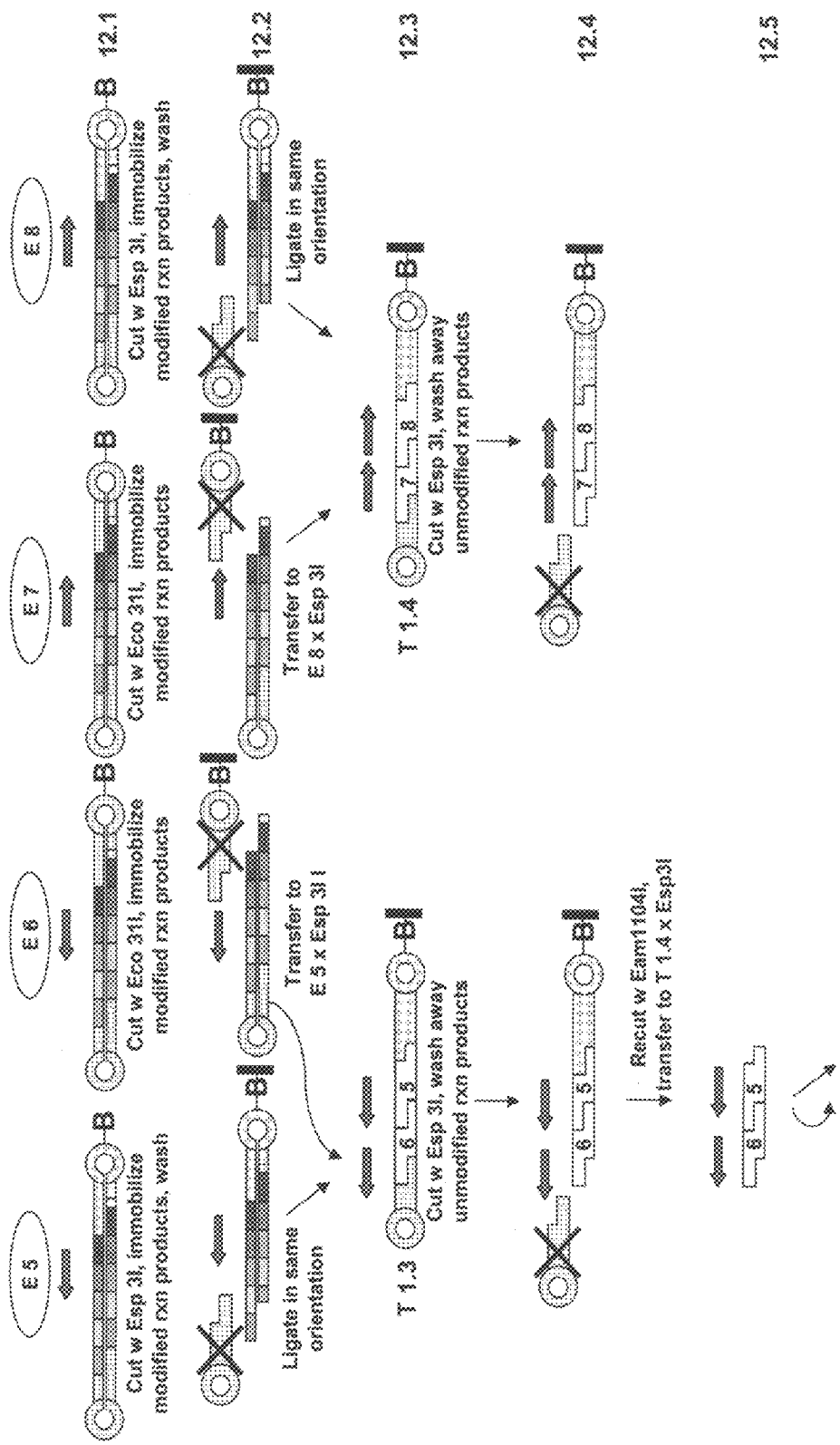

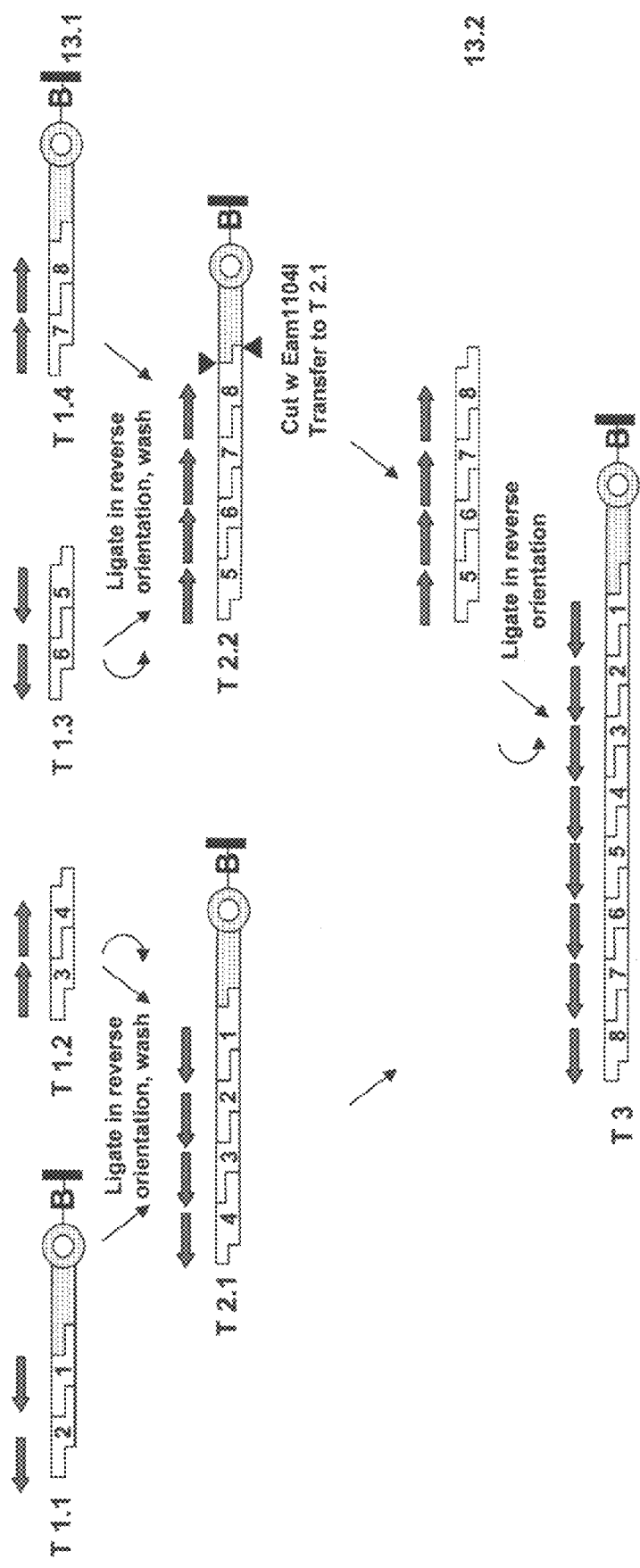
Fig. 13 – S-HIT procedure (Esp-Eam)

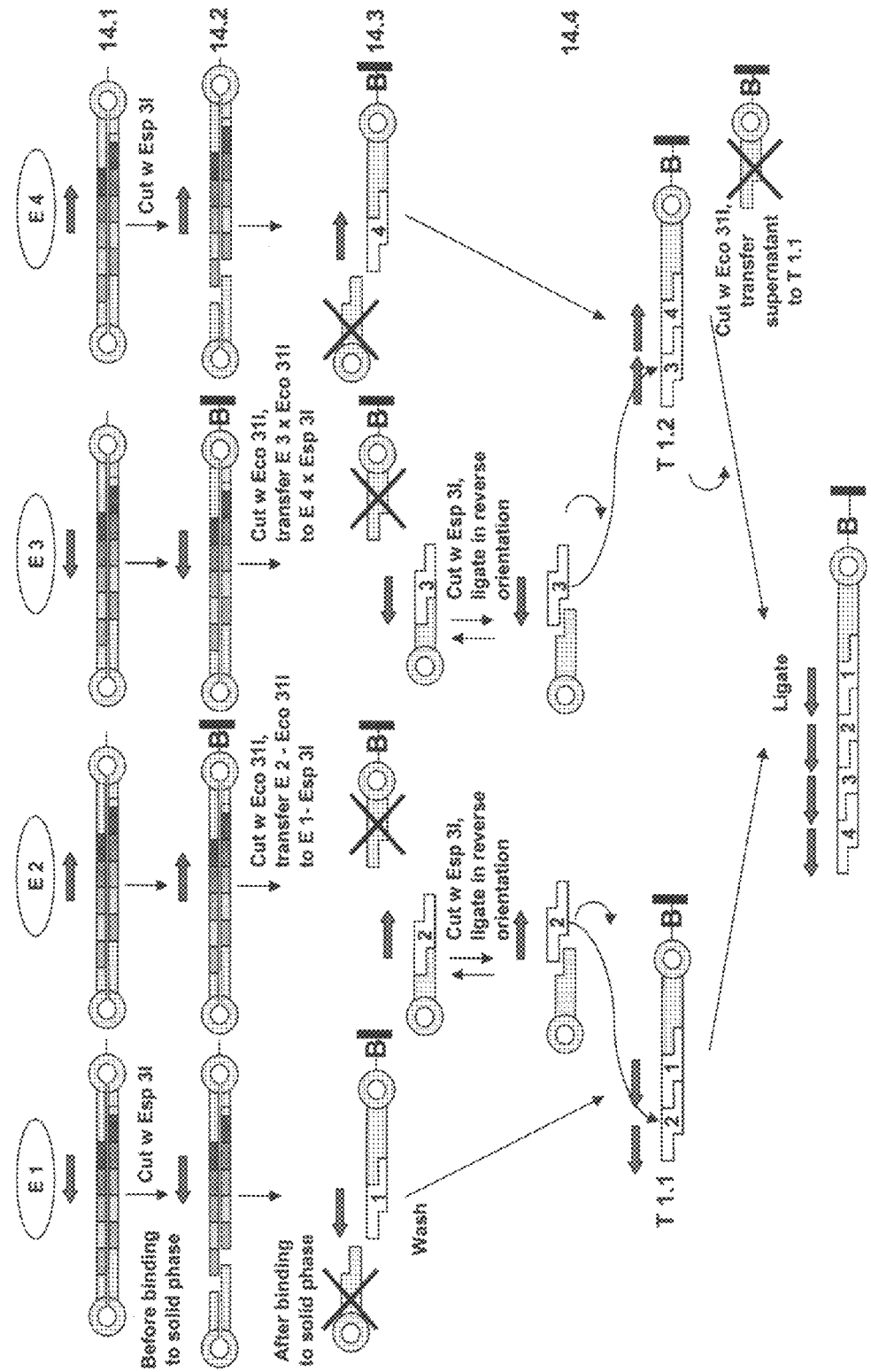
Fig. 14 – ASIT (Esp-Eco)

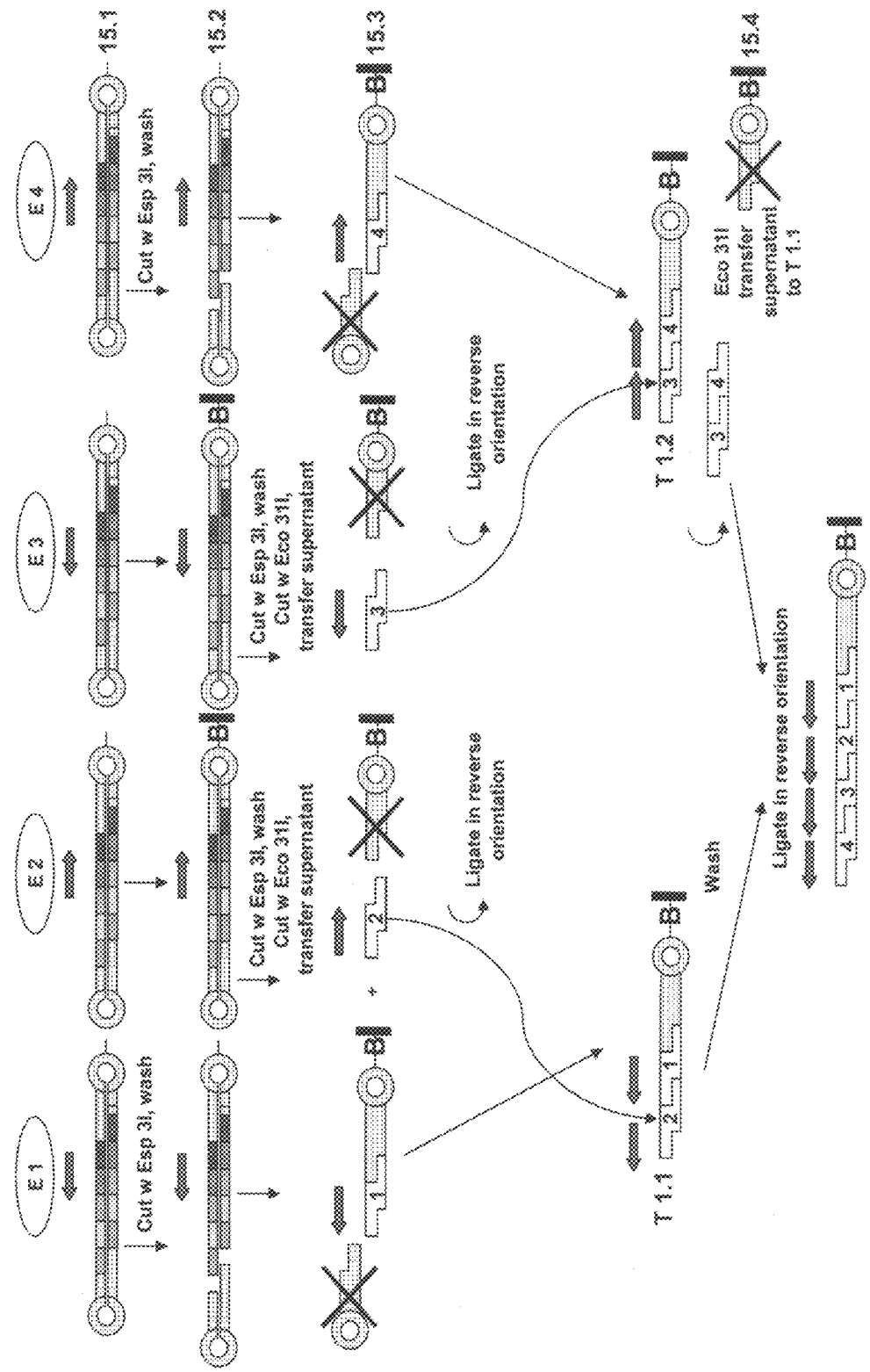

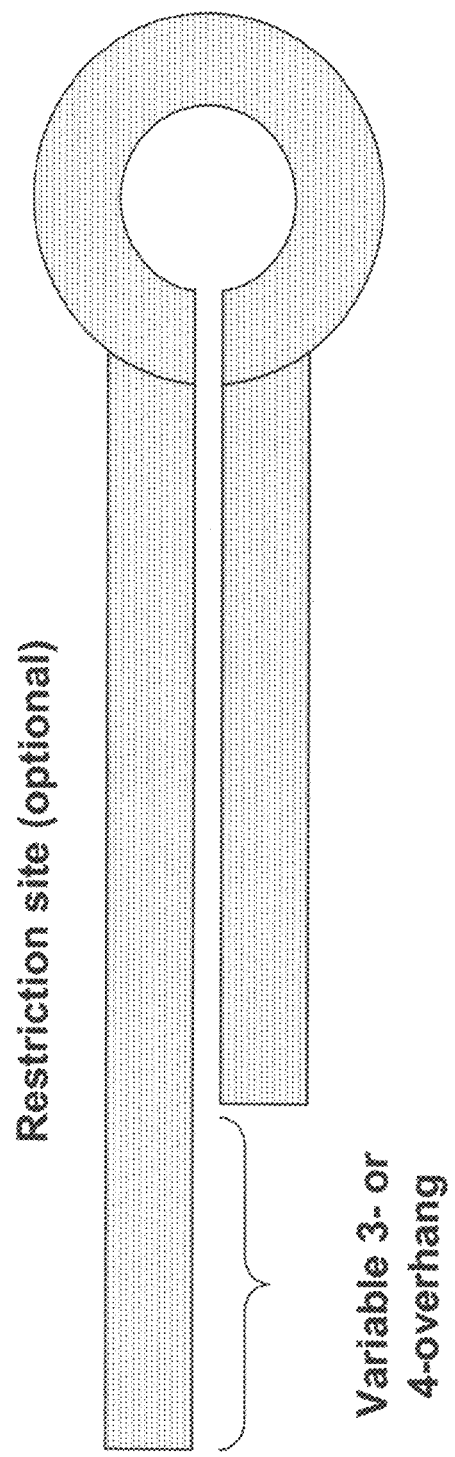
Fig. 16 – Capping oligonucleotide

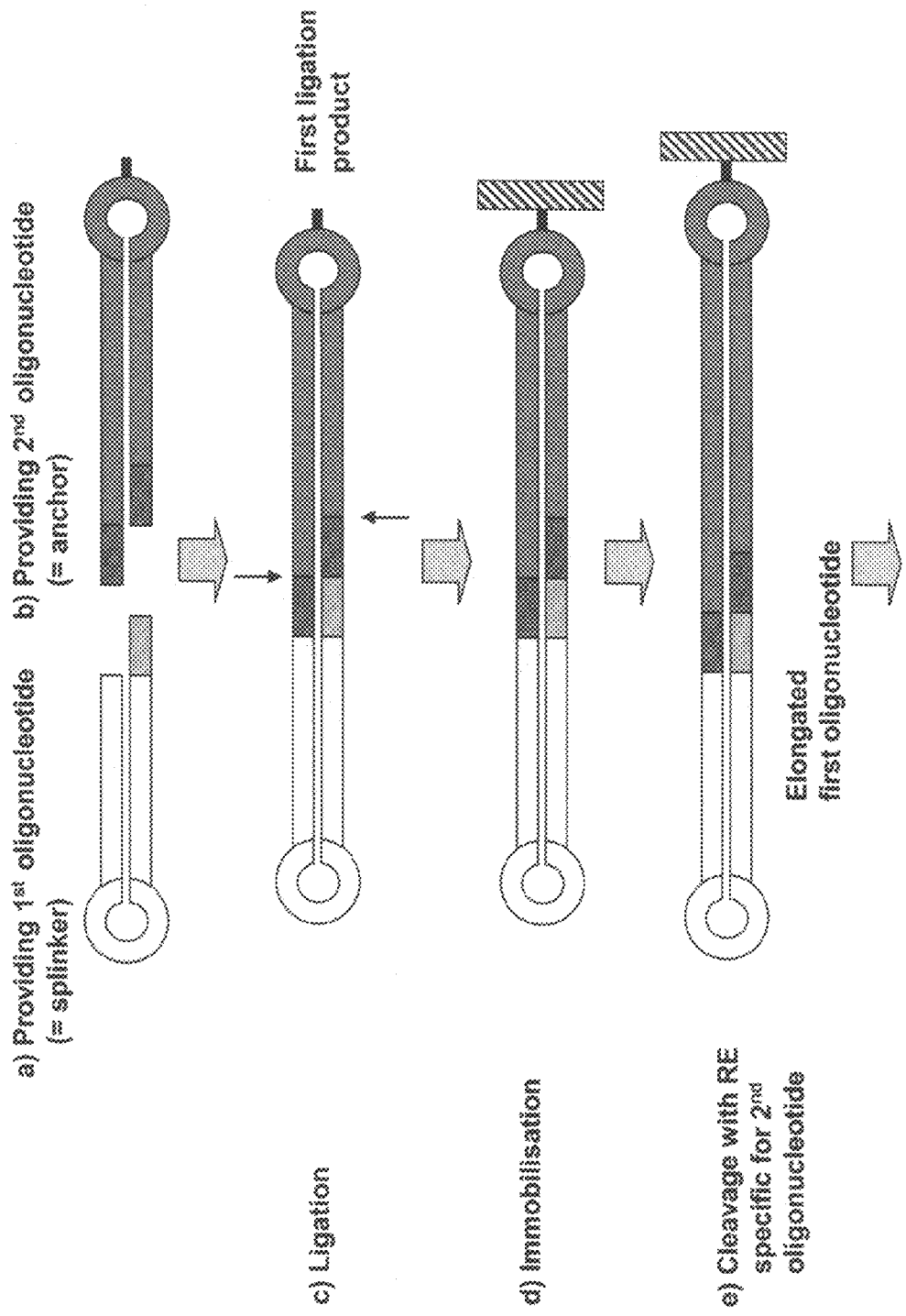

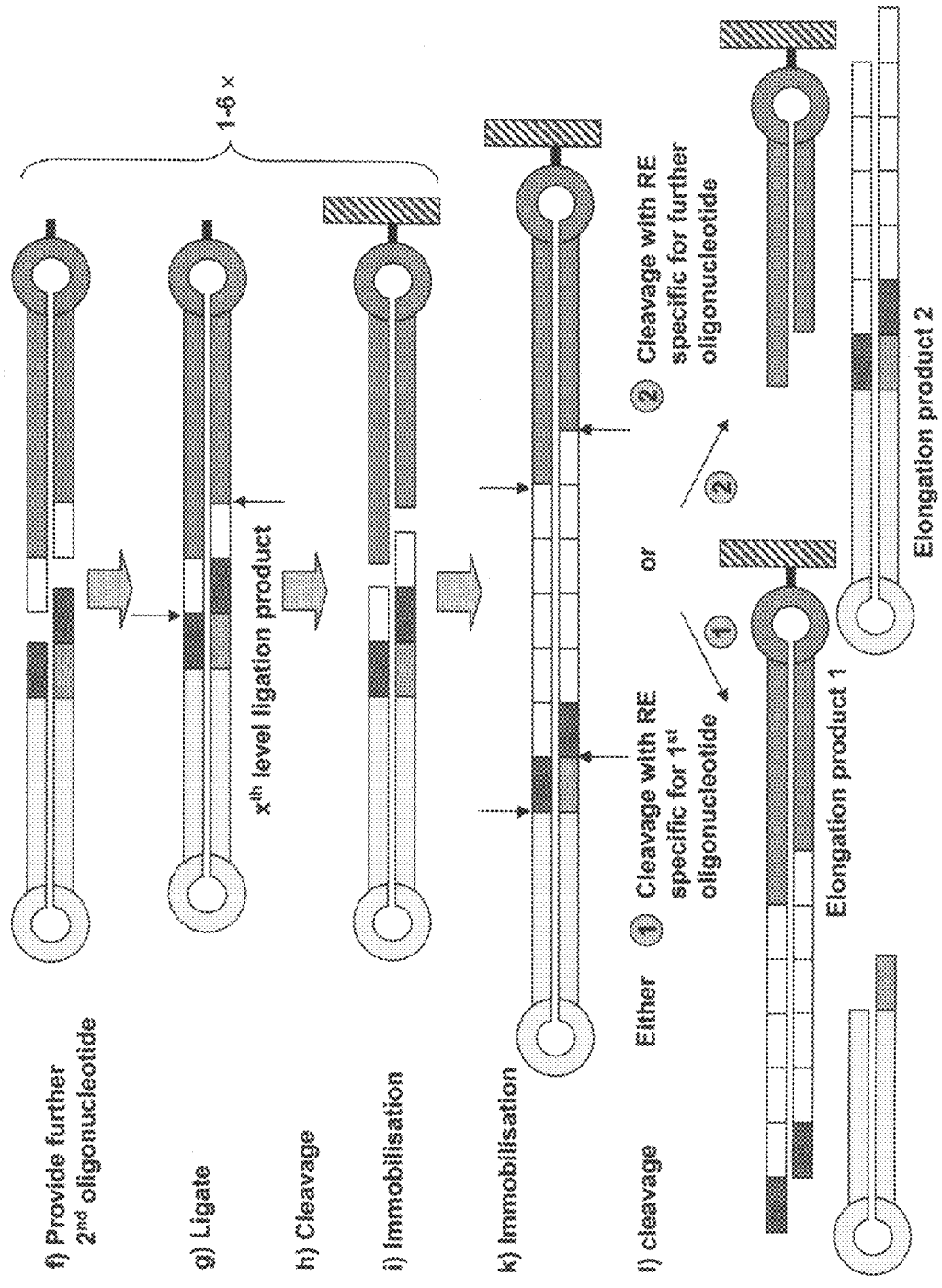
Fig. 18 – S4LS

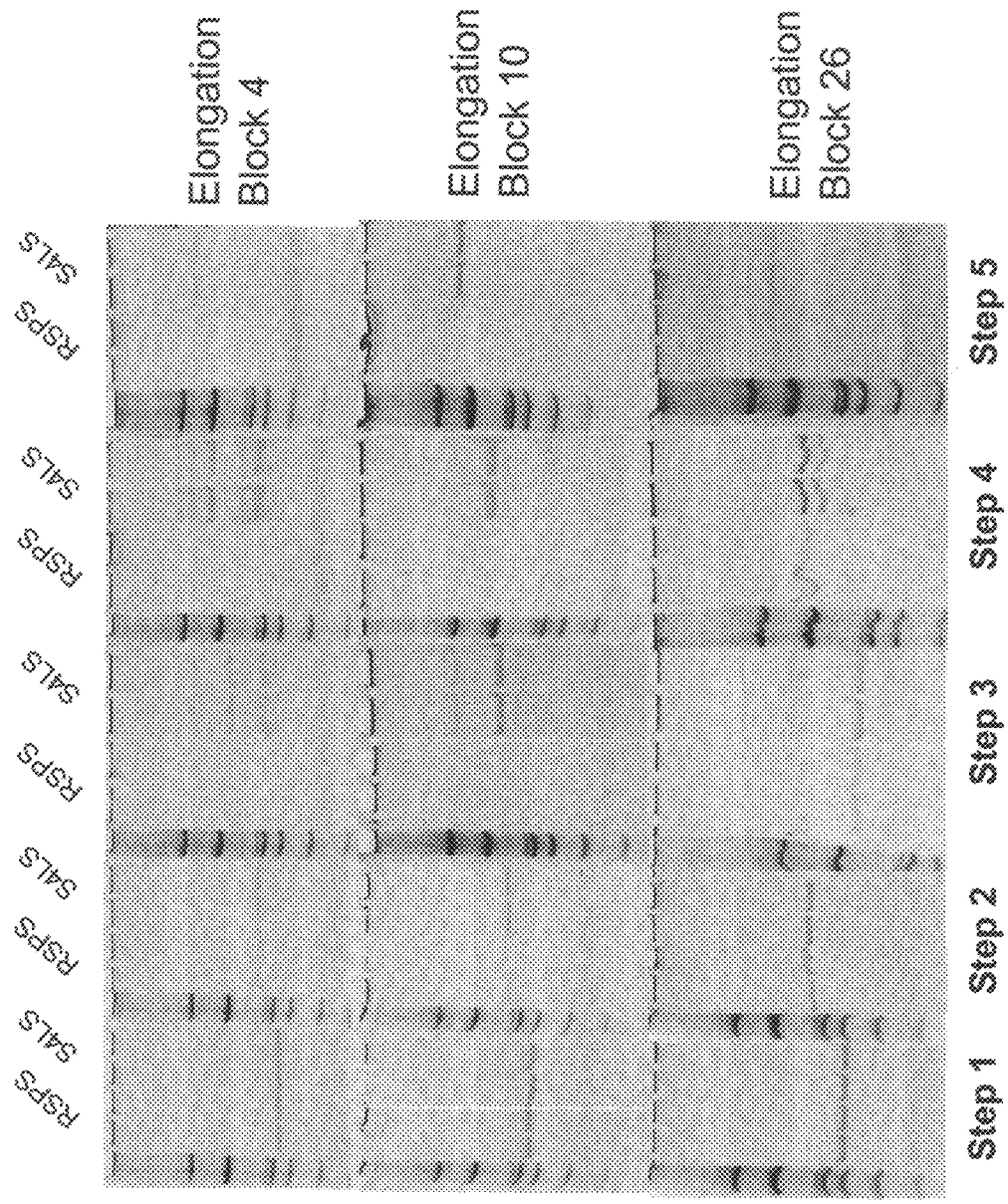
Fig. 19 – S4LS vs RSPS

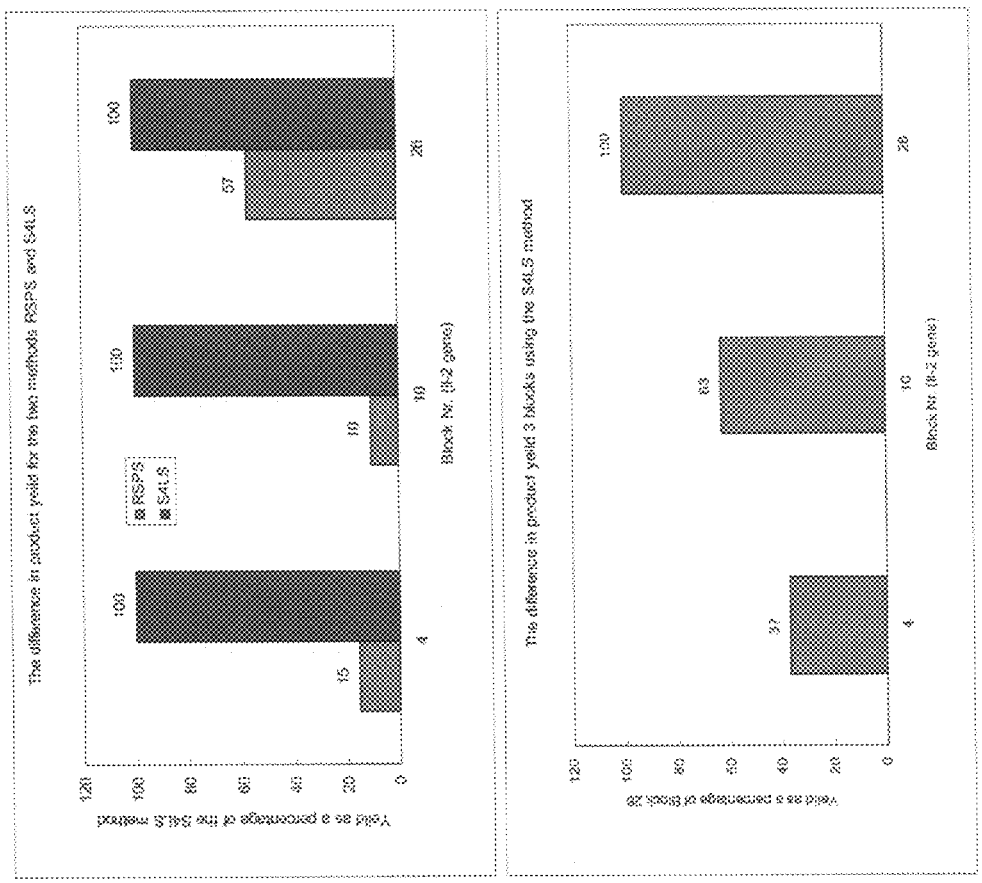
Fig. 20 – S4LS vs RSPS

DE NOVO ENZYMATIC PRODUCTION OF NUCLEIC ACID MOLECULES

This application is a 371 of PCT/EP2005/000620, filed on Jan. 22, 2005, which claims priority under 35 U.S.C. Section 119(a) to EP Patent Application 04001462.3 filed on Jan. 23, 2004, both of which are herein incorporated by reference.

The present invention is related to methods for the manufacture of a nucleic acid molecule and methods for the ligation of oligonucleotides.

De novo generation of nucleic acid molecules is increasingly used in biopharmaceutical research to replace the often quite complex cloning procedures necessary to produce desired DNA constructs with optimised properties, e.g. high level protein expression in suitable in vivo or in vitro systems. There are a variety of methods known to synthesise such DNA molecules. Practically all of these procedures rely on the synthesis, annealing and subsequent ligation of synthetic single-stranded oligonucleotides to assemble larger double-stranded DNA molecules that typically consist of more than one hundred up to several thousand base pairs. However, the efficiency of these methods is limited by several factors: (i) the quality of the oligonucleotides used, (ii) the size of the desired construct and (iii) the proportion of "difficult" sequences, e.g. those with self-complementary regions, high GC content, G tetrads, DNA kinks or repetitive sequence blocks. The oligonucleotide building blocks themselves are contaminated with various termination products and internal deletions. Especially problematic are n−1 products (oligonucleotides containing internal one nucleotide deletions occurring as a result of incomplete capping reactions), which can hardly be separated from the desired full-length oligonucleotide. As many oligonucleotides have to be assembled in order to generate a complete gene, the probability of obtaining an error-free clone, i.e. not incorporating even one defective oligonucleotide with a base change or an internal deletion approaches 0%. For example, if a gene were assembled from fifty oligonucleotides each having a purity of 90%, the probability of creating an error-free product would be roughly $0.9^{50}=0.005$. Generally, tedious error correction procedures must be employed in order to obtain a 100% error-free construct. In many cases, defective synthesis products cannot be tolerated because mistakes in the coding sequence may cause the generation of shortened transcription or translation products due to e.g. a frame shift of the open reading flame. Whereas the first two problems can be alleviated by the use of oligonucleotides of very high purity, the formation of unwanted secondary structures that may cause deletions in the synthesis product can in many cases only be suppressed if alterations are allowed in the DNA sequence.

In the prior art a variety of methods are known to produce synthetic DNA. More than 20 years ago, the pioneering work of Khorana and colleagues (Sekiya et al., 1979) demonstrated the complete de novo synthesis of a suppressor tRNA gene via ligation of pairs of annealed oligonucleotides. In this and related methods, complementary single-stranded oligonucleotides comprising the complete desired DNA sequence are annealed in pairs to yield double-stranded fragments, which are aligned in the correct order by virtue of complementary single-stranded overhangs (Stabinsky, U.S. Pat. No. 4,652,639). The resulting fragments are then ligated either sequentially or in a one-tube-reaction (Jayaraman, U.S. Pat. No. 5,132,215) either enzymatically or chemically. After purification and/or cloning these gene fragments may be joined together to form larger DNA constructs. In the so-called "cassette synthesis", each pair of annealed oligonucleotides is separately cloned in a plasmid vector before joining the fragments using restriction endonucleases (Richards et al., U.S. Pat. No. 5,093,251).

Alternatively, DNA constructs can be assembled from partially annealed oligonucleotides, which after hybridisation contain single-stranded gaps that must be filled by DNA polymerases; this method is commonly referred to as "gap filling" method. According to this method a variety of partially overlapping oligonucleotides are synthesised, purified and subsequently hybridised usually in pairs or in subgroups. After the synthesis of the respective opposite strands using a DNA polymerase the individual fragments are ligated to each other. The double stranded ligation products generated in this way may be either cloned as partial fragments or amplified in a polymerase chain reaction (PCR) with terminal oligonucleotide primers. However, this method is plagued by frequent mispriming events and internal deletions due to the formation of secondary structures.

Both methods are of limited use as with increasing length of the nucleic acid molecule to be synthesised the probability increases that one or several oligonucleotides with an incorrect sequence will be incorporated into the final product. Such errors are then copied in the DNA polymerase reaction. In addition, sequence errors may also be introduced during the PCR reaction.

A combination of the above methods is described in U.S. Pat. No. 6,472,184 in which a series of linkable oligonucleotides representing adjoining regions in one strand of the target sequence are hybridised with non-linkable oligonucleotides that are complementary to the 3' or 5' ends of the linkable oligonucleotides that are to be connected. This method is relatively simple and straightforward but is also plagued by the common problems shared by all procedures that use single-stranded oligonucleotides as building blocks: the formation of unwanted secondary structures and the incorporation of n-x oligonucleotides, which both lead to internal deletions.

Besides these standard procedures, there are further methods known in the art for the production of synthetic DNA molecules. International patent application WO 98/15567 and U.S. Pat. No. 6,110,668 teach a template-directed method of coupling oligonucleotides to yield synthetic DNA constructs by ligating a plurality of oligonucleotides that are at least partially complementary to the single-stranded template DNA and the ends of said oligonucleotides are ligated in the correct order in successive annealing and denaturation steps. However, a precondition for the application of this method is the prior existence of a suitable template DNA excluding its use in de novo synthesis.

International patent application WO 99/47536 discloses a solid phase gene synthesis method in which single-stranded oligonucleotides are sequentially ligated to an immobilised starter molecule in a defined orientation. A disadvantage of this method is that many steps are required to synthesise larger genes resulting in reduced yield and enrichment of defective sequences. Also, this method is difficult to automate which is a prerequisite for a rapid, standardised synthesis.

International patent application WO 00/75368 discloses a combinatorial solid phase synthesis of nucleic acids using a library of double-stranded oligonucleotides as standardised building blocks. The use of standardised building blocks makes it unnecessary to synthesise a new set of oligonucleotides for each new synthesis. These double-stranded library oligonucleotides generally share an identical overall structure and thus avoid common synthesis problems caused by the formation of alternative secondary structures of the oligonucleotide building blocks such as the introduction of deletions. In one preferred version, they contain a terminal loop, a double-stranded stem and a short single-stranded overhang. There are two different classes of library oligonucleotides, which are characterised by the presence of different recognition sites for type IIS restriction enzymes within their sequence and the presence or absence or the type of an internal modification. The nucleotides in the overhang and the directly adjacent region form the variable portion that actually contributes to the nucleic acid to be synthesize d; the remaining sequence is generally identical in all oligonucleotides belonging to the same class.

To build up a double-stranded nucleic acid, its sequence is first broken down into smaller fragments (usually between 6 and 30 base pairs each). These so-called elongation blocks are then synthesised in parallel reactions. In one such reaction, two double-stranded library oligonucleotides, one of each class, are ligated via matching single-stranded overhangs. The ligation products thereof are subsequently cleaved with the type IIS restriction enzyme, which is specific for the oligonucleotide that donates nucleotides. The net effect of such a ligation/restriction cycle is the addition of a small number of base pairs (typically between one to five) to the starting oligonucleotide. This process is then repeated until the synthesis of the desired elongation block is completed.

In a second reaction phase, the so-called transposition, those elongation blocks that are adjacent in the nucleic acid to be synthesised are ligated in a pair wise fashion after each block has been cleaved with a different type IIS restriction enzyme. By repeating this procedure several times the length of the transposition intermediates doubles in each step whereas the number of reactions is cut in half. Thus a defined nucleic acid molecule can be generated in very few cycles. The advantage of this method resides in the combinatorial pair wise assembly of the fragments of the nucleic acid molecule to be synthesised, in a sequence independent manner. Any desired elongation block may thus be generated from a standardised nucleic acid library with a defined number of elements.

The number of the elements of such a library depends on the length of the overhangs generated by the individual type IIS restriction enzyme as well as the number of nucleotides that are added to the growing oligonucleotides in each elongation cycle.

This method offers a number of advantages: it can be completely automated since there is no need to synthesise and purify new oligonucleotides to build large genes or DNA fragments, the building blocks are prepared in a large scale and can be used to assemble many different constructs until the supply is used up thus reducing the cost for oligonucleotides by one to two orders of magnitude. However, an inherent disadvantage of this method is the fact that the individual intermediates to be ligated in a pair wise fashion may be produced in different yield.

In some cases, the resulting uneven stoichiometry of the ligation partners may lead to the formation of unwanted side products that can further decrease the yield of subsequent ligations.

The problem underlying the present invention is to provide a method for the manufacture of a nucleic acid molecule which allows for an increased yield and/or a nucleic acid molecule having a more accurate sequence compared to the methods according to the prior art, According to the present invention the problem is solved in a first aspect by a method for the manufacture of a nucleic acid molecule comprising the following steps:

a) providing a first at least partially double-stranded oligonucleotide, whereby the oligonucleotide comprises a first and a second single-stranded overhang, b) providing a second at least partially double-stranded oligonucleotide, whereby the oligonucleotide comprises a recognition site for a first type IIS restriction enzyme which cuts outside its recognition site, a modification allowing the oligonucleotide to be coupled to a surface and a single-stranded overhang, c) ligating the first oligonucleotide and the second oligonucleotide via the first single-stranded overhang of the first oligonucleotide and the single-stranded overhang of the second oligonucleotide, generating a first ligation product, whereby the first ligation product comprises a single-stranded overhang essentially corresponding to the second single-stranded overhang of the first oligonucleotide, d) cutting the first ligation product with the first type II restriction enzyme thus releasing
  an elongated first at least partially double-stranded oligonucleotide having a first and a second single-stranded overhang, whereby the first single-stranded overhang is generated through the cutting of the restriction enzyme and whereby the second single-stranded overhang corresponds essentially to the second single-stranded overhang of the first at least partially double-stranded oligonucleotide, preferably the at least partially double-stranded oligonucleotide of step (a), and
  a truncated second at least partially double-stranded oligonucleotide;

e) immobilising the truncated second at least partially double stranded oligonucleotide of step d), the unreacted second at least partially double-stranded oligonucleotide and/or the uncut first ligation product via the modification to a surface;

f) optionally repeating steps a) to e), whereby the elongated first at least partially double-stranded oligonucleotide of step d) serves as the first at least partially double-stranded oligonucleotide in step a).

In an embodiment the method comprises the following step
ca) immobilising the first ligation product via the long single-stranded overhang to a surface, In a preferred embodiment the surface comprises a nucleic acid having a single-stranded stretch which is at least partially complementary to the single-stranded overhang of the first ligation product.

In an embodiment the method comprises the following steps
cb) optionally washing the immobilised first elongation product; and
cc) releasing the immobilised first elongation product from the surface.

In an embodiment the length of the first single-stranded overhang of the first at least partially complementary oligonucleotide has a length of 1, 2, 3, 4 or 5 nucleotides.

In a further embodiment the second single-stranded overhang of the first oligonucleotide allows for a stable hybridisation to the single-stranded stretch of the nucleic acid comprised on the surface.

In a preferred embodiment the hybridisation is stable under the reaction conditions of step cb).

In an embodiment the single-stranded overhang has a length from about 5 to 20 nucleotides, from about 10 to 20 nucleotides, from about 15 to 18 nucleotides, from about 5 to 10 nucleotides and from about 6 to 8 nucleotides, depending on the nature of the nucleotides.

In an embodiment the modification is a biotin modification.

In an embodiment the immobilisation of step e) occurs via interaction of the biotin and the surface, whereby the surface preferably comprises a biotin interaction group.

In an embodiment the biotin interaction group is selected from the group comprising avidine, streptavidine, extravidine, mutants of each thereof and synthetic biotin binding sites.

In a preferred embodiment a part of the nucleic acid to be manufactured is part of the elongated first at least partially double-stranded oligonucleotide.

In an embodiment steps a) to e) are repeated at least once, whereby the nucleotides transferred from the second and any further at least partially double-stranded oligonucleotides provided in step b) to the first at least partially double-stranded oligonucleotides are the nucleic acid to be manufactured or a part thereof.

According to the present invention the problem is solved in a first aspect by a method for the manufacture of a nucleic acid molecule, preferably a double-stranded nucleic acid molecule comprising the following steps:
  a) providing an elongated first at least partially double-stranded oligonucleotide, preferably an elongated first at least partially double-stranded oligonucleotide obtainable by the method according to the first aspect of the present invention, whereby the nucleotides transferred from the second and/or any further at least partially double-stranded oligonucleotide are a first part of the nucleic acid molecule to be manufactured and the type IIS restriction enzyme is a first type IIS restriction enzyme,
  b) providing another elongated first at least partially double-stranded oligonucleotide, preferably an elongated first at least partially double-stranded oligonucleotide obtainable by the method according to the first aspect of the present invention, whereby the nucleotides transferred from the second and/or any further at least partially double-stranded oligonucleotide are a second part of the nucleic acid molecule to be manufactured and the type IIS restriction enzyme of the second at least partially double-stranded oligonucleotide is a second type IIS restriction enzyme and the type IIS restriction enzyme of the further at least partially double-stranded oligonucleotide is a further type IIS restriction enzyme, whereby the second type IIS restriction enzyme and/or the further type IIS restriction enzyme is different from the first type IIS restriction enzyme, and the second single-stranded overhang is different from the second single-stranded overhang of the elongated first at least partially double-stranded oligonucleotide as of step a)
  c) ligating the oligonucleotides of step a) and b) producing a first extended ligation product,
  d) immobilising the first extended ligation product of step c) via the second single-stranded overhang of the oligonucleotide of step a),
  e) optionally washing away the supernatant,
  f) releasing the first extended ligation product of step c),
  g) immobilising the first extended ligation product of step c) via the second single-stranded overhang of the oligonucleotide of step b),
  h) optionally washing away the supernatant,
  i) releasing the first extended ligation product from step c), whereby the first part of the nucleic acid molecule to be manufactured and the second part of the nucleic acid molecule to be manufactured are consecutively arranged in the nucleic acid molecule to be manufactured.

In an embodiment of the method according to the second aspect steps a) to i) are carried out in a separate reaction and whereby
  the elongated first at least partially double-stranded oligonucleotide of step a) comprises as nucleotides transferred from the second and/or any further at least partially double-stranded oligonucleotide nucleotides which form a third part of the nucleic acid molecule to be manufactured, and
  the another elongated first at least partially double-stranded oligonucleotide of step a) comprises as nucleotides transferred from the second and/or any further at least partially double-stranded oligonucleotide nucleotides which form a fourth part of the nucleic acid molecule to be manufactured,
  generating a second extended ligation product.

In an embodiment of the method according to the second aspect,
  the first extended ligation product is cleaved by the second type IIS restriction enzyme generating
  in step j)
    a cut first extended ligation product, and
    an at least partially double-stranded oligonucleotide corresponding to the first at least partially double-stranded oligonucleotide used in the generation of the elongated at least partially double-stranded oligonucleotide of step a),
  wherein the second extended ligation product is cleaved by the first type IIS restriction enzyme generating
  in step k)
    a cut second extended ligation product and
    an at least partially double-stranded oligonucleotide corresponding to the first at least partially double-stranded oligonucleotide used in the generation of the elongated at least partially double-stranded oligonucleotide of step b)

In an embodiment of the method according to the second aspect, the method comprises as step
  l) ligating the cut first extended ligation product and the cut second extended ligation product.

In an embodiment of the method according to the second aspect the at least partially double-stranded oligonucleotide of step k) is immobilised through the second single-stranded overhang to a surface, whereby the surface comprises a nucleic acid molecule having at least a single-stranded stretch which is at least partially complementary to the second single-stranded overhang.

In an embodiment of the method according to the second aspect the at least partially double-stranded oligonucleotide of step l) is immobilised through the second single-stranded overhang to a surface, whereby the surface comprises a nucleic acid molecule having at least a single-stranded stretch which is at least partially complementary to the second single-stranded overhang.

In an embodiment of the method according to the second aspect the ligation product of step k) is used as an elongated first at least partially double stranded oligonucleotide in step a) and a ligation product obtained in step k) using parts 5 to 8 of the nucleic acid to be manufactured obtained by the method according to the second aspect of the invention is used as the another elongated first at least partially double-stranded oligonucleotide in step b).

In an embodiment of the method according to the second aspect the type IIS restriction enzyme is selected from the group comprising Eco 31I and Esp 3I.

According to the present invention the problem is solved in a third aspect by a method for the manufacture of a nucleic acid molecule comprising the following steps:
- a) providing a first ligation product, whereby the first ligation product consists of a first oligonucleotide moiety comprising a recognition site for a first type IIS restriction enzyme, a second oligonucleotide moiety comprising a recognition site for a second type IIS restriction enzyme and a modification allowing specific binding to a solid phase, and a third oligonucleotide moiety in between, whereby the third oligonucleotide moiety is a part of the nucleic acid molecule to be manufactured, and whereby the first and the second type IIS restriction enzymes each generate upon cleavage an overhang, whereby preferably the overhang generated by the first type IIS restriction enzyme has a length which is different from the length of the overhang generated by the second type IIS restriction enzyme;
- b) providing a second ligation product, whereby the second ligation product consists of a first oligonucleotide moiety comprising a recognition site for a third type IIS restriction enzyme, a second oligonucleotide moiety comprising a recognition site for a fourth type IIS restriction enzyme and a modification allowing specific binding to a solid phase, and a third oligonucleotide moiety in between, whereby the third oligonucleotide moiety is a part of the nucleic acid molecule to be manufactured, and whereby the third and the fourth type IIS restriction enzyme each generate upon cleavage an overhang, whereby optionally the overhang generated by the third type IIS restriction enzyme has a length which is different from the length of the overhang generated by the fourth type IIS restriction enzyme;
- c) providing a third ligation product, whereby the third ligation product consists of a first oligonucleotide moiety comprising a recognition site for a fifth type IIS restriction enzyme, a second oligonucleotide moiety comprising a recognition site for a sixth type IIS restriction enzyme and a modification allowing specific binding to a solid phase, and a third oligonucleotide moiety in between, whereby the third oligonucleotide moiety is a part of the nucleic acid molecule to be manufactured, and whereby the fifth and the sixth type IIS restriction enzymes each generate an overhang, whereby optionally the overhang generated by the fifth type IIS restriction enzyme has a length which is different from the length of the overhang generated by the sixth type IIS restriction enzyme;
- d) providing a fourth ligation product, whereby the fourth ligation product consists of a first oligonucleotide moiety comprising a recognition site for a seventh type IIS restriction enzyme, a second oligonucleotide moiety comprising a recognition site for an eighth type IIS restriction enzyme and a modification allowing specific binding to a solid phase, and a third oligonucleotide moiety in between, whereby the third oligonucleotide moiety is a part of the nucleic acid molecule to be manufactured, and whereby the seventh and the eighth type IIS restriction enzyme each generate an overhang, whereby preferably the overhang generated by the seventh type IIS restriction enzyme has a length which is different from the length of the overhang generated by the eighth type IIS restriction enzyme; whereby the third oligonucleotide moiety of the first and of the second ligation product each comprise the part of the nucleic acid to be manufactured in the same orientation and the third oligonucleotide moiety of the third and of the fourth ligation product each comprise the part of the nucleic acid to be manufactured in the same orientation, whereby
  either the orientation of the parts of the nucleic acid molecule to be manufactured as contained in the first and second ligation product is the same as in the nucleic acid molecule to be manufactured and the orientation of the parts of the nucleic acid molecule to be manufactured as contained in the third and the fourth ligation product is opposite to the orientation as in the nucleic acid molecule to be manufactured;
  or the orientation of the parts of the nucleic acid molecule to be manufactured as contained in the first and second ligation product is opposite to the orientation as in the nucleic acid molecule to be manufactured, and the orientation of the parts of the nucleic acid molecule to be manufactured as contained in the third and the fourth ligation product is the same as in the nucleic acid molecule to be manufactured;
- e) cutting the first ligation product with the first type IIS restriction enzyme generating a first cut ligation product and cutting the second ligation product with the fourth restriction enzyme generating a second cut ligation product;
- f) cutting the third ligation product with the sixth type IIS restriction enzyme generating a third cut ligation product and cutting the fourth ligation product with the seventh restriction enzyme generating a fourth cut ligation product;
- g) combining and ligating the first cut ligation product and the second cut ligation product generating a first transposition product, whereby the first transposition product is cut by the third type IIS restriction enzyme generating a cut first transposition product;
- h) combining and ligating the third ligation product and the fourth ligation product providing a second transposition product, whereby the second transposition product is cut by both the fifth and the eighth type IIS restriction enzyme generating a cut second transposition product; and
- i) ligating the cut first transposition product and the cut second transposition product generating a second order transposition product.

In an embodiment of the method according to the third aspect the first type IIS restriction enzyme, the third type IIS restriction enzyme, the fifth type IIS restriction enzyme and the seventh type IIS restriction enzyme are the same.

In an embodiment of the method according to the third aspect the second type IIS restriction enzyme and the eighth type IIS restriction enzyme are the same.

In an embodiment of the method according to the third aspect the fourth type IIS restriction enzyme and the sixth type IIS restriction enzyme are the same In an embodiment of the method according to the third aspect the restriction enzyme is selected from the group comprising Esp3I, Eco31I and Earn 1104 I.

In an embodiment of the method according to the third aspect the second and the third ligation product are immobilized to a surface via the modification prior to the cutting with the restriction enzymes.

In a preferred embodiment of the method according to the third aspect the supernatant obtained by cutting the immobilized second ligation product is ligated to the immobilized cut first ligation product, and wherein the supernatant obtained by cutting the immobilized third ligation product is ligated to the immobilized cut fourth ligation product.

In an embodiment of the method according to the third aspect the length of the double-stranded stretch of the second cut transposition product is selected from the group comprising 17, 18, 19, 20, 21, 22, 23, 24, 25, 26, 27, 28, 29, 30, 31, 32, 33, 34, 35, 36, 37 or 38 base pairs.

In an embodiment of the method according to the third aspect the third oligonucleotide moiety of the first ligation product forms a first part of the nucleic acid molecule to be manufactured and the third oligonucleotide moiety of the second ligation product forms a second part of the nucleic acid molecule to be manufactured, whereby the first part and the second part are consecutive parts of the nucleic acid molecule to be manufactured and both the first part and the second part have the same orientation in the first ligation product and the second ligation product.

In an embodiment of the method according to the third aspect the third oligonucleotide moiety of the third ligation product forms a third part of the nucleic acid molecule to be manufactured and the third oligonucleotide moiety of the fourth ligation product forms a fourth part of the nucleic acid molecule to be manufactured, whereby the third part and the fourth part are consecutive parts of the nucleic acid molecule to be manufactured and both the third part and the fourth part have the same orientation in the third ligation product and the fourth ligation product, whereby the orientation of the third part and the fourth part is inverse compared to the orientation of the first and second part.

In an embodiment of the method according to the third aspect the second order transposition product is used as the first transposition product in step f) of the method, and a further second order transposition product is used as the second transposition product of step g) of the method, whereby the parts of the nucleic acid to be manufactured provided by the second order transposition product and the parts of the nucleic acid to be manufactured provided by the further second order transposition product are in an inverse orientation According to the present invention the problem is solved in a fourth aspect by a method for the manufacture of a nucleic acid molecule comprising the following steps:

a) providing a first ligation product, whereby the first ligation product consists of a first oligonucleotide moiety comprising a recognition site for a first type IIS restriction enzyme, a second oligonucleotide moiety comprising a recognition site for a second type IIS restriction enzyme and a modification allowing specific binding to a solid phase, and a third oligonucleotide moiety in between, whereby the third oligonucleotide moiety is a part of the nucleic acid molecule to be manufactured, and whereby the first and the second type IIS restriction enzymes each generate upon cleavage an overhang, whereby preferably the overhang generated by the first type IIS restriction enzyme has a length which is different from the length of the overhang generated by the second type IIS restriction enzyme;

b) providing a second ligation product, whereby the second ligation product consists of a first oligonucleotide moiety comprising a recognition site for a third type IIS restriction enzyme, a second oligonucleotide moiety comprising a recognition site for a fourth type IIS restriction enzyme and a modification allowing specific binding to a solid phase, and a third oligonucleotide moiety in between, whereby the third oligonucleotide moiety is a part of the nucleic acid molecule to be manufactured, and whereby the third and the fourth type IIS restriction enzyme each generate upon cleavage an overhang, whereby optionally the overhang generated by the third type IIS restriction enzyme has a length which is different from the length of the overhang generated by the fourth type IIS restriction enzyme;

c) providing a third ligation product, whereby the third ligation product consists of a first oligonucleotide moiety comprising a recognition site for a fifth type IIS restriction enzyme, a second oligonucleotide moiety comprising a recognition site for a sixth type IIS restriction enzyme and a modification allowing specific binding to a solid phase, and a third oligonucleotide moiety in between, whereby the third oligonucleotide moiety is a part of the nucleic acid molecule to be manufactured, and whereby the fifth and the sixth type IIS restriction enzymes each generate an overhang, whereby optionally the overhang generated by the fifth type IIS restriction enzyme has a length which is different from the length of the overhang generated by the sixth type IIS restriction enzyme;

d) providing a fourth ligation product, whereby the fourth ligation product consists of a first oligonucleotide moiety comprising a recognition site for a seventh type IIS restriction enzyme, a second oligonucleotide moiety comprising a recognition site for an eighth type IIS restriction enzyme and a modification allowing specific binding to a solid phase, and a third oligonucleotide moiety in between, whereby the third oligonucleotide moiety is a part of the nucleic acid molecule to be manufactured, and whereby the seventh and the eighth type IIS restriction enzyme each generate an overhang, whereby preferably the overhang generated by the seventh type IIS restriction enzyme has a length which is different from the length of the overhang generated by the eighth type IIS restriction enzyme;

e) cutting the first ligation product with the second type IIS restriction enzyme generating a first cut ligation product and cutting the fourth ligation product with the fourth restriction enzyme generating a fourth cut ligation product;

f) cutting the second ligation product with the second type IIS restriction enzyme generating a second cut ligation product and cutting the third ligation product with the sixth restriction enzyme generating a third cut ligation product;

g) combining the first cut ligation product and the second cut ligation product in the presence of a ligase and the third type IIS restriction enzyme generating a first transposition product, generating a cut first transposition product;

h) combining the third ligation product and the fourth ligation product in the presence of a ligase and the fifth type IIS restriction enzyme providing a second transposition product, whereby the second transposition product is cut by the fifth and the eighth type IIS restriction enzyme generating a cut second transposition product; and i) ligating the cut first transposition product and the cut second transposition product generating a second order transposition product.

In an embodiment of the method according to the fourth aspect the first type IIS restriction enzyme, the third type IIS restriction enzyme, the fifth type IIS restriction enzyme, and the seventh type IIS restriction enzyme are the same.

In an embodiment of the method according to the fourth aspect the second type IIS restriction enzyme and the eighth type IIS restriction enzyme are the same.

In an embodiment of the method according to the fourth aspect the fourth type IIS restriction enzyme and the sixth type IIS restriction enzyme are the same.

In an embodiment of the method according to the fourth aspect the restriction enzyme is selected from the group comprising Esp3I, Eco31 and Eam 1104 I.

In an embodiment of the method according to the fourth aspect the first and the fourth ligation product are immobilized to a surface via the modification prior to the cutting with the restriction enzymes.

In a preferred embodiment of the method according to the fourth aspect the supernatant obtained by cutting the immobilized second ligation product is ligated to the immobilized cut first ligation product, while the third type IIS restriction enzyme is present and, preferably active, and wherein the supernatant obtained by cutting the immobilized third ligation product is ligated to the immobilized cut fourth ligation product, while the fifth type IIS restriction enzyme is present.

In an embodiment of the method according to the fourth aspect the length of the double-stranded stretch of the second cut transposition product is selected from the group comprising 17, 18, 19, 20, 21, 22, 23, 24, 25, 26, 27, 28, 29, 30, 31, 32, 33, 34, 35, 36, 37 or 38 base pairs.

In an embodiment of the method according to the fourth aspect the third oligonucleotide moiety of the first and of the third ligation product each comprise the part of the nucleic acid to be manufactured in the same orientation and the third oligonucleotide moiety of the second and of the fourth ligation product each comprise the part of the nucleic acid to be manufactured in the same orientation,
whereby
either the orientation of the parts of the nucleic acid molecule to be manufactured as contained in the first and third ligation product is the same as in the nucleic acid molecule to be manufactured and the orientation of the parts of the nucleic acid molecule to be manufactured as contained in the second and the fourth ligation product is opposite to the orientation as in the nucleic acid molecule to be manufactured;
or the orientation of the parts of the nucleic acid molecule to be manufactured as contained in the first and third ligation product is opposite to the orientation as in the nucleic acid molecule to be manufactured, and the orientation of the parts of the nucleic acid molecule to be manufactured as contained in the second and the fourth ligation product is the same as in the nucleic acid molecule to be manufactured.

In an embodiment of the method according to the fourth aspect the second order transposition product is used as the first transposition product in step f) of the method, and a further second order transposition product is used as the second transposition product of step g) of the method, whereby the parts of the nucleic acid to be manufactured provided by the second order transposition product and the parts of the nucleic acid to be manufactured provided by the further second order transposition product are in an inverse orientation According to the present invention the problem is solved in a fifth aspect by a method for the ligation of a first oligonucleotide and a second oligonucleotide, whereby
the first oligonucleotide and the second oligonucleotide are contained in a ligation reaction;
the first oligonucleotide is an at least partially double-stranded oligonucleotide having a single stranded overhang, and the second oligonucleotide is an at least partially double-stranded oligonucleotide having a single stranded overhang, whereby the single-stranded overhang of the first oligonucleotide and the single-stranded overhang of the second oligonucleotide are overlapping so as to allow for a ligation of the first and the second oligonucleotide;
the ligation reaction comprises at least a further oligonucleotide, whereby such further oligonucleotide comprises a partial sequence, whereby the partial sequence is suitable to be ligated to the first oligonucleotide or to the second oligonucleotide;
and a capping oligonucleotide, whereby such capping oligonucleotide comprises an at least partially a double-stranded structure and a single-stranded overhang, whereby the single stranded overhang allows ligation to the further oligonucleotide.

In an embodiment of the method according to the fifth aspect the single-stranded overhang of the first oligonucleotide and the single-stranded overhang of the second oligonucleotide are complementary to each other, preferably allowing a perfect match.

In an embodiment of the method according to the fifth aspect the length of the single-stranded overhang of the first oligonucleotide and of the second oligonucleotide is each independently selected from the group comprising a two nucleotide overhang, a three nucleotide overhang, a four nucleotide overhang, a five nucleotide overhang, a six nucleotide overhang and a seven nucleotide overhang.

In an embodiment of the method according to the fifth aspect the partial sequence of the further oligonucleotide is essentially complementary to the single-stranded overhang, or part thereof, of the first oligonucleotide or of the second oligonucleotide.

In an embodiment of the method according to the fifth aspect the partial sequence of the further oligonucleotide, or part thereof, is complementary to a part of the single-stranded overhang, or part thereof, of the first oligonucleotide or of the second oligonucleotide.

In an embodiment of the method according to the fifth aspect the further oligonucleotide is at least partially double-stranded and comprises a single-stranded overhang, whereby the single-stranded overhang comprises the partial sequence.

In an embodiment of the method according to the fifth aspect the single-stranded overhang of the capping oligonucleotide, or part thereof, is essentially complementary to the partial sequence of the further oligonucleotide, or part thereof.

In an embodiment of the method according to the fifth aspect the ligation reaction between the further oligonucleotide and the capping oligonucleotide is preferred to the ligation of the further oligonucleotide and the first and second oligonucleotide, respectively.

In an embodiment of the method according to the fifth aspect the capping oligonucleotide is not ligating to the first and second oligonucleotide in the ligation reaction.

In an embodiment of the method according to the fifth aspect the capping oligonucleotide is contained in the ligation reaction in excess, preferably 2-10 fold.

In an embodiment of the method according to the fifth aspect the capping oligonucleotide comprises a loop structure, preferably a loop structure at the end opposite to the single-stranded overhang.

According to the present invention the problem is solved in a sixth aspect by a method for the manufacture of a nucleic acid molecule, comprising the steps of
a) providing a first at least partially double-stranded oligonucleotide which comprises a recognition site for a first type IIS restriction enzyme which cuts outside its recognition site, and which oligonucleotide comprises a single-stranded overhang;
b) providing a second at least partially double-stranded oligonucleotide which comprises a modification allowing the oligonucleotide to be coupled to a surface, whereby the oligonucleotide further comprises a recognition site or a part thereof or a sequence which is complementary thereto, for a second type IIS restriction enzyme which cuts outside its recognition site, and which second oligonucleotide comprises a single-stranded overhang;

c) ligating the first and the second oligonucleotide via their overhangs generating a first ligation product;

d) immobilising the first ligation product on a surface via the modification contributed by the second oligonucleotide e) cutting the immobilised first ligation product with the second type IIS restriction enzyme thus releasing an elongated first oligonucleotide having an overhang and a shortened second oligonucleotide, which remains bound to the surface;

f) providing a further at least partially double-stranded oligonucleotide which has a modification allowing the further oligonucleotide to be specifically coupled to a surface, whereby the oligonucleotide contains a recognition site for a second or a further type IIS restriction enzyme and a single-stranded overhang which is complementary to the overhang of the elongated first oligonucleotide;

g) ligating the further at least partially double-stranded oligonucleotide with the elongated first oligonucleotide via their overhangs generating a second level ligation product;

h) cutting the second level ligation product with the second or further type IIS restriction enzyme thus generating a second level elongated oligonucleotide having an overhang and a shortened further oligonucleotide;

i) immobilising the shortened further oligonucleotide;

j) repeating steps f) to i) at least once, generating in step g) a higher level ligation product, whereby in the last repetition the incoming further oligonucleotide comprises a recognition site for a type IIS restriction enzyme which upon cleavage produces a single-stranded overhang identical in length to the overhang generated by the first type IIS restriction enzyme specific for the first oligonucleotide, and steps h) and i) are replaced by the steps k) and l)

k) immobilising the higher level ligation product via the modification provided by the further oligonucleotide; and l) cutting the higher level ligation product with the further type IIS restriction enzyme, leaving the part of the nucleic acid to be manufactured attached to the first oligonucleotide, which is preferably released into the supernatant, and more preferably allowing its transfer to a new reaction vessel.

According to the present invention the problem is solved in a seventh aspect by a method for the manufacture of a nucleic acid molecule, comprising the steps of a) providing a first at least partially double-stranded oligonucleotide which comprises a recognition site for a first type IIS restriction enzyme which cuts outside its recognition site, and which oligonucleotide comprises a single-stranded overhang;

b) providing a second at least partially double-stranded oligonucleotide which comprises a modification allowing the oligonucleotide to be coupled to a surface, whereby the oligonucleotide further comprises a recognition site or a part thereof or a sequence which is complementary thereto, for a second type IIS restriction enzyme which cuts outside its recognition site, and which second oligonucleotide comprises a single-stranded overhang;

c) ligating the first and the second oligonucleotide via their overhangs generating a first ligation product;

d) immobilising the first ligation product on a surface via the modification contributed by the second oligonucleotide;

e) cutting the immobilised first ligation product with the second type IIS restriction enzyme thus releasing an elongated first oligonucleotide having an overhang and a shortened second oligonucleotide, which remains bound to the surface;

f) providing a further at least partially double-stranded oligonucleotide which has a modification allowing the further oligonucleotide to be specifically coupled to a surface, whereby the oligonucleotide contains a recognition site for a second or further type IIS restriction enzyme and a single-stranded overhang which is complementary to the overhang of the elongated first oligonucleotide;

g) ligating the further at least partially double-stranded oligonucleotide with the elongated first oligonucleotide via their overhangs generating a second level ligation product;

h) cutting the second level ligation product with the second or further type IIS restriction enzyme thus generating a second level elongated oligonucleotide having an overhang and a shortened further oligonucleotide;

i) immobilising the shortened further olignucleotide;

j) repeating steps f) to i) at least once, generating in step g) a higher level ligation product, whereby in the last repetition the incoming further oligonucleotide comprises a recognition site for a type IIS-restriction enzyme which upon cleavage produces a single-stranded overhang identical in length to the overhang generated by the first type IIS restriction one specific for the first oligonucleotide, and steps h) and i) are replaced by the steps k) and l)

k) immobilising the higher level ligation product via the modification provided by the further oligonucleotide; and l) cutting the immobilised higher level ligation product with the type IIS restriction enzyme specific for the first oligonucleotide, leaving the part of the nucleic acid to be manufactured attached to the further oligonucleotide, which is immobilised on a surface.

In an embodiment of the method according to the sixth and/or seventh aspect as step m) the cut immobilised higher level ligation product of step l) of the method according to the seventh aspect of the present invention is ligated with the cut higher level ligation product of step l) of the method according to the sixth aspect of the present invention.

In an embodiment of the method according to the sixth and/or seventh aspect the cut higher level ligation product of step l) of the method according to the sixth aspect of the present invention is cleaved with the second type IIS restriction enzyme prior to the ligation step m).

In an embodiment of the method according to the sixth and/or seventh aspect the number of repetitions in step j) is two, three, four, five or six.

In an embodiment of the method according to the sixth and/or seventh aspect the overhang is a 5' or a 3' overhang.

In an embodiment of the method according to the sixth and/or seventh aspect the overhang is selected from the group comprising a one nucleotide overhang, a two nucleotides overhang, a three nucleotides overhang, a four nucleotides overhang, and a five nucleotides overhang.

In an embodiment of the method according to the sixth and/or seventh aspect the at least partially double-stranded oligonucleotide comprises a constant region and a variable region, whereby the constant region contains the recognition site for a type IIS restriction enzyme, and the variable region contains a nucleic acid sequence which corresponds to a part of the nucleic acid sequence of the nucleic acid molecule to be manufactured.

In an embodiment of the method according to the sixth and/or seventh aspect the further type IIS restriction enzyme is the second type IIS restriction enzyme.

In an embodiment of the method according to the sixth and/or seventh aspect the elongated oligonucleotide is transferred to a different reaction vessel.

In an embodiment of the method according to the sixth and/or seventh aspect the second level elongated oligonucleotide is transferred to a different reaction vessel.

In an embodiment of the method according to the sixth and/or seventh aspect the second level elongated oligonucleotide is used as the elongated oligonucleotide in step g).

In an embodiment of the method according to the sixth and/or seventh aspect the modification of the elongated oligonucleotide and/or of the higher level ligation product is provided by the further at least partially double-stranded oligonucleotide.

According to the present invention the problem is solved in an eighth aspect by the use of the method according to the fifth aspect of the present invention in any method according to any aspect of the present invention, more particularly in any ligation reaction thereof.

The present inventors have surprisingly found that the design of building blocks which are used in combinatorial synthesis of a nucleic acid using a library of double-stranded oligonucleotides as standardised building blocks such as described in international patent application WO 00/75368 or international patent application PCT/EP03/11551, allows for a further optimisation of the synthesis of nucleic acid molecules using this kind of synthesis strategy. Although the various embodiments of said combinatorial solid phase synthesis has proven a valuable tool for providing nucleic acid molecules, the need for an even more efficient synthesis using less chemicals, more particularly less amounts of enzymes, still exists. This need is met by the methods and tools for carrying out such methods.

The first aspect of the present invention is related to a method for the manufacture of a nucleic acid molecules. Said method is more particularly related to the manufacture of building blocks which can subsequently be used in the second step of the combinatorial synthesis of nucleic acid using a library of at least partially double-stranded oligonucleotides as described in international patent application WO 00/75368 or international patent application PCT/EP03/11551. The two main advantages of said building blocks is that they (i) provide for the possibility to select correct intermediate products, which is especially important in the second step of the method for the manufacture of a nucleic acid, the so-called transposition phase and (ii) allow to conduct all enzymatic reactions in the liquid phase thus significantly increasing the overall yield. This is accomplished by the introduction of at least two different "selector" sequences into the building blocks that allow a specific but reversible binding of the intermediates to oligonucleotides with a complementary sequence, which are coupled to a solid support. This kind of "selector" sequences are provided by the modification of the oligonucleotides to be ligated, more preferably by the second single-stranded overhang, most preferably by the second single-stranded overhang of the first and/or second at least partially double-stranded oligonucleotide. The intermediates can be easily bound to and eluted from the various types of solid support by simple incubation or heat denaturation, respectively. The recovered correct intermediates are then assembled in the next reaction cycle. In the simplest case, one utilises building blocks with two different selector sequences to generate two elongation blocks that are to be connected in the first transposition reaction. Even if one of the two elongation blocks were now in excess resulting in a mixture of correct reaction products and unreacted precursor, the desired (intermediate) product can be selected for by (i) binding the mixture to the solid support carrying a selector oligonucleotide complementary to the second overhang of the first elongation block, i.e. the "selector binding region" thereof (ii) washing away any unreacted second elongation block, which does not comprise the matching selector sequence in its second overhang, (iii) eluting the mixture of correct extended ligation product and unreacted first elongation block, (iv) binding the eluate to the solid support carrying a selector oligonucleotide complementary to the second overhang of the second elongation block, i.e. the "selector binding region" thereof, (v) washing away any unreacted first elongation block, (vi) eluting the purified correct extended ligation product of first and second elongation block.

In step a) of said method a first at least partially double-stranded oligonucleotide is provided. Said oligonucleotide comprises a first and a second single-stranded overhang. It is within the present invention that said oligonucleotide can be either formed of a single oligonucleotide, whereby the double-stranded stretch thereof is formed by a part of the oligonucleotide folded back onto another part of the oligonucleotide, or of two or several oligonucleotides. In the latter case, it is sufficient that the double-stranded stretch of said oligonucleotide is formed, mostly irrespective of how many individual oligonucleotides are involved in the reaction. However, it is preferred that said oligonucleotide is formed by two oligonucleotides which are annealed to each other, preferably through Watson-Crick base pairing. It is also within the scope of the present invention that said oligonucleotide is formed by a branched oligonucleotide. Again such branched oligonucleotide is suitable for the use in the method according to the first aspect of the present invention provided that it meets the criteria as defined in step a) of said method. The branched oligonucleotide can either be generated by joining an at least partially double-stranded oligonucleotide and a single-stranded oligonucleotide, or from the two or several single-stranded oligonucleotides base-pairing to form said at least partially double-stranded oligonucleotide having a single-stranded protrusion. The branch point is a nucleotide (preferentially in the loop region) having a chemical moiety which allows for the chemical coupling of a further nucleotide or oligonucleotide thereto. Such chemical moieties which allow for the branching of an oligonucleotide or a nucleic acid, respectively, are known to the ones skilled in the art. Examples for such chemical moieties are amino or carboxy linkers that can be activated with EDC (1-ethyl-3-(3-dimethylaminopropyl) carbodiimide and NHS (N-hydroxylsulfosuccinimide) described by Hoare and Koshland jr. (1967) and Johnsson et al. (1991), respectively. Said first oligonucleotide of step a) is also referred to herein as "left starter", whereas the analogous first oligonucleotide of step b) is also dubbed "right starter".

The first and the second single-stranded overhang of the first at least partially double-stranded oligonucleotide are preferably different in length, with the first overhang preferably being shorter than the second overhang. This is because the first and the second overhang serve different purposes: the first overhang is the place where new nucleotides are added, whereas the second overhang is used to attach the molecule as well as ligation products thereof to a solid support in a specific and reversible fashion.

The length of the first overhang is preferably selected from the group comprising a 1 nucleotide overhang, a 2 nucleotide overhang, a 3 nucleotide overhang, a 4 nucleotide overhang or a 5 nucleotide overhang. As a general rule, the length of the overhang is determined by the restriction enzyme(s) used in the elongation phase, i.e. the first step of the method for the manufacture of a nucleic acid. The nucleotides of the single-stranded overhang plus the adjacent nucleotides distal from the cleavage site of the restriction enzyme specific for the second at least partially oligonucleotide make up the nucleotides that are transferred in each elongation step. The number of transferred nucleotides in turn determines the size of the library of oligo-nucleotides necessary to build every possible sequence. For instance, if six nucleotides are transferred in each step, then a library of $4^6=4096$ different oligonucleotides will be required to represent all possible hexamer permutations.

In the subsequent transposition steps, the pre-assembled elongation blocks are ligated in a pair-wise fashion. Again, the length of the overhangs used to combine the elongation blocks depends on the restriction enzymes used in the transposition phase. Since the restriction enzymes used in the transposition phase will in most cases be different from the ones used in the elongation phase, the length of the overhangs can be different between the two phases. Generally, fragments to be joined in any given step should have the same overhang length.

The length of the second overhang is preferably selected from the group comprising lengths from about 5 to 20 nucleotides, lengths from about 10 to 20 nucleotides, lengths from about 15 to 18 nucleotides, lengths from about 5 to 10 nucleotides and lengths from about 6 to 8 nucleotides. It will be appreciated by the ones in the art that the length depends on the particular sequence and the nature of the constituents of the structure it is to interact with. As is described herein, the function of the second overhang is to immobilise said at least partially double-stranded oligonucleotide to a surface, whereby such surface preferentially carries a nucleic acid which comprises a single-stranded stretch or moiety, which is to interact with the second single-stranded overhang. It will be appreciated by the ones skilled in the art that the length of the overhang and thus of the double-stranded hybrid formed by annealing with the single-stranded oligonucleotide of the surface will be a function of the sequence. A GC-rich double-strand can be shorter compared to a AT-rich double-strand due to the differences in the binding energy shown by GC and AT base pairs respectively. The overall binding energy to be provided by such double-stranded structure will depend on the circumstances under which the thus formed double-stranded hybrid shall be stable. Typically the double-stranded structure has to be stable at a temperature range of 0° C. to 55° C., 15° C. to 50° C. or 25° C. to 45° C. and a salt concentration of 10 mM to 1 M, 25 mM to 500 mM or 50 mM to 300 mM, respectively. Preferably, the double-stranded hybrid has to be stable under the reaction conditions present in any of the other steps of the method according to the present invention, more preferably of steps c) and cb) but must be less stable than the hybrid formed by the at least partially complementary regions of the at least partially double-stranded oligonucleotide of step a) or the two at least partially complementary oligonucleotides that anneal to generate the at least partially double-stranded oligonucleotide of step a). Apart from the GC and AT content of the double-stranded structure, also the kind of nucleotides used or kind of oligonucleotide used, may have an impact on said length of the second overhang of said oligonucleotide. For example, if the second single stranded overhang of said oligonucleotide is made of or is a pyranosyl-RNA, also referred to as pRNA, its length can be significantly reduced. For example, if the length of the second single-stranded overhang of said oligonucleotide is to comprise about 15 to 18 nucleotides to confer a stable immobilisation, using an overhang made of pRNA of about 6 to 8 nucleotides will be sufficient to confer about the same degree of stability. pRNA is, among others, described in Bolli et al. (1997). In pyranosyl-RNA, the normal pentose sugars are replaced by hexose moieties, which increases the binding energy of pRNA hybrids. Yet another alternative could be immobilisation via specific DNA binding proteins or peptides provided that the binding is both selective and reversible using conditions compatible with the integrity of the intermediate products and any materials used in the process.

As used herein, the term "first and second single-stranded overhang" relate to their different function. The first single-stranded overhang is to mediate an interaction with a further oligonucleotide or nucleic acid, preferably through base pairing, more preferably through Watson-Crick base pairing, which is ligated to or with the oligonucleotide providing such single-stranded overhang. Most preferably, this single-stranded overhang is referred to and designed as a short single-stranded overhang, as may also be taken from the design principles for this kind of single-stranded overhang as disclosed herein. As used herein, the second single-stranded overhang can be regarded as modification of the oligonucleotide. The second single-stranded overhang serves to selectively immobilise the oligonucleotide to a surface. Such immobilisation is preferably mediated again through specific base pairing with another oligonucleotide which is coupled to the surface. As the immobilisation must be stable under the reaction conditions, the binding energy generated must be high enough to maintain the base pairing under such conditions. Therefore, the second single-stranded overhang is typically longer than the first single-stranded overhang and is, therefore, also referred to herein as the long, longer or long second single-stranded overhang. In case the binding is mediated through a DNA-protein or DNA-peptide instead of a DNA-DNA interaction, the second single-stranded overhang may also be replaced by a double-stranded region serving the same purpose.

In a preferred embodiment the first at least partially double-stranded oligonucleotide comprises a recognition site for a type II S restriction enzyme.

In step b) a second at least partially double-stranded oligonucleotide is provided. Basically, such second oligonucleotide can be designed in a manner similar to the one of the first oligonucleotide provided in step a), particularly with regard to the design principle of the double-stranded stretch of the oligonucleotide. Thus it can be either formed by folding back of a sequence which is complementary to another sequence of one single oligonucleotide, or by hybridisation of two independent oligonucleotides having complementary stretches. Also, said second oligonucleotide can be a branched oligonucleotide. In a preferred embodiment, the second at least partially double-stranded oligonucleotide is formed of a single oligonucleotide which is folding back on itself thus forming the partially double-stranded structure and providing the single-stranded overhang. Said second oligonucleotide of step b) is also referred to herein as "anchor".

Said second oligonucleotide comprises at least one single-stranded overhang. Such single-stranded overhang is essentially complementary to the single-stranded overhang of the first at least partially double-stranded oligonucleotide of step a). Preferably, the single-stranded overhang is perfectly complementary to the first single-stranded overhang of said first at least partially double-stranded oligonucleotide. Accordingly, the length of the single-stranded overhang of the second oligonucleotide is preferably selected from a 1 nucleotide overhang, a 2 nucleotide overhang, a 3 nucleotide overhang, a 4 nucleotide overhang or a 5 nucleotide overhang. The number of nucleotides of the overhang plus the number of nucleotides distal from the restriction enzyme cleavage site corresponds to the total number of nucleotides transferred in each elongation step, i.e. in each step where the first oligonucleotide is elongated. The length of the overhang in turn depends on the restriction enzymes used in the method for the manufacture of a nucleic acid molecule according to the present invention. In the transposition steps, the length of the overhangs may be different from the length of the overhangs in the elongation reactions.

Said second oligonucleotide also comprises a recognition site for a type IIS restriction enzyme which must be different from the recognition site for the type IIS restriction enzyme present in said first oligonucleotide of step a). As in any of the methods of combinatorial nucleic acid synthesis described herein, the kind of restriction enzyme used and the number of variable nucleotides distal of its cleavage site define the number of nucleotides which are cut off from said second oligonucleotide and transferred to the first oligonucleotide.

Further, said second oligonucleotide comprises a modification which allows for the immobilisation of said second oligonucleotide or any other molecule of which said second oligonucleotide forms part or is a moiety of. In principle, such modification can be a nucleic acid sequence which allows for the immobilisation onto a surface, whereby the surface comprises a nucleic acid which allows for the specific interaction with the modification forming part of the second oligonucleotide. Preferably, such interaction is mediated through base pairing. The length of such modification consisting of a stretch of nucleotides depends on the kind of nucleotides used and the reaction conditions under which such base paring has to be maintained. Here, the same design principles and considerations are applicable as discussed in connection with the second single-stranded overhang of the first oligonucleotide of step a) of the method according to the first aspect of the present invention. Apart from a nucleic acid forming the modification, it is even more preferred to have a modification which is part of a specific interaction pair such as biotin and avidine, streptavidine, extravidine and any mutant or derivative thereof, including artificial biotin binding sites. Further specific interaction pairs include, however are not limited thereto, FITC—anti-FITC antibodies (Serke and Pachmann, 1988) and digoxigenin—anti-digoxigenin antibodies (Kessler et al., 1990).

In a preferred embodiment said second oligonucleotide is part of a library. The members of the library share a design such as essentially described in international patent applications WO 00/75368 and international patent application PCT/EP03/11551, respectively. Thus the members of the library differ in the nucleotides to be transferred from said second oligonucleotide of step b) to said first oligonucleotide of step a) with the other elements of the individual second oligonucleotide preferably being the same as those of the other members of the library.

In step c) of the method for the manufacture of a nucleic acids molecule according to the first aspect of the present invention, said first and said second oligonucleotide are ligated. The ligation reaction is preferably performed in solution, whereby neither said first nor said second oligonucleotide are immobilised to any surface. The reaction conditions for such ligation reaction as well as suitable ligases are known to the ones skilled in the art (Wu and Wallace, 1989).

The ligation reaction is driven by the complementarity of the first single-stranded overhang of said first oligonucleotide and the single-stranded overhang of said second oligonucleotide. To further shift the reaction to the reaction product, an excess of the second oligonucleotide is used. The second single-stranded overhang of said first oligonucleotide is not involved in this ligation process. This can be ensured by designing the second single-stranded overhang such that it cannot be ligated to the single-stranded overhang of any of said second oligonucleotides brought into contact with said first oligonucleotide of step a), which can simply be achieved by using oligonucleotides that possess a 5' hydroxyl group in place of the 5' phosphate. The ligation product preferably comprises one single-stranded overhang only which corresponds to the second single-stranded overhang of said first oligonucleotide of step a). It is, however, also within the present invention that the ligation product comprises a second single-stranded overhang. Such second single-stranded overhang exists when said second oligonucleotide of step b) comprises not only one but a second single-stranded overhang which is preferably the one used as modification and thus for the immobilisation of said second oligonucleotide.

The ligation product obtained in step c) is also referred to herein as the first ligation product. This applies also to a situation when the sequence of steps of the method for the manufacture of a nucleic acid according to the first aspect of the present invention is repeated. In so far, the first ligation product is a ligation product which is generated upon the ligation of a first oligonucleotide having the characteristics of the first oligonucleotide of step a) with any second oligonucleotide having the characteristics of the second oligonucleotide of step b).

In preferred embodiments the first ligation product is immobilised through the modification introduced into the first ligation product through said second oligonucleotide. The immobilisation can occur in the same reaction vessel in which the ligation reaction took place, particularly if the reaction conditions can be adjusted such that during the ligation process no binding of said second oligonucleotide occurs. In a preferred embodiment, however, the ligation reaction is transferred into a different vessel after the ligation reaction has occurred. The different reaction vessel comprises a surface which allows for a specific interaction with the single-stranded overhang of the first ligation product. Said single-straded overhang of the first ligation product preferably corresponds to the second single-stranded overhang of said first oligonucleotide of step a). Preferably such different reaction vessel comprises a single-stranded oligonucleotide which is immobilised to the vessel's surface and essentially complementary to the single-stranded overhang of the first ligation product. This immobilisation step is also referred to herein as step ca) which follows step c) but precedes step d). The other components of the ligation reaction are washed away with the immobilised first reaction product remaining immobilised. This washing step is also referred to herein as step cb).

In a subsequent step the immobilised first reaction product is de-immobilised, i.e. released from the surface. This constitutes step cc) which follows step c), ca) and cb), respectively, and precedes step d). By immobilising, washing and subsequently releasing the first ligation product, the thus obtained first ligation product is essentially pure and free of most, not to say all, starting materials of the ligation reaction as well as side products such as unligated anchor. By using an excess of the second oligonucleotide of step b), also the amount of unreacted first oligonucleotide of step a) should be minimal.

In step d) of the method for the manufacture of a nucleic acid according to the first aspect of the present invention, the first ligation product, which is preferably a purified first ligation product, is cut by the second type IIS restriction enzyme. Preferably this reaction is carried out in solution, i.e. the ligation product is not immobilised to any surface. In doing so two molecules are generated from the first ligation product. A first product is an elongated first at least partially double-stranded oligonucleotide of step a), and a second product is a truncated second at least partially double-stranded oligonucleotide of step b). Said first product corresponds to the said first oligonucleotide of step a) but now comprises at either strand those nucleotides which were cleaved off from said second oligonucleotide of step b) by the second type IIS restriction enzyme. Due to the mode of action of this restriction enzyme also the elongated first at least partially double-stranded oligonucleotide has a first and a second single-stranded overhang. The first single-stranded overhang results from the transfer of the nucleotides form said second oligonucleotide of step b). Its length is determined by the kind of type IIS restriction enzyme used and the number of nucleotides distal to the cleavage site of this enzyme, its sequence by the sequence of said second oligonucleotide of step b) extending beyond the cleavage site of said second type IIS restriction enzyme. This elongated first at least partially double-stranded oligonucleotide can be used, preferably after some purification steps, as a first oligonucleotide of and in a further step a). The second single-stranded overhang is the one introduced into the first ligation product by the first oligonucleotide according to step a). The truncated second at least partially double-stranded oligonucleotide which is formed by cutting the first ligation product by the type IIS restriction enzyme the recognition site of which is part of the second oligonucleotide of step b), corresponds to the second oligonucleotide of step b), except that due to the mode of action of the type IIS restriction enzymes used, those nucleotides extending beyond the cleavage site of said type IIS restriction enzyme have been transferred to said first oligonucleotide of step a) via ligation to the second oligonucleotide of step b) and subsequent cleavage with the outside cutter specific for the second oligonucleotide, i.e. the second type IIS restriction enzyme. Otherwise the truncated second at least partially double-stranded oligonucleotide corresponds to the second at least partially double-stranded oligonucleotide of step b).

In step e) of the method for the manufacture of a nucleic acid molecule according to the first aspect of the present invention, the elongated first at least partially double-stranded oligonucleotide created in step d) is purified. In this purification process the elongated first at least partially double-stranded oligonucleotide is freed from the other components of the restriction reaction and ligation reaction, respectively, particularly from unreacted second oligonucleotide of step b), uncut first ligation product and truncated second at least partially double-stranded oligonucleotide. This is done by providing a surface which comprises an interaction partner of the modification present in said second oligonucleotide and any molecule comprising said second oligonucleotide. The interaction partner interacts with the modification and attaches any compound having such modification to the surface. Such compounds are in particular the unreacted second oligonucleotide of step b), the uncut first ligation product and the truncated second at least partially double-stranded oligonucleotide.

The thus obtained elongated first at least partially double-stranded oligonucleotide can then be transferred into a different reaction vessel. Such different reaction vessel is free of any interaction partner of the second single-stranded overhang which is used for the immobilisation of said elongated first at least partially double-stranded oligonucleotide thus allowing said elongated first oligonucleotide to be kept in solution. Said elongated first at least partially double-stranded oligonucleotide can subsequently be used as the first at least partially double-stranded oligonucleotide in step a) of the method for the manufacture of a nucleic acid according to the first aspect of the present invention. Steps a) to e) can be repeated in preferred embodiments several times. Preferably, the steps a) to e) are repeated zero to ten times, more preferably three to six times. Any second at least partially double-stranded oligonucleotide provided in the repetition of steps a) to e) is also referred to herein as further at least double-stranded oligonucleotide.

The transposition phase.

In the method for the manufacture of a nucleic acid molecule according to the second aspect of the present invention in step a) an elongated first at least partially double-stranded oligonucleotide is provided. Such elongated first at least partially double-stranded oligonucleotide is preferably an elongated first at least partially double-stranded oligonucleotide obtained by the method for the manufacture of a nucleic acid according to the first aspect of the present invention. However, it is not obligatory that the at least partially double-stranded oligonucleotide is produced by such said method.

The first at least partially double-stranded oligonucleotide has a structure which essentially corresponds to the one of the first partially double-stranded oligonucleotide of step a) of the method according to the first aspect of the present invention. In accordance therewith, the first at least partially double-stranded oligonucleotide comprises a first single-stranded overhang, a modification which allows for a specific immobilisation to a surface, whereby the modification is preferably a second single-stranded overhang, a recognition site for a type IIS restriction enzyme and a stretch of consecutive nucleotides which correspond to the nucleic acid to be manufactured or a part thereof.

This first single-stranded overhang is such that it allows hybridisation with another first single-stranded overhang of a second at least partially double-stranded oligonucleotide which is provided in step b) of the method for the manufacture of a nucleic acid according to the second aspect of the present invention. Preferably, the length of the first single-stranded overhang is the same as or designed according to the same principles as the first single-stranded oligonucleotide of step a) of the method according to the first aspect of the present invention.

The second single-stranded overhang is the same as or designed according to the same principles as the first single-stranded oligonucleotide of step a) of the method according to the first aspect of the present invention.

The stretch of consecutive nucleotides which correspond to the nucleic acid to be manufactured or a part thereof are provided in a double stranded form, i.e. both strands of the double-stranded oligonucleotide comprise a number of said nucleotides. The stretch of consecutive nucleotides can be generated by the method according to the first aspect of the present invention, although their manufacture is not limited thereto. Preferably, the number of the consecutive nucleotides on each of the two strands is 3 to 48, preferably 6 to 30 and more preferably 12 to 24 nucleotides. In case the first at least partially double-stranded oligonucleotide is manufactured using the method according to the first aspect of the present invention, this stretch of consecutive nucleotides corresponding to the nucleic acid to be manufactured or a part thereof has been built up by repeating steps a) to e) several times with the second at least partially double-stranded oligonucleotide of step b) of said method according to the first aspect of the present invention using further at least partially double-stranded oligonucleotides as second at least partially double-stranded oligonucleotides in step b), whereby any of the further at least partially double-stranded oligonucleotides provides another group of nucleotides which become part of the nucleic acid to be synthesised finally forming the stretch of consecutive nucleotides corresponding to the nucleic acid to be manufactured or a part thereof.

The recognition site and cleavage site of the first type IIS restriction enzyme is arranged in this elongated first at least partially double-stranded oligonucleotide such that preferably the nucleotides transferred from the second and any further at least partially double-stranded oligonucleotides provided in step b) of the method according to the first aspect of the present invention are cut off, preferably as a contiguous stretch of nucleotides, whereby such stretch of nucleotides is the nucleic acid to be manufactured or a part thereof.

In step b) of the method for the manufacture of a nucleic acid according to the second aspect of the present invention, another oligonucleotide is provided. Such another oligonucleotide is another elongated first at least partially double-stranded oligonucleotide. Said another elongated first at least partially double-stranded oligonucleotide is of the same design as the elongated first at least partially double-sided oligonucleotide provided in step a) of the method for the manufacture of a nucleic acid according to the second aspect of the present invention, but differs therefrom in several regards. First, the second single-stranded overhang is different from the one of the first at least partially double-stranded oligonucleotide provided in step a). The reason for this is to provide a means which allows for the selective immobilisation of the another first at least partially double-stranded oligonucleotide as of step b) compared to the one as of step a). It will be acknowledged that the second single-stranded overhang is one embodiment of a selective immobilisation means which is generally formed by any modification of the oligonucleotide which allows for the selective immobilisation of such oligonucleotide. Second, the another first at least partially double-stranded oligonucleotide as of step b) exhibits a recognition site for a type IIS restriction enzyme which is different from the one of the first at least partially double-stranded oligonucleotide as of step a). This type IIS restriction enzyme is also referred to as second type IIS restriction enzyme. Third, the stretch of consecutive nucleotides which correspond to the nucleic acid to be manufactured or a part thereof, differs from the one of the first at least partially double-stranded oligonucleotide as of step a). Actually, this stretch of consecutive nucleotides represents those nucleotides which are, in the overall sequence of the nucleic acid molecule to be manufactured, either preceding or following the stretch of consecutive nucleotides which correspond to the nucleic acid to be manufactured or a part thereof, of the first at least partially double-stranded oligonucleotide as of step a). In the present case both stretches of consecutive nucleotides are in the same orientation so that their linear ligation immediately results in a larger stretch of consecutive nucleotides which correspond to the nucleic acid to be manufactured or a part thereof.

In principle, the short single-strand overhangs used for ligating the (elongated) at least partially complementary oligonucleotides can be either 5' protruding or 3' recessed, depending on the type of outside cutting restriction enzyme used. The only restriction is that the ends that are to be joined in any given reaction step have to be of the same type. This applies in general to any at least partially double-stranded oligonucleotide described or disclosed herein In step c) of the method for the manufacture of a nucleic acid according to the second aspect of the present invention, the elongated first at least partially double-stranded oligonucleotide as of step a) and the elongated first at least partially double-stranded oligonucleotide as of step b) are ligated. The ligation is performed on the two elongated first at least partially double-stranded oligonucleotides as of step a) and as of step b) which are annealed to each other due to the base pairing of the respective first (short) single-stranded overhangs. The ligation as such is carried out according to standard protocols as described, e.g. also in connection with the ligation step of the method for the manufacture of a nucleic acid according to the first aspect of the present invention. Preferably, both the elongated first at least partially double-stranded oligonucleotide as of step a) and as of step b) are in solution, i.e. are not immobilised to any surface. As used herein, a surface is preferably provided by a solid phase, however, is not limited thereto. The ligation product thus created in step c) is also referred to herein as first extended ligation product or first transposition product.

In step d) of the method for the manufacture of a nucleic acid according to the second aspect of the present invention, the first extended ligation product of step c) is immobilised to a surface. Such immobilisation is a specific immobilisation. Preferably, such immobilisation is mediated by one of the two available second single-stranded overhangs. It is to be acknowledged that the first extended ligation product comprises two different second single-stranded overhangs. One stems from the elongated first at least partially double-stranded oligonucleotide as of step a) and the other one from the elongated first at least partially double-stranded oligonucleotide as of step b). The other single stranded overhangs, i.e. the first single stranded overhang from the elongated first at least partially double-stranded oligonucleotide as of step a) and the first single-stranded overhang from the elongated first at least partially double-stranded oligonucleotide as of step b) are no longer available as they were used to anneal and subsequently ligate said two oligonucleotides. In order to perform an efficient immobilisation, the preceding ligation reaction is carried out under conditions where no immobilisation of any of the educts or of the product can occur. This is typically achieved by carrying out the reaction in a reaction vessel which does not have a surface which allows such immobilisation. For example, the reaction vessel does not exhibit on its surface any oligonucleotide or any nucleic acid which acts as a counterpart, i.e. binding partner, of the second single-stranded oligonucleotide which is responsible for immobilising any of the oligonucleotides provided in steps a) and b), respectively. Alternatively, the ligation reaction is carried out in a reaction vessel which has a surface which would allow immobilisation, however, the reaction conditions are such that immobilisation does not occur. Respective measures are known to the ones skilled in the art and comprise, however are not limited to, carrying out the ligation at such a high temperature at which no immobilisation can occur as the temperature of the reaction is higher than the melting temperature of the double strand formed between the second single-stranded overhang of the educts and product, respectively, and the counterpart on the surface which is preferably a nucleic acid or oligonucleotide which is essentially complementary to the second single-stranded overhang. Still other methods for controlled binding involve the use of selectors and selector binding sequences that have the ability to form intramolecular stem-loop structures the binding energy of which must be lower than the binding energy of the hybrid formed by the selector and the selector binding region. Only when the temperature is raised above the melting point of the intramolecular stem-loop structures or reaction conditions are chosen to destabilise them, will these molecules become available for the formation of intermolecular hybrids provided that the binding energy of these intermolecular hybrids is higher than the binding energy of the intramolecular hybrids.

In a subsequent optional step e) the immobilised first extended ligation product is washed, whereby any unligated elongated first at least partially double-stranded oligonucleotide as of step a) is removed, if the immobilisation of the first extended ligation product is done via the second single-stranded overhang of the elongated first at least partially double-stranded oligonucleotide as of step b). If the immobilisation of the first extended ligation product is done via the second single-stranded overhang of the elongated first at least partially double-stranded oligonucleotide as of step a), then the unligated elongated first at least partially double-stranded oligonucleotide as of step b) is removed. In so far, step e) is a purification step to remove at least some of the contaminants of the ligation reaction from the reaction product which allows to increase the efficacy of subsequent reaction steps and thus the accuracy of the nucleic acid to be manufactured in terms of yield and sequence fidelity.

Step f) of the method for the manufacture of a nucleic acid according to the second aspect of the present invention releases the immobilised first extended ligation product. Such release can be effected by adjusting the reaction conditions so that the first extended ligation product is eluted from the surface. In case, as is preferred herein, the immobilisation is mediated through a second single-stranded overhang, suitable measures comprise increasing the temperature of the reaction above the melting temperature of the double-strand formed between said second single-stranded overhang and its counterpart on the surface, decreasing the salt concentration so that the double-strand formed between said second single-stranded overhang and its counterpart on the surface is broken down, and the use of a competitor to the binding of the second single-stranded overhang and its counterpart on the surface. If not indicated to the contrary, any of these measures may be used to interfere and thus loosen the binding of any oligonucleotide to a surface.

As, however, apart from the first extended ligation product any of the staring material having a second single stranded overhang which allows to specifically bind to the surface, will also be immobilised during the immobilisation step d) and, consequently, be also released from the surface in the course of step f), the first extended ligation products needs a further purification step. This further purification is done by providing a surface which allows for the specific binding of the first extended ligation product via the other second single-stranded overhang contained in the first extended ligation product. Washing of the thus immobilised first extended ligation product removes any of the non-immobilised oligonucleotides, particularly the unreacted elongated first at least partially complementary oligonucleotides not yet removed in the preceding steps. Upon release of the first extended ligation product, such first extended ligation product is essentially pure.

The steps described above are repeated or are preferably carried out in parallel with other sets of elongated first at least partially double-stranded oligonucleotides of step a) and step b) of the method for the manufacture of a nucleic acid according to the second aspect of the present invention. As described above, any of the oligonucleotides of step a) and step b) of the method according to the first and second aspect of the present invention, comprises a stretch of consecutive nucleotides which correspond to the nucleic acid to be manufactured or a part therefrom. This stretch of consecutive nucleotides is defined by the following procedure. First, the nucleic acid to be manufactured is dissected into a first and a second series of smaller fragments. Such fragments typically comprise about 6 to 30 base pairs such that adjacent fragments belong to the respective other series of fragments. Second, these smaller fragments are synthesised, typically in parallel reactions, whereby the orientation of synthesis of these smaller fragments can either be the same of the opposite as the orientation of these fragments in the nucleic acid to be manufactured, preferably a DNA. Third, these smaller fragments or intermediates are joined in successive pair wise ligations so as to create larger and larger intermediates and finally the complete nucleic acid to be manufactured. Preferably, the dissection of a given sequence, i.e. the sequence of the nucleic acid to be manufactured, into said smaller fragments is done with a computer program to determine the optimal synthesis strategy with a minimal number of identical or self-complementary overhangs or to avoid the presence of those internal restriction sites that are used in the assembly process, whereby this term refers to both the elongation and the transposition phase. Internal restriction sites that are only used during the elongation phase may be tolerated if they can be placed such that they span the ends of adjacent elongation products. As used herein, these smaller fragments correspond to the or any part of the nucleic acid to be manufactured as contained in the elongated first at least partially double-stranded oligonucleotides. The successive pair wise ligations correspond to the transposition steps as described herein as well as in international patent applications WO 00/75368 and PCT/EP 03/11551, the disclosure of which is incorporated herein by reference.

The steps disclosed herein for the method according to the second aspect of the present invention are repeated with a second set of an elongated first at least partially double-stranded oligonucleotide used in step a) and another elongated first set of at least partially double-stranded oligonucleotide used in step b). Preferably this sequence of reaction steps is carried out independently from the reactions performed on the first set of an elongated first at least partially double-stranded oligonucleotide used in step a) and another elongated first set of at least partially double-stranded oligonucleotide used in step b). Even more preferably, such reaction or sequence of reaction steps is carried out in parallel to those reaction steps related to the first set of oligonucleotides. This second set of oligonucleotides differs from the first one in so far as the stretches of consecutive nucleotides which correspond to the nucleic acid to be manufactured or a part thereof, are a third and fourth part of such nucleic acid. As in the case of the first and second part provided by the first set of oligonucleotides used in step a) and b), respectively, the third part and the fourth part are adjacent parts of the nucleic acid to be manufactured. This means that their orientation is the same and corresponds to the one as found in the nucleic acid to be manufactured. The same applies also to the second and third part of the nucleic acid to be manufactured. The elongated first at least partially double-stranded oligonucleotide and the another elongated first at least partially double-stranded oligonucleotide forming the second set of oligonucleotides in step a) and b), respectively, also have recognition sites for different type IIS restriction enzymes which are referred to herein as the third and the fourth type IIS restriction enzymes. Preferably, the second and the third type IIS restriction enzymes are different but both provide for single-stranded overhangs having the same length so as to allow for an annealing of two oligonucleotides both being cut by one of said two restriction enzymes, provided that the sequence of the overhangs are at least essentially complementary, and subsequent ligation in the course of the various steps in the methods according to the present invention. In a more preferred embodiment the first and fourth type IIS restriction enzyme are different but provide for single-stranded overhangs having the same length so as to allow for an annealing of two oligonucleotides both being cut by one of said two restriction enzymes, provided that the sequence of the overhangs are at least essentially complementary, and subsequent ligation in the course of the various steps in the methods according to the present invention. The ligation product formed by the two oligonucleotides of the second set of oligonucleotides is also referred to as second extended ligation product or second transposition product.

The second extended ligation product is treated similarly to the first extended ligation product, particularly in terms of purification.

In the method for the synthesis of a nucleic acid according to the second aspect of the present invention, the first extended ligation product is cut by the second type II restriction enzyme as step j). By cleaving the first extended ligation product using the second type II restriction enzyme basically two products are generated. First, a cut first extended ligation product to which the nucleotides synthesised in the elongation phase are attached and, second, an at least partially double-stranded DNA fragment essentially corresponding to the last at least partially double-stranded oligonucleotide used in the generation of the elongated at least partially double-stranded oligonucleotide of step b). This results from the fact that the another elongated first at least partially double-stranded oligonucleotide used in step b) of the method according to the second aspect of the present invention comprises the recognition site used in the previous step and the restriction enzyme cuts off any nucleotide beyond the cleavage site of the restriction enzyme. Thus any of the nucleotides beyond said cleavage site are transferred to the cut first extended ligation product such that it now comprises the stretch of consecutive nucleotides which correspond to the nucleic acid to be manufactured or a part thereof provided by both the elongated first at least partially double-stranded oligonucleotide as of step a) of the method according to the second aspect of the present invention, and the another elongated first at least partially double-stranded oligonucleotide as of step b) of the method according to the second aspect of the present invention.

The cut first extended ligation product is subsequently purified using the same approach as described in connection with other purification steps herein. More particularly, the purification step removes any uncut first extended ligation product and the second reaction product besides the cut first extended ligation product, i.e. the at least partially double-stranded oligonucleotide essentially corresponding to the first at least partially double-stranded oligonucleotide used in the generation of the elongated at least partially double-stranded oligonucleotide of step a) of the method according to the first aspect of the present invention. Both reaction products have the second single-stranded overhang which stems from the another elongated first at least partially double-stranded oligonucleotide as of step b) of the method according to the second aspect of the present invention. By providing a surface which allows for a specific interaction of this second single-stranded overhang, such as a single stranded oligonucleotide or nucleic acid being essentially complementary to the second single-stranded overhang, these by-products can be removed and thus the cut first extended ligation product be purified. In a preferred embodiment, the thus purified cut first extended ligation product is used for further ligation steps, more preferably after transfer into a different reaction vessel which allows the cut first extended ligation product to be in solution, i.e. not being immobilised.

The same steps as described for the first extended ligation product are performed on the second extended ligation product. However, the second extended ligation product is cleaved by the third type IIS restriction enzyme providing a cut second extended ligation product. Such cut second extended ligation product is, in preferred embodiments subject to a purification reaction which allows the removal of the other reaction products of the cleavage reaction using the third type IIS restriction enzyme, as well as uncut second extended ligation product which both would interfere with subsequent reaction steps, particularly with further ligation steps.

In a subsequent step, both the cut first extended ligation product and the cut second extended ligation product are ligated creating a further ligation product which is also referred to herein as second level transposition product or as T2 or T2 product. This T2 product is assembled using the single-stranded overhangs identical in length generated by the second and third outside cutting restriction endonucleases, i.e. the second and third type IIS restriction enzyme. Efficient ligation is facilitated by single-stranded overhangs that are at least essentially complementary to each other, preferably perfectly complementary to each other which can be ensured by a proper design of the fragments, i.e. the stretch of consecutive nucleotides which corresponds to the nucleic acid to be manufactured or a part thereof. Again, the length of the stretch of consecutive nucleotides which corresponds to the nucleic acid to be manufactured or a part thereof, now contained in the T2 product consists of the respective stretches contained in the cut first extended ligation product and the cut second extended ligation product. Also, the T2 product comprises two second single-stranded overhangs. These two second single-stranded overhangs are different from each other and allow each for a selective immobilisation of the T2 product at either end, whereby the second single-stranded overhangs stem from the elongated first at least partially double-stranded oligonucleotides of step a) and step b), respectively, of the method according to the second aspect of the present invention.

It is within the method for the manufacture of a nucleic acid molecule according to the second aspect of the present invention that the T2 product may be used as an elongated first at least partially double-stranded oligonucleotide of step a) and step b), respectively, of the method according to the second aspect of the present invention.

Type IIS restriction enzymes as used in connection with any aspect of the present invention are preferably outside cutters, i.e. restriction enzymes which are characterised by the fact that they interact with two discrete sites of a double-stranded DNA. One of said two sites is the non-palindromic recognition site for said restriction enzyme which typically has a length of four to seven base pairs. The other site is the cleavage site which is typically zero to twenty base pairs apart from the recognition site. The recognition sites of the restriction enzymes are either completely or partially asymmetric. It is a preferred feature of outside cutters that their cleavage site is beyond, i.e. outside their recognition site. As used herein in preferred embodiments, the at least partially double-stranded oligonucleotides comprise a recognition site for one of at least two different outside cutters which may be either completely or partially part of the oligonucleotide. To allow for the proper functioning of the method according to the present invention, the type IIS restriction enzyme the recognition site of which is contained in the first and further at least partially double-stranded oligonucleotide, respectively, and which is also referred to herein as the first type IIS restriction enzyme, respectively, and the type IIS restriction enzyme the recognition site of which is contained in the second at least partially double-stranded oligonucleotide and which is also referred to herein as the second or further type IIS restriction enzyme, must be different.

The following table provides some possible combinations of recognition sequences of type IIS restriction enzymes.

cate the incubation temperatures used for each of the pairs. The isoschizomers of these enzymes (BsaI: Bso31, Eco31I; BsmBI: Esp3I; BbsI: BpiI, BpuAI; BspMI: Acc36I; BsrDI: Bse3DI, BseMI; BmrI: BfiI) are potential alternatives.

It is within a preferred embodiment of any aspect of the present invention that any of the second and further oligonucleotides having an at least partially double-stranded structure, a single-stranded overhang and a recognition site for a type IIS restriction enzyme generally comprises at least one nucleotide which can be cleaved off from the oligonucleotide upon digestion with said restriction enzyme. More preferably, such nucleotide(s) are part of a nucleic acid to be manufactured.

The method according to the third aspect of the present invention is also referred to as semi-half inverted transposition (S-HIT). S-HIT is a transposition method which can be used in any of the methods and processes described in inter-

| Recognition site for first oligonucleotide | Recognition site for second oligonucleotide |
|---|---|
| CGTCTCN^NNNN_(Esp3I, BsmBI) (SEQ. ID. No 1) | GGTCTCN^NNN_(BsaI, Eco31I . . . ) |
| GGTCTCN^NNNN_(BSaI, Eco3 11, . . . ) (SEQ. ID. No. 2) | CGTCTCN^NNNN_(Esp3I, BsmBI) |
| GAAGACNN^NNNN_(BbsI, BpiI . . . ) (SEQ. ID. No. 3) | ACCTGCNNNN^NNNN_(BspMI, Acc36I) |
| ACCTGCNNNN^NNNN_(BspMI, Acc36I) (SEQ. ID.No. 4) | GAAGACNN^NNNN_(BbsI, BpiI . . . ) |
| GCAGTG_NN^(BtsI) (SEQ. ID. No. 5) | GCAATG_NN^(BsrDI, Bse3DI, . . . ) |
| GCAATG_NN^(BsrDI, Bse3DI, . . . ) (SEQ. ID. No. 6) | GCAGTG_NN^(BtsI) |
| GTATCCNNNNN_N^(BciVI, BfuI) (SEQ. ID. No. 7) | ACTGGGNNNN_N^(BfiI, BmrI) |
| ACTGGGNNNN_N^(BfiI, BmrI) (SEQ. ID. No. 8) | GTATCCNNNNN_N^(BciVI, Bful) |
| GGCGGANNNNNNNNN_NN^(EciI) (SEQ. ID. No. 9) | GAGGANNNNNNNN_NN^(BseRI) |
| GAGGAGNNNNNNNN_NN^(BseRI) (SEQ. ID. No. 10) | GGCGGANNNNNNNNN_NN^(EciI) |
| CACCTGCNNNN^NNNN_(AarI) (SEQ. ID. No. 11) | CAGCTCNNNNNNN^NNNN_(AceIII) |
| CAGCTCNNNNNNN^NNNN_(AceIII) (SEQ. ID. No. 12) | CACCTGCNNNN^NNNN_(AarI) |
| GCTCTTCN^NNN_(SapI) (SEQ. ID. No. 13) | (adapter linker necessary) |
| CTCTTCN^NNN_(Eam1104I, Ksp632I, EarI) (SEQ. ID. No. 14) | (adapter linker necessary) | whereby
N = any of the nucleotides A, G, C or T;
^is the cleavage site in the upper strand, i. e. 5'->3' from left to right, and
_the cleavage site in the lower strand, i. e. 5 '->3' from right to left.

Preferred combinations of the first and second (and further) type IIS restriction enzyme to be used in connection with the present invention are Eco31I/Esp3I (37° C.), BsaI/BsmBI (50° C.), BsmBI/BsaI (55° C.), BbsI/BspMI (37° C.), BspMI/BbsI (37° C.) BsrDI/BtsI (65° C.), BtsI/BsrDI (37° C.), BciVI/Bmrl (37° C.), AarI/AceIII (37° C.), EciI/BseRI (37° C.) und BmrI/BciVI (37° C.). Temperatures in brackets indinational patent applications PCT/DE 00/01863, international patent application PCT/EP 02/13154 and international patent application PCT/EP 03/11551, which are also known as Sloning processes and comprise a first phase in which so-called elongation blocks are generated, and a second phase which is referred to as transposition or transposition phase, where the elongation blocks are successively ligated in a pair wise fashion as described herein thus forming longer and longer transposition products. Throughout the text such elongation blocks are more generically also referred to as "ligation products", thereby expressing that it is irrelevant by which procedure they have been produced. More particularly the method according to the third aspect of the present invention is another manifestation of the principles underlying the so-called semi-inverted transposition as described in international patent application PCT/EP 03/11551, which is also referred to as SIT.

In both methods, i.e. the SIT, and S-HIT method, ligation products are provided as a starting point. Each such ligation product basically consists of a first oligonucleotide moiety comprising a recognition site for a first type IIS restriction enzyme, a second oligonucleotide moiety comprising a recognition site for a second type IIS restriction enzyme and a third oligonucleotide moiety in between, whereby the third oligonucleotide moiety is a part of the nucleic acid molecule to be manufactured. Preferably, the second oligonucleotide moiety additionally comprises a modification. This modification allows for a specific binding of the second oligonucleotide moiety or any molecule which comprises such second oligonucleotide moiety such as the ligation product. In a preferred embodiment, the first and the second type IIS restriction enzymes each generate upon cleavage of the respective oligonucleotide an overhang, whereby more preferably the overhang generated by the first type IIS restriction enzyme has a length which is different from the length of the overhang generated by the second type IIS restriction enzyme.

As used herein, the expression 'that the modification allows for a specific binding' preferably means that the binding occurs only under certain circumstances or reaction conditions but avoids an unintended binding of the molecule comprising such modification. Because of this, depending on the reaction conditions or circumstances existing or realized, the modification comprising molecule can bind to an interaction partner or not. Preferably such binding partner is attached to a surface, more preferably a solid phase. Any modification which provides for these characteristics can be used as a modification which allows for a specific binding. This kind of modification can be a modification as described herein or in any of international patent applications PCT/DE 00/01863, PCT/EP 02/13154 or international patent application PCT/FP 03/11551.

The restriction enzyme can in principle be any type IIS restriction enzyme, which cleaves outside of their recognition sequence (such enzymes are also referred to as "outside cutters"), preferably those described herein.

The first oligonucleotide moiety of a ligation product is an at least partially double-stranded oligonucleotide which comprises the recognition site of the respective type IIS restriction enzyme. The first oligonucleotide moiety may also comprise further nucleotides on each of the two strands forming the at least partially double-stranded structure of the first oligonucleotide moiety. In a preferred embodiment, the double stranded structure comprises a moiety which links both strands forming the double stranded structure. Moieties which can form such links, are known in the art and, e.g., described in international patent applications PCT/DE 00/01863, PCT/EP 02/13154 and PCT/EP 03/11551. More preferably, such link is formed by a sequence of nucleotides. The sequence of the at least partially double-stranded oligonucleotide upstream of the recognition site is of less importance as long as the structural requirements are met. Preferably, the sequence shall comprise nucleotides which, particularly upon hybridisation forming the double-stranded structure, form a stable double strand with a minimum number of base pairs. Therefore, GC-rich sequences forming the double-stranded structure are particularly preferred. The sequence downstream of the recognition site but upstream of the cleavage site may also be chosen at will as long as one eschews to create further recognition sites for the restriction enzymes used in the process. Again, GC base pairs are preferred at these positions because they contribute to a higher stability of the double strand. Any sequence downstream of the cleavage site is pre-determined by the nucleic acid to be made.

In a preferred embodiment, the first oligonucleotide moiety is a splinker molecule or an anchor molecule as defined in any of international patent applications PCT/DE 00/01863, PCT/EP 02/13154 and PCT/EP 03/11551.

The second oligonucleotide moiety has a design very similar to the first oligonucleotide moiety but comprises a modification, which allows for specific binding to a solid phase. It is crucial that the first and the second oligonucleotide moiety comprise recognition sites for different type IIS restriction enzymes so that each recognition site is recognised by only one of the restriction enzymes used.

The third oligonucleotide moiety corresponds to a part of the nucleic acid to be manufactured. If one theoretically dissects the complete ligation product into separate moieties at the cleavage sites of the type IIS restriction enzymes the recognition sites of which are contained in said ligation product, both the first and the second oligonucleotide moiety provide for a single stranded overhang, the third oligonucleotide moiety comprises an overhang at each of its ends. The length and location of the overhang depends on the type IIS restriction enzymes the recognition sites of which are provided by the first and the second oligonucleotide moiety. The cleavage sites of these enzymes are placed to allow the exact excision of the part of the nucleic acid to be manufactured from the ligation product or any molecules where the ligation product is either partially or completely incorporated.

It will be understood by those skilled in the art that any of the ligation products used in the method according to the third aspect of the present invention is preferably the ligation product of two elongation products as described, among others, in international patent applications PCT/DE 00/01863, PCT/EP 02/13154 or PCT/EP 03/11551. In such embodiment, the first and the second oligonucleotide moiety correspond to members the library used for the generation of the elongation blocks as used in the Sloning processes. These elongation blocks are generated by a sequence of transfer steps of a multitude of nucleotides from an at least partially double-stranded oligonucleotide having at least one overhang at one end and being a member of a library of at least partially double-stranded oligonucleotides which preferably share a common design but differ in a sequence of nucleotides which can be cleaved off by the type IIS restriction enzyme. Thus if at least one but preferably several members of said library, acting as a donating oligonucleotide, are sequentially ligated to another oligonucleotide having an at least a partially double-stranded structure and an overhang which is complementary to the member of said library acting as an acceptor oligonucleotide, an elongation block or ligation product as used herein is generated.

It is to be understood that the length of the third oligonucleotide moiety contained in the ligation product depends, if such ligation product is the result of a process for generating elongation blocks as described herein, on the number of transfer steps in which the overhang distal from the cleavage site of the type IIS restriction enzyme is transferred from a donating oligonucleotide, i.e. preferably a member of the afore-described library, to an acceptor oligonucleotide. In case the ligation products are generated by the Sloning process, the length of the third oligonucleotide moiety is determined by the number of elongation steps and the number of nucleotides added in each step. In preferred embodiments of the present invention the length of the third oligonucleotide moiety is such that the double-stranded structure of this moiety is stable under the reaction conditions used. In an even more preferred embodiment the length of the third oligonucleotide moiety in terms of base pairs forming a double-stranded structure is any number from 17 to 38 base pairs, i.e. 17, 18, 19, 20, 21, 22, 23, 24, 25, 26, 27, 28, 29, 30, 31, 32, 33, 34, 35, 36, 37 and 38 base pairs. In this context, said third oligonucleotide moiety is part of a first order transposition product. However as the third oligonucleotide moiety preferably comprises an overhang, preferably at both ends of the double stranded structure comprised by the third oligonucleotide moiety, each strand of the third oligonucleotide moiety comprises a single-stranded overhang of any number from 1 to 5 nucleotides. In a preferred embodiment of the method according to the present invention, the third oligonucleotide moiety corresponds to the second cut ligation product.

In a preferred embodiment of the method according to the third aspect of the present invention the design of the ligation product is as follows in terms of orientation. The double-stranded ligation product is depicted typically in a form wherein the upper strand is written 5'->3' from left to right and the complementary lower strand 5'->3' from right to left, following general conventions.

It is to be understood that in the method according to the third aspect of the present invention for realizing the first transposition step a total of four different ligation products are provided. Said four different ligation products generally differ from each other in the third oligonucleotide moiety which is each a part of the nucleic acid molecule to be manufactured and in at least one recognition site. Basically, the first ligation product thus provides for a first part of the nucleic acid molecule to be manufactured, the second ligation product thus provides for a second part of the nucleic acid molecule to be manufactured, the third ligation product thus provides for a third part of the nucleic acid molecule to be manufactured, and the fourth ligation product thus provides for a fourth part of the nucleic acid molecule to be manufactured.

Said first, second, third and fourth part of the nucleic acid molecule to be manufactured are parts which are arranged consecutively in the nucleic acid molecule to be manufactured. The difference between the SIT procedure as described in international patent application PCT/EP 03/11551 and the S-HIT procedure according to the present invention resides in the arrangement of the parts within the ligation products. According to the SIT procedure, the sequence of the third oligonucleotide moiety of the first ligation product corresponds to the sequence of the first part of the nucleic acid to be manufactured, whereas the sequence of the third oligonucleotide moiety of the second ligation product corresponds to the reverse complement of the second part of the nucleic acid to be manufactured. Accordingly, the sequence of the third oligonucleotide moiety of the third ligation product corresponds to the sequence of the third part of the nucleic acid to be manufactured, whereas the sequence of the third oligonucleotide moiety of the fourth ligation product corresponds to the reverse complement of the fourth part of the nucleic acid to be manufactured. As used herein the term 'reverse complement of a part of the sequence to be manufactured' means that the sequence is in reverse orientation compared to the target sequence of the nucleic acid molecule to be manufactured. This means that the 5' terminal nucleotide of the target sequence is the 3' terminal nucleotide of the reverse complement and the 3' terminal nucleotide of the target sequence is the 5' terminal nucleotide of the reverse complement. In other words the reverse complement can be generated by reading the target sequence from the 5' end to the 3' end on the complementary strand. Therefore, the third oligonucleotide moiety of the second ligation product comprises the second part of the nucleic acid to be manufactured in its reverse complement form, i.e. the sequence actually displayed in the third oligonucleotide moiety of the second ligation product in the 5'-3' direction is the complementary sequence read in the 5'-3' direction, and the third oligonucleotide moiety of the fourth ligation product comprises the fourth part of the nucleic acid to be manufactured in its reverse complement form.

In contrast to this particular arrangement of the various parts of the nucleic acid to be manufactured in the SIT procedure, the parts of the nucleic acid to be manufactured in the S-HIT procedure are arranged in a different manner. More particularly, the first and the second part of the nucleic acid to be manufactured contained in the third oligonucleotide moiety of the first and the second ligation product are arranged in the same orientation, and the third and the fourth part of the nucleic acid to be manufactured contained in the third oligonucleotide moiety of the third and the fourth ligation product are arranged in the same orientation, whereby either the third oligonucleotide moiety of the first and the second ligation product correspond to the sequence of the first and the second part of the nucleic acid to be manufactured and the third oligonucleotide moiety of the third and the fourth ligation product correspond to the reverse complement of the third and fourth part of the nucleic acid to be manufactured, or the third oligonucleotide moiety of the first and the second ligation product correspond to the reverse complement of the first and the second part of the nucleic acid to be manufactured and the third oligonucleotide moiety of the third and the fourth ligation product correspond to the sequence of the third and fourth part of the nucleic acid to be manufactured.

This change in the relative orientation of the various parts of the nucleic acid to be manufactured has a considerable impact on the performance of the transposition procedure. The concept underlying both the SIT procedure and the S-HIT procedure is to flip the orientation of the synthesised sequences in order to provide unique overhangs for the ligations in the transposition phase in that only those molecules have matching ends that have been cut in the previous step. As a result of this procedure, the third oligonucleotide moiety of one of the ligation products is released by cutting the ligation product with both type IIS restriction enzymes the recognition sites of which are contained in the ligation product. Due to the above described orientation of the various parts of the nucleic acid to be manufactured, every other third oligonucleotide moiety is flipped in the first transposition step in the SIT procedure, whereas in the first transposition step of the S-HIT procedure all third oligonucleotide moieties initially retain the orientation of the ligation products they were part of. In the second and all subsequent steps, the orientation of the third oligonucleotide moieties of every other transposition intermediate is switched in both procedures alike.

Although the SIT procedure is a very useful transposition method, the S-IT procedure offers in some regards advantages over the SIT procedure. A prominent advantage of the S-HIT procedure compared to the SIT procedure is the fact that the first order transposition products retain their protecting end structures, i.e. either the first or the second oligonucleotide moiety. This effectively prevents that the complementary strands of the third oligonucleotide moiety come apart. In the second transposition step, the length of the third oligonucleotide moiety released by cleaving a ligation product with both restriction enzymes the recognition sites of which are contained in the ligation product thus generating the cut second transposition product as used herein, is considerable longer and thus less likely to become denatured. This reduced denaturation of the double-stranded structure significantly increases the efficacy of any reaction step during subsequent transposition cycles.

The method for the manufacture of a nucleic acid molecule according to the fourth aspect of the present invention is also referred to herein as alternative semi inverted transposition (ASIT). ASIT is a transposition method which can be used in any of the methods and processes described in international patent applications PCT/DE00/01863, PCT/EP02/13154 and PCT/EP03/11551 which are also known as Sloning processes and comprise a first phase where so-called elongation blocks are generated and a second phase which is referred to as transposition or transposition phase, where the building blocks are ligated in a pair-wise fashion as described herein. Similar to the semi-half inverted transposition method described herein, the ASIT procedure is another manifestation of the principles underlying the so-called semi inverted transposition as described in international patent application PCT/EP03/11551 and herein. In view of this, the basic design of first, second, third and fourth ligation process is essentially the same as described in connection with the semi-inverted transposition procedure. The same applies also for the orientation of the parts of the nucleic acid molecule to be manufactured which form part of the respective ligation products as third oligonucleotide moiety arranged between the first and the second oligonucleotide moiety. It will be appreciated that the terms first, second and third moiety refer to units or moieties of the respective nucleic acid or oligonucleotide, whereby such moieties are created by dissecting the nucleic acid or oligonucleotide ligation product, respectively. The nomenclature 'first, second and third oligonucleotide moiety' is herein also used in the context of a intact oligonucleotide ligation product, where the nucleic acid or oligonucleotide ligation product is not dissected in the real world, but rather as the result of a mental process. In this case, the various moieties thus are not necessarily chemical moieties actually used in the design of the nucleic acid and oligonucleotide ligation products, respectively, but are intellectual units used to describe and illustrate what happens to individual parts or moieties of the nucleic acid and oligonucleotide, respectively.

The ASIT procedure provides another improved variant of the semi-inverted transposition procedure insofar as the cut second transposition product is only transiently created because restriction and ligation occur simultaneously. This is basically achieved by providing a second and third ligation product which each have, in contrast to the SIT procedure, not been subject to a digestion using both type IIS restriction enzymes the recognition sites of which are provided in the second and third ligation product, but using only that type IIS restriction enzyme cutting off from said ligation products only the corresponding first oligonucleotide moiety and third oligonucleotide moiety in both cases. If a surface such as a solid phase is present which allows specific binding of the modification contained in the second and third ligation product, the second oligonucleotide moiety of the second ligation product and of the third ligation product will be immobilised to such surface, whereas the remaining part of the molecule, i.e. the cut second ligation product and the cut third ligation product will be kept in solution. This solution is subsequently transferred to a reaction, preferably to a different reaction vessel as will be acknowledged by the one skilled in the art, where the first ligation product is present which is preferably immobilised to a surface.

In parallel, the supernatant which has been generated by this procedure and contains the cut third ligation product is transferred to a reaction where the cut fourth ligation product is present.

After combining the cut second ligation product and the cut first ligation product, actually two reactions are performed in the same reaction vessel, namely the ligation reaction and a cleavage reaction using the third type IIS restriction enzyme. Typically, these two reactions occur in parallel. Realising the respective reaction conditions such as ionic strength and the like, is known to the one skilled in the art as well as on how to use the respective enzymatic activities. Most preferably, the reaction is carried out in parallel with both enzymatic activities being active more or less at the same time, preferably at the same time.

The same sequence of steps and reactions is carried out with the cut third and cut fourth ligation product, whereby the two enzymatic reactions, namely ligation and cleavage, are carried out in the same reaction, using the fifth type IIS restriction enzyme for cleavage.

As a result of the desired ligation process, the recognition site for the third and fifth type of IIS restriction enzyme is no longer present in the correct ligation product, which is therefore no longer a substrate for the restriction enzyme. Consequently the overall reaction equilibrium favours the generation of the desired ligation product over the competing religation reaction.

In a fifth aspect the present invention is related to a method for the ligation of a first oligonucleotide and a second oligonucleotide. In this method, basically, a capping oligonucleotide is ligated to known by-products of a ligation reaction which may interfere with the hybridisation and ligation of a first and a second oligonucleotide which are contained in a ligation reaction and the ligation of which is desired and intended.

It will be understood by those skilled in the art that in a ligation reaction, preferably in a ligation reaction as described in connection with any of the Sloning processes, more particularly those embodiments of the respective transposition procedures described herein, it may occur that a ligation reaction comprises not only those compounds which are to be ligated. Such compounds have, in a preferred embodiment, an at least partially double-stranded structure and a single-stranded overhang, whereby such overhangs are essentially complementary to each other. A false, i.e. undesired ligation can, for example, occur if a further oligonucleotide, which is neither to be ligated to the first oligonucleotide nor to the second oligonucleotide of the ligation reaction, is contained in the ligation reaction, provided that said further oligonucleotides contains a single strand overhang with at least partial complementarity to one of the ends to be ligated.

It is also to be understood that in an embodiment the first and second oligonucleotide which are to be ligated, are either perfectly matching or are at least partially matching with regard to their single-stranded overhangs. At least, the match between the first oligonucleotide and the second oligonucleotide via their single-stranded moieties is such that it is preferred to the hybridisation of any other components to said first oligonucleotide and second oligonucleotide, respectively, contained in said ligation reaction, such as the further oligonucleotide. Nevertheless, possible false ligation reactions are not only driven by perfect complementarity but also by the relative concentration of available ligation partners. Thus, an unreacted intermediate from a preceding reaction can under certain circumstances be present in a large excess over the correct ligation partner, especially when this ligation partner is generated by a transposition cycle. The maximal possible yield of any transposition ligation is limited by the ligation partner that is present at the lower concentration. If, as may be the case sometimes, the conditions are such that the yield of one reaction partner is very low, then all subsequent reactions comprising this molecule are necessarily also generated in low yield even if all other reaction partners are provided in good yield. The problem may be aggravated by the fact that in the transposition phase of most Sloning processes one of the reaction partners is bound to a surface thereby significantly reducing the effectively available reaction volume. The kinetics of such solid phase ligation reactions are diffusion limited and compare very unfavourably with the reaction kinetics in solution. Therefore, the competition for binding the correct ligation partner is high because chances are that the ligation partner in the solution phase will have only rare encounters with the immobilised correct ligation product. Furthermore, a consequence of the combinatorial assembly of the ligation products in the transposition phase is that there is one reaction vessel in which all consecutive ligations occur so that all reaction intermediates will be finally united in one reaction vessel. As practically none of the preceding transposition reactions will go to completion in any given cycle, the excess of unreacted molecules accumulated at the solid phase increases exponentially. If now any of these unreacted precursor molecules happens to display a single-stranded overhang with significant complementarity to the single-stranded overhang of the ligation partner in solution, false ligation events may out compete the desired ligations after a number of cycles. There is a need in the art therefore to prevent such false ligations to improve the yield of the correct ligations.

This need is met by introducing another species of oligonucleotides, which are specifically designed to cap the ends of unreacted side products so as to prevent their further ligation to a correctly formed intermediate in any of the subsequent steps. Such capping oligonucleotides are suitable to remove any of the above described undesired ligation reaction partners.

In a preferred embodiment, the ligation between the further oligonucleotide and the capping oligonucleotide is preferred to the ligation of the capping oligonucleotide to the first oligonucleotide or the second oligonucleotide. This preference can be created in various embodiments of the present invention by designing the sequence of the capping oligonucleotide, particularly the single-stranded overhang thereof, such as to provide for a higher binding energy and thus a more effective hybridisation of the capping oligonucleotide to the further oligonucleotide compared to the hybridisation to the first and second oligonucleotide, respectively. Both perfect matches and single mismatches between the overhangs of the capping oligonucleotides and the intermediated to be capped are within the scope of the present invention.

It is also within the present invention that such preference may be generated by kinetics rather than by binding energies arising from hybridisation. A kinetic control can be achieved, e.g., by increasing the amount of capping oligonucleotide such as to increase the likelihood of a hybridisation and subsequent ligation of the capping oligonucleotide with the further oligonucleotide and thus effectively removing the further oligonucleotide from the ligation reaction of the first oligonucleotide and the second oligonucleotide. Preferably, this kinetic controlled reaction is generated by providing the capping oligonucleotide in excess. More particularly, the excess ranges from two to fiftyfold, from five to twentyfold or from seven to tenfold. It should be noted that the relative excess of any capping oligonucleotide can only be estimated since the total concentration of the reaction intermediates in the transposition cycles can become very low.

In a preferred embodiment, the capping oligonucleotide does not comprise a recognition site for a type IIS restriction enzyme or a part thereof. However, in alternative embodiments, also the capping oligonucleotide may comprise a recognition site for a type IIS restriction enzyme or a part thereof. Especially preferred are rare cutting outside cutting restriction endonucleases or restriction enzymes that create blunt ends as they allow to physically destroy the capped ligation products.

Finally, capping oligonucleotides may also be directed against the ends of that ligation partner, which is present in excess relative to its intended partner. In this case, the capping is controlled by the order of addition of the molecules, i.e. the capping oligonucleotides are added after the actual ligation has taken place.

In a sixth and/or seventh aspect the present invention is related to another method for the manufacture of a nucleic acid molecule. It will be acknowledged that this method is a variant of the RSPS method such as described in international patent application PCT/EP 03/11551 and the RLPS method which is also described in said international patent application. By combining both methods the method according to the sixth aspect of the present invention, the overall efficacy of the method is considerably increased. This method is also referred to herein as S4LS method. In short, S4LS comprises one solid phase reaction cycle, followed by four liquid phase reaction cycles, which are again followed by a final solid phase reaction cycle. The term "solid phase reaction cycle" implies that a ligation product in an elongation step is first bound to a surface where after the elongated first oligonucleotide is cleaved off this surface, yielding a practically pure product. The term "liquid phase reaction cycle" means that in an elongation step the ligation product is first cleaved by the second type IIS restriction enzyme in the liquid phase where after the reaction products containing a modification are bound to a suitable surface and thereby removed before entering a new cycle.

Without wishing to be bound by any theory, the increased yield observed in connection with the S4LS method, mainly arises from the fact that the kinetics of enzymatic reactions, particularly the cleavage reactions are much faster in solution than on a solid phase where diffusion pathways are much longer. The incubation times can therefore be shortened, thus increasing the throughput of the Sloning process. In contrast to the solid phase reaction cycle, however, there is no selection possible that excludes non-ligated first oligonucleotides from being transferred into a new reaction cycle.

The present invention is now further illustrated by the following figures and example which are given for purpose of example but not for purpose of limitation. From said figures and examples further features, embodiments and advantages of the various aspects of the present invention may be taken either alone or in any combination irrespective of whether such single feature or combination of feature is literally disclosed.

FIG. 1 shows an illustration of the method for the manufacture of a nucleic acid according to the first aspect of the present invention;

FIG. 2 shows the design of a first elongated first at least partially double-stranded oligonucleotide and of a second or further elongated first at least partially double-stranded oligonucleotide;

FIGS. 3 to 5 show an illustrative overview of the transposition reaction of the method according to the second aspect of the present invention;

FIG. 6 shows the structure of a ligation product

FIGS. 7 to 9 show a schematic illustration of the method for the manufacture of a nucleic acid according to the third aspect of the present invention using ligation products having a structure as described in FIG. 6

FIG. 10 shows further possible structures of a ligation product

FIGS. 11 to 13 show a schematic illustration of the method for the manufacture of a nucleic acid according to the third aspect of the present invention using ligation products having a the structure as described in FIG. 10;

FIG. 14 shows a schematic illustration of the method for the manufacture of a nucleic acid according to the fourth aspect of the present invention;

FIG. 15 shows a schematic illustration of the SIT procedure;

FIG. 16 shows a schematic illustration of a capping oligonucleotide which can be used in the ligation method according to the fifth aspect of the present invention;

FIGS. 17 and 18 show a schematic illustration of the S4LS procedure;

FIG. 19 shows a gel depicting the generation of three different elongation blocks using either the S4LS procedure or the reverse solid phase synthesis procedure; and FIG. 20 shows a diagram indicating the relative yield of the different elongation blocks using either the S4LS procedure of the reverse solid phase synthesis procedure (FIG. 20 A), and the yield of various elongation blocks in the S4LS procedure (FIG. 20 B), both based on a densitometric analysis of the gel depicted in FIG. 19.

FIG. 1 shows an illustration of the method for the manufacture of a nucleic acid according to the first aspect of the present invention. First, a first oligonucleotide which is referred to as E1, is provided which comprises a first and a second single-stranded overhang, whereby the second single-stranded overhang is longer than the first single-stranded overhang. This first oligonucleotide is also referred to as left starter molecule. Subsequently, a second oligonucleotide is provided which comprises a recognition site for a first type IIS restriction enzyme and a modification. This second oligonucleotide is also referred to as anchor. The anchor is provided in excess so as to allow for an efficient ligation which occurs via the short single-stranded overhang of the left starter molecule and the single-stranded overhang of the anchor. In this example, the overhang consists of three nucleotides which are perfectly base paring (FIG. 1.1).

The ligation product which is also referred to herein as the first ligation product is bound to a surface, preferably a solid surface, via the long second single-stranded overhang of the left starter molecule which is in this case the only single-stranded overhang available after successful ligation of the left starter molecule and the anchor molecule. The binding of the first ligation product is mediated through a single-stranded nucleic acid which is immobilised to the surface and allows for the binding of the first ligation product to said single-stranded nucleic acid via base pairing, preferably Watson-Crick base pairing. The thus immobilised first oligonucleotide is subsequently washed thus removing the other components of the ligation reaction such as ligase, and unligated anchor (FIG. 1.2).

After the washing the first ligation product is eluted from the surface, preferably by moderate heating in 1×TE and subsequently transferred into a new well. This new well is uncoated and allows the first ligation product to be kept in solution (FIG. 1.3)

To this reaction suitable buffer and the first outside cutting restriction enzyme is added so as to allow digestion of the first ligation product. Due to the cleaving activity of said outside cutting restriction enzyme the left starter molecule now comprises on both strands those nucleotides which have been cleaved off from the anchor, in the present case on the first strand the CTG and on the second strand TTG. Thus an elongated first at least partially double-stranded oligonucleotide and a truncated second at least partially double-stranded oligonucleotide have been created (FIG. 1.4).

This reaction mixture is subsequently transferred to another reaction vessel where a surface is provided which allows for the specific interaction of the modification of said second oligonucleotide. By this arrangement, any anchor, regardless whether it is a truncated anchor or a full-length anchor as well as any first ligation product which has not been cleaved by the first outside cutting restriction enzyme is immobilised. Accordingly, only the elongated first at least partially double-stranded oligonucleotide is kept in solution (FIG. 1.5).

From the respective reaction vessel this kind of elongated first at least partially double-stranded oligonucleotide may be transferred into another vessel which does not comprise a surface specifically interacting with the modification of a second at least partially double-stranded oligonucleotide, i.e. another anchor which provides another set or stretch of consecutive nucleotides to be transferred from said anchor to the elongated first at least partially double-stranded oligonucleotide and which correspond to a part of the nucleic acid to be synthesised (FIG. 1.6).

FIG. 2 shows the design of a first elongated first at least partially double-stranded oligonucleotide and of a second or further elongated first at least partially double-stranded oligonucleotide. Both the first elongated first at least partially double-stranded oligonucleotide and the second or further elongated first at least partially double-stranded oligonucleotide have a design similar to the one as described in FIG. 1.6. Both oligonucleotides comprise a sequence of nucleotides which forms part of the nucleic acid molecule to be synthesised. The individual nucleotides were transferred from the anchors used as depicted in FIG. 1.1. As can be taken from FIG. 2.1, these oligonucleotides were built up by transferring triplets of nucleotides from anchor molecules. Both oligonucleotides were synthesized individually, preferably in parallel reactions. The first or short overhang of both oligonucleotides allows for ligation, whereas the second or longer overhang provide for immobilization. The second single-stranded overhang is also referred to as left selector binding region in case of the first elongated first at least partially double-stranded oligonucleotide, and as right selector binding region in case of the second or other elongated first at least partially double-stranded oligonucleotide.

FIG. 2.2 shows the ligated product which is also referred to as the first extended ligation product or T 1.1, which can be split up, on paper, into a first oligonucleotide moiety comprising a recognition site 1 which is a recognition site for a type IIS restriction enzyme, depicted on the left side, a second oligonucleotide moeiety comprising a recognition site 2 which is a recognition site for a type IIS restriction enzyme, depicted on the right side, and a third oligonucleotide moiety which comprises a part of the nucleic acid to be manufactured. Line A3 indicates the ligation site, where lines A1 and lines A2 indicate the cleavage site of the first type IIS restriction enzyme the recognition site of which is contained in the first oligonucleotide moiety, and the cleavage site of the second type IIS restriction enzyme the recognition site of which is contained in the second oligonucleotide moiety, By ligating these two oligonucleotides, a bigger part of the nucleic acid molecule to be manufactured is prepared compared to those part of the nucleic acid molecule provided by the two elongated first at least partially double-stranded oligonucleotides used as starting materials.

FIGS. 3 to 5 show an overview of the transposition of the method according to the second aspect of the present invention. As depicted in FIG. 3.1.1 two oligonucleotides are provided which are in the present case elongated first at least partially double-stranded oligonucleotides as depicted on FIG. 2. The elongated first at least partially double-stranded oligonucleotide is referred to as E1, whereas the second, further or another elongated first at least partially double-stranded oligonucleotide is referred to as E2. The starting molecule for the synthesis of the latter oligonucleotide was a "right starter" which has a second overhang different from the left starter.

E1 comprises an at least partially double-stranded structure, whereby in the present case a total of five units each consisting of three nucleotides, have been transferred to the oligonucleotide which corresponds to the one described in step a) of the method according to the first aspect of the present invention. The short single-stranded overhang is a 5'-overhang. E1 comprises a second single-stranded overhang which is also referred to as the long single-stranded overhang. E2 has a basically similar structure, however, the second single stranded overhang is different from the one of E1 which allows for a specific immobilisation of each of the ends of both E1 and E2. The first single-stranded overhang of E2 is in the present case again a 5'-overhang, whereby this overhang is complementary to the first single-stranded overhang of E1. It is to be noted that taken both E1 and E2, the overhang is located at opposite ends which is a prerequisite for the ligation. Upon annealing and ligation a first extended ligation product or first level transposition product (T1.1) is formed (FIG. 3.1). T1.1 comprises in the present case a total of 10 nucleotide triplets which were added to E1 and E2 by combining the oligonucleotide according to step a) of the method according to the first aspect of the present invention with a second and each another oligonucleotide as of step b) of the method according to the first aspect of the present invention.

T 1.1 is annealed to a left selector oligonucleotide, whereby said left selector oligonucleotide is present either in immobilized form or in solution. In the latter case, the complete annealing product formed by T1.1 and the left selector oligonucleotide is then immobilised via the modification provided by the left selector oligonucleotide. Preferably, the selector is already immobilised and complementary to the second or longer single-stranded overhang of T 1.1.

Preferably, the reaction mixture is transferred into a reaction vessel where immobilisation of the T 1.1 occurs). Such immobilisation is a purification of the first extended ligation product T 1.1. In this immobilisation process, however, immobilisation occurs only via one of the two second single-stranded overhangs still existing in the transposition product, whereby one of the overhangs is contributed by the left starter and the other one by the right starter. By doing so, any other component of the reaction mixture which does not comprise a second single-stranded overhang which allows for specific immobilisation to the surface provided by said reaction vessel can be washed off. If, as indicated in FIG. 3.2 the immobilisation occurs through the second single-stranded overhang as provided by E1, any unligated E2 will not bind to the matrix and hence will be removed.

As depicted in FIG. 4 to further purify the first transposition product, it is subsequently released from the surface and transferred to another reaction vessel where a surface is provided which allows the binding of T1.1 to the surface which is mediated through the second single-stranded overhang provided by E2 (FIG. 4.3). Such elution of T 1-1 from the solid phase of FIG. 4.1 can be done by heating the reaction beyond the melting temperature of the hybrid formed between the left selector which is the nucleic acid which is base pairing with the second, longer single stranded overhang of E1. In a subsequent washing step, any unreacted E1 still present in the reaction mixture, is maintained in the supernatant and can thus be washed away.

Once T1.1 is released form the solid phase interacting with the left selector binding region, it is subjected to a reaction with the right selector oligonucleotide, i.e. the oligonucleotide interacting with the right selector binding region as, e.g. depicted in FIG. 2.2. Upon binding to a solid phase, any remaining unreacted ligation partner i.e. E1, is removed. Such reaction partner is typically comprising the left selector binding region only (FIG. 4.3). Again, the immobilized T 1.1 is eluted such as by increasing the temperature above the melting temperature of the hybrid formed from the right selector and the right selector binding region (FIG. 5.1).

In a subsequent reaction, the thus purified T 1.1 is cleaved by the second type IIS restriction enzyme forming the cut first extended ligation product Cut T 1.1 (FIG. 5.2). In order to remove the remainder of E2 which was cut off T 1.1 this remainder is annealed with the right selector oligonucleotide either in an immobilized form or in solution, and bound to a solid phase. The cut T 1.1 remains in the supernatant and is subsequently transferred into a new vessel for further processing.

The same sequence of reactions is carried out with E3 and E4 being other elongated first at least partially double-stranded oligonucleotides Again, E3 and E4 provide a sequence of nucleotides which form part of the nucleic acid to be synthesised. By ligating E3 and E4 another part of the nucleic acid to be synthesised is thus created, whereby the part of E3 and E4 as represented by the third oligonucleotide moiety are consecutive parts of the nucleic acid molecule to be manufactured as are the parts of E1 and E2. The ligation product of E3 and E4 is also referred to herein as a second extended ligation product or second first level transposition product (T1.2). The consecutive nucleotides contained in both T1.1 and T1.2 are adjacent or consecutive stretches of the nucleic acid to be synthesised and have the same orientation. In other words, combining the respective stretches of the first and the second first level transposition products generates a bigger part of the nucleic acid molecule to be synthesised.

Both the first (T 1.1) and second transposition products (T 1.2) are treated separately. In the present example, the type IIS restriction enzyme used for T 1.1 is Eco31I, and the one used for T 1.2 is Esp 3I. Depending on the particular restriction enzyme used it may be that the first single-stranded overhang generated by the use of the restriction enzyme generates an overhang which is different from the one used when generating the elongation blocks such as E1 and E2. This results from the particular mode of action of the restriction enzyme. In the present case, for example, four nucleotide long single-stranded overhangs are generated in the transposition phase.

As mentioned above, what has been described in connection with the first transposition product is repeated with E3 and E4 forming the second extended ligation product which is also referred to herein as the second first level transposition product (T1.2). Said second transposition product is cleaved by a outside cutting restriction enzyme providing the same kind of single-stranded overhang as the one used in connection with the first transposition product. In the present case, the outside cutting restriction enzyme used is Esp3I. Again, an elongated at least partially double-stranded oligonucleotide is thus provided. By annealing the four nucleotide overhangs generated with Eco31I on T1.1 and Esp3I on T1.2, respectively the two transposition products may be ligated under the provision that the overhangs are base pairing, whereby again such ligation occurs in solution increasing the yield significantly. It is to be acknowledged that in connection with the cutting of the second transposition product the type II restriction enzyme the recognition site of which is contained in E3 is used which is thus actually the third type IIS restriction enzyme using the terminology used herein.

The thus created ligation product may serve as a further transposition product and the steps described above can be repeated with this and another further transposition product which comprises the stretch of consecutive nucleotides of the nucleic acid to be manufactured either preceding or following the respective sequence of consecutive nucleotides now contained in the further transposition product.

The type of restriction enzyme used is alternating for each intermediate fragment in each transposition step, i.e. the two transposition intermediates that are to be ligated are cut with different outside cutting restriction enzymes.

FIG. 6 shows the design of a ligation product, whereby the ligation product can be any of ligation products described herein, particularly in connection with the third aspect of the present invention and even more particularly in connection with FIGS. 7 to 13. Basically, such design consists of a first oligonucleotide moiety comprising a recognition site 1 or recognition site for a first type IIS restriction enzyme, a second oligonucleotide moiety comprising a recognition site 2 or a recognition site for a second type II restriction enzyme and a third oligonucleotide moiety. The third oligonucleotide moiety comprises a part of the nucleic acid molecule to be manufactured. In the present case the third oligonucleotide moiety consists of five nucleotide triplets. Each triplet has been transferred in an individual elongation step as provided, e.g. by the Sloning processes as described herein, either directly or by reference. The second moiety provides for a modification which allows for the specific immobilization of the ligation product.

The first type IIS restriction enzyme the recognition site of which is contained in the ligation product depicted in FIG. 6 is Esp3I, whereas the second type IIS restriction enzyme the recognition site of which is contained in the ligation product depicted in FIG. 6 is Eco 31I. Due to these restriction enzymes, upon cleavage of the ligation product with both of said restriction enzymes, the lower strand is lacking the 3' most nucleotide and gains a nucleotide from the lower strand of the second oligonucleotide moiety. As a result, there is no need to duplicate a nucleotide at the transition point from one elongation block to the other as would be the case when the restriction enzyme specific for the second oligonucleotide moiety would cleave one nucleotide off the third oligonucleotide moiety representing part of the nucleic acid to be manufactured.

FIGS. 7 to 9 show a schematic illustration of the method for the manufacture of a nucleic acid according to the third aspect of the present invention.

As may be taken from FIG. 7, a first, second, third and fourth ligation product as used in this method and referred to in FIG. 7 as E1, E2, E3 and E4, are provided in accordance with known processes, namely by generating an elongation product to which another member of the library as described in international patent applications PCT/DE00/01863, PCT/EP02/13154 or PCT/EP03/11551 is ligated. The basic structure of any of E1, E2, E3, and E4 corresponds to the one as depicted in FIG. 6 and described above. This basic step may have been repeated several times so as to create the third oligonucleotide moiety corresponding to a part of the nucleic acid molecule to be manufactured. The arrangement of the coding and non-coding strand as depicted in this figure is in accordance with the above provided description (FIG. 7.1)

It is to be noted that any of the ligation products comprises a modification which allows the selective adsorption of the ligation product to a surface, preferably to a solid phase. In the particular case represented in this figure, the modifications are provided by two different kinds of oligonucleotides which are both contained in the standardised oligonucleotide library. One kind provides another set of nucleotides to be transferred to the elongation block, whereas the other kind is used to add a different recognition site for an outside cutting restriction endonuclease to the elongation block. The first kind of library oligonucleotide is also called anchor oligonucleotide or anchor, the second kind of library oligonucleotide is also called transition anchor oligonucleotide or transition anchor. As explained previously, these oligonucleotides are also commonly referred to herein as second oligonucleotide moieties when they are part of a ligation product or elongation block.

In a next step as depicted in FIG. 7.2, each of the ligation products is cut by a type IIS restriction enzyme generating a single-stranded overhang. The term "modified rxn products" refers to the reaction products of this cleavage reaction, which bear the modification, i.e. both cut ligation product encompassing the anchor part and uncleaved ligation product. In case of ligation product E1 as depicted in FIG. 7.2 the respective restriction enzyme is Esp3I which is thus the first type IIS restriction enzyme As a result of this digestion the first oligonucleotide moiety is cleaved off producing a molecule having the basic structure of all anchor oligonucleotides of said library plus the individual sequence block formed by the nucleotides having been transferred in previous elongation steps from other anchor oligonucleotides of said library. The resulting nucleic acid molecule is preferably formed by the third and second oligonucleotide moiety, which corresponds to the last anchor oligonucleotide transferred. Due to the arrangement of the cleavage site, the bigger part of the first ligation product comprising the third oligonucleotide moiety and the second oligonucleotide moiety is preferably immobilised to a surface via the modification provided by the second oligonucleotide moiety. This molecule is also referred to as first cut ligation product.

Ligation product E2 is digested using the restriction enzyme the recognition site of which is provided by the second oligonucleotide moiety of the second ligation product which is thus the fourth restriction enzyme. In this particular case said fourth restriction enzyme is Eco31I. Upon cleavage, a longer part of the second ligation molecule is released which is the second cut ligation product. The remainder of the second ligation product, i.e. the second oligonucleotide moiety of the second ligation product remains attached to a surface via its modification. This reaction occurs typically in a separate reaction or reaction well and the supernatant containing the second cut ligation product is transferred to the first reaction, preferably reaction vessel, where the first cut ligation product is immobilised. Upon hybridisation of the first cut ligation product and the second cut ligation product via their matching single strand overhangs, they are ligated generating a first transposition product which is referred to in FIG. 2 as T1.1. T1.1 comprises both the part of the nucleic acid molecule to be manufactured provided by E1 and the one provided by E2, which are in the same orientation so that they need not be flipped in this step (FIG. 7.3).

The first transposition product is subsequently cleaved by the third type IIS restriction enzyme which in the present case is Esp3I (FIG. 7.5). It is obvious that in any of the reactions, where compounds are immobilised such as the first transposition product, the surface carrying the immobilised molecule (s) may be washed and thus any impurities such as any starting material of the respective reaction may be removed so as to purify the desired respective reaction product. This includes also the cut first transposition product resulting from the cleavage of the first transposition product by the third type IIS restriction enzyme.

In parallel, the same reactions as described above for the first and the second ligation products are performed on ligation products E3 and E4 with Eco3I being the sixth type IIS restriction enzyme generating a third cut ligation product and Esp3I being the seventh restriction enzyme generating a fourth cut ligation product. In this arrangement, the fourth cut ligation product E4 is immobilised to a surface and the third cut ligation product E3 is transferred to the reaction or reaction well where the fourth cut ligation product is contained, more preferably immobilised, so as to form the second transposition product T1.2 which is subsequently cleaved by Esp3I, i.e. the fifth type IIS restriction enzyme. Again, after each and any step a washing step may be included so as to remove any starting material or non-immobilised reaction products which increases the purity of the respective immobilised compounds used in subsequent reactions.

In addition to cleaving the second transposition product by the fifth restriction enzyme, it is additionally cleaved by the eighth type IIS restriction enzyme (FIG. 7.5). Preferably, between said two cleavage steps using the fifth and eighth type IIS restriction enzyme a washing step is introduced so as to remove the cleaved-off part of the E3 ligation product. After completion of the cleavage of the second transposition product by using both the fifth and the eighth type IIS restriction enzyme is devoid of any protecting loops but long enough to be stable under the reaction conditions used because they are formed by two consecutive parts of the nucleic acid to be manufactured. This product, which is also referred to as T1.2 in, among others, FIG. 7.3, is transferred to the reaction well where the cut first transposition product is immobilised, whereby both transposition products are ligated generating the second order transposition product T2.1 (see FIG. 9). T 2.1 comprises a total of four consecutive parts of the nucleic acid to be manufactured in the correct orientation.

The same process is carried out for ligation products E5, E6, E7, and E8 as depicted in FIGS. 8.1 to 8.5. The respective type IIS restriction enzymes used can immediately be taken from the respective figures. As a result a third and fourth transposition product T 1.3 and T 1.4 are generated which are ligated as depicted in FIG. 9. creating the second order transposition product T 2.2. Second order transposition product T 2.2 is then digested with Eco31I which is the sixteenth type IIS restriction enzyme releasing a stretch of consecutive parts 5, 6, 7, and 9 of the nucleic acid to be manufactured. T 2.2 is then ligated to immobilized T 2.1, whereby the ligation occurs in reverse orientation similar to the ligations depicted on FIG. 7.5 and 8.5. As a result a third order transposition product T3 is obtained containing a total of 8 consecutive parts of the nucleic acid to be manufactured.

FIG. 10 shows two further possible structures of a ligation product. Both ligation products depicted in FIGS. 10.1 and 10.2 comprise a first oligonucleotide moiety comprising a recognition site for a first type IIS restriction enzyme, a second oligonucleotide moiety comprising a recognition site for a second type IIS restriction enzyme and a third oligonucleotide moiety which is a part of the nucleic acid molecule to be manufactured. In contrast to the ligation product design as depicted in FIG. 6, the ligation product as depicted in FIG. 10.2 comprises a recognition site for a type IIS restriction enzyme which is different from both the first and second restriction enzyme recognition site contained in the ligation product as depicted in FIG. 10.1 as well as different from the first type IIS restriction enzyme recognition site as present in the ligation product as depicted in FIG. 10.2. In accordance therewith, this restriction enzyme is referred to in the embodiment of the method according to the third aspect of the present invention as third type IIS restriction enzyme. The third type IIS restriction enzyme can be Eam1104I, whereas the first type IIS restriction enzyme is Esp3I, and the second type IIS restriction enzyme is Eco31I.

FIGS. 11 to 13 show a schematic illustration of the method for the manufacture of a nucleic acid according to the third aspect of the present invention using ligation products having a the structure as described in FIG. 10. More particularly, ligation products E1 and E4 are of the ligation product type as depicted in FIG. 10.2, whereas ligation products E2 and E3 are of the ligation product type as depicted in FIG. 10.1. The steps to be performed are basically the same as described in FIGS. 7 to 9. However, in the step depicted as FIG. 11.4 T 1.2 is cleaved using the third type IIS restriction enzyme which is, in the present case, Eam1104I. Also, in step 12.5 where T 1.3 is cut, the third type IIS restriction enzyme, which is Eam1104I in the present case, is used. Finally, the third type IIS restriction enzyme is used in the step depicted in FIG. 13.2, where T 2.2 is cleaved using this kind of restriction enzyme. The advantage of this particular design is that after the second transposition cycle only 3 nucleotide overhangs are ligated, which per definition cannot be self-complementary.

FIG. 14 shows a schematic illustration of the method for the manufacture of a nucleic acid according to the fourth aspect of the present invention.

Similar to the situation depicted in FIGS. 7 to 13 for the method for the manufacture of a nucleic acid according to the third aspect, again, the first, second, third and fourth ligation product as used in this method and referred to in FIG. 14 as E1, E2, E3 and E4, are provided in accordance with known processes, namely by generating an elongation product to which another member of the library as described in international patent applications PCT/DE00/01863, PCT/EP02/13154 or PCT/EP03/11551 is ligated. This basic step may have been repeated several times so as to create the third oligonucleotide moiety corresponding to a part of the nucleic acid molecule to be manufactured.

The design of the ligation products corresponds to the one FIG. 6. Again, the arrangement of the upper and lower strand as depicted in this figure is in accordance with the above provided description. It is to be noted that any of the ligation products comprises a modification which allows the selective adsorption of the ligation product to a surface, preferably to a solid phase. In the particular case represented in this figure, the modification is provided by a member of the library providing another set of nucleotides to be transferred to the building block, i.e. by the second oligonucleotide moiety. It is to be understood that the arrangement and orientation of the various parts of the nucleic acid to be manufactured being contained in the ligation products as third oligonucleotide moiety, is in principle the same as described for the SIT procedure herein.

The first and fourth ligation product are cleaved by Esp3I which is the second and fourth type IIS restriction enzyme in the present case. Such digestion can either be carried out with the respective ligation product being immobilised to a surface or, more preferably, with the ligation product in solution followed by binding the reaction products to a suitable surface. In the latter case, one can take advantage of the higher efficiency of solution phase digestions and remove the unwanted first oligonucleotide moiety in a subsequent binding and washing step. Either way, the thus cleaved off parts of the first and fourth ligation product corresponding to the first oligonucleotide moiety of the first ligation product and of the fourth ligation product, respectively, are washed away as well as any other starting material or products generated by said digestion process. At the end of such cleavage and washing, the cut first and cut fourth ligation product are purified and typically present as different reactions, more preferably in different reaction wells (FIGS. 14.1 to 14.3).

In parallel or subsequent to the steps described before, the second ligation product is cleaved using Eco31I as the fourth type IIS restriction enzyme, whereby the second ligation product is preferably immobilised to a surface. If the uncleaved second ligation product has first been immobilised to a surface, this cleavage will release a cut second ligation product, which will be present in solution. The cut second ligation product comprises the first oligonucleotide moiety and the third oligonucleotide moiety of the second ligation product. The same reaction is, in principle, carried out with the third ligation product, whereby in this case Eco31I is used as the sixth type IIS restriction enzyme the recognition site of which is provided by the second oligonucleotide moiety of the third ligation product. Again, the cut third ligation product is set free and available in solution (FIGS. 14.1 to 14.3)

The cut second ligation product is transferred to the reaction where the cut first oligonucleotide is present. This reaction comprising both the cut first and the cut second ligation product is then subject to a treatment using both a ligase and Esp3I as the third type IIS restriction enzyme the recognition site of which is provided by the first oligonucleotide moiety of the cut second ligation product. It will be appreciated that both the ligation reaction as well as the cleavage reaction by the restriction enzyme are performed more or less in parallel thus generating a cut first transposition product T1.1. In the process of this cutting and ligating, the orientation of the part of the nucleic acid to be manufactured as provided by E2 is reversed for ligation purposes (FIG. 14.4).

Again, the same sequence of steps and reactions is carried out on the cut third and the cut fourth ligation product. The cut third ligation product present in the supernatant is transferred to the reaction, preferably the reaction vessel, where the cut fourth ligation product is present and both a ligation reaction and a cleavage reaction using Esp3I as the fifth type IIS restriction enzyme which generates, taken together, a cut second transposition product, referred to as T1.2. In the process of this cutting and ligating, the orientation of the part of the nucleic acid to be manufactured as provided by E3 is reversed for ligation purposes (FIG. 14.4). This cut second product is subsequently cleaved using Eco31I as the eighth type IIS restriction enzyme thus creating the cut second transposition product. This cut second transposition product is then transferred to the reaction where the first cut transposition product T1.1 is present, which is preferably immobilised through the modification provided by the second oligonucleotide moiety of the first ligation product. After ligation, a second order transposition is produced (T2.1), which may further be used as the first transposition product in subsequent transposition steps. The rationale behind this sequence of steps is to ensure that the double cut intermediates 2 and 3 shown in FIG. 14.4 are only transiently formed because their double-stranded part is shorter than in the S-HIT procedure and therefore prone to thermal denaturation, especially when the parts of the nucleic acid to be manufactured which they represent are AT-rich.

Just by way of example, FIG. 15 is provided showing the SIT procedure as described earlier, where, briefly, the same steps as described for the aSIT procedure with reference to FIG. 14 is shown. However both the ligation reaction and the cleavage reaction performed on E2 and E3 are not carried out at the same time and also the sequence of restriction enzyme cleavage is reversed for both E2 and E3.

FIG. 16 shows a generic design of a so-called capping oligonucleotide

FIGS. 17 and 18 outline the elongation cycles of the S4LS procedure, in which the first reaction cycle is carried out as a solid phase cycle, i.e. the ligation product of the first and the second oligonucleotide is first bound to the solid phase as in step d) and then digested with the type IIS restriction enzyme the recognition site of which is contained in the second oligonucleotide as in step e), thereby releasing an elongated first oligonucleotide. In the subsequent steps f) to i) the elongation cycles are repeated but the order of the binding and cleavage step is reversed. Such a procedure takes advantage of the higher cleavage efficiency of restriction enzymes in solution at the expense of accumulating non-reacted first oligonucleotide or elongated first oligonucleotides. However, since in the final repetition, in steps k) and l) the order of the binding and cleavage step is again reversed, a purified elongation product is obtained because any of the unreacted first or elongated first oligonucleotides will not bind to the solid phase since these molecules lack the modification contributed by the second or further oligonucleotide.

FIGS. 19 and 20 show a comparison between three different elongation blocks generated with the S4LS method as described herein and the same elongation blocks generated with the RSPS (reverse solid phase synthesis) method. The major difference between the two methods is the reversion of the order of the binding and cleavage steps as described above. As theoretically predicted, the overall yield is significantly increased at the expense of the accumulation of side products. In the fifth step, however, the last ligation product is bound to the solid phase before restriction takes place resulting in both cases in a pure elongation product. The bands of the stained gels in FIG. 19 were quantitated using a densitometric screen and their relative intensities depicted in FIG. 20

EXAMPLE 1

Semi Half Inverted Transposition with Eco31I and Esp3I

Elongation blocks (E1-E4) were generated using standard methods, i.e. ligating the respective components such as anchors and splinkers, in 150 µl at 25° C. for 15 minutes (1× buffer Y$^+$, 10 mM DTT, 0.5 mM ATP), cleaving the ligation products with the respective outside cutting endo-nucleases in the same buffer supplemented with 100 µg/ml BSA for 60 to 90 minutes at 37° C. and using 15-100 U enzyme, and binding to suitable surfaces in the same buffer for 20 minutes at 25° C. Elongation blocks E1 and E4 were cut with Esp3I (by adding 1 µl equalling 100 U). All blocks were then bound to the appropriate plates. After binding blocks E2 and E3 were cut with Eco 31I (150 µl containing 1 µl 100 U/ml Eco31I, 15 µl buffer Y⁺ and 134 µL H₂O). The supernatants from blocks E2 and E3 were pipetted into the wells containing blocks E1 and B4, respectively, and 1 µl T4 DNA ligase (30 U/µl) 15 µl 5 mM ATP, 15 µl 10 mM DTT was added. The ligation was allowed to proceed for 1 hour at 25° C. This gives the T1 products T1.1 and T1.2.

Then the ligated blocks T1.1 and T1.2 were cut with Esp3I (in 150 µl reaction volume containing 1 µl 100 U/µl Esp3I, 15 µl buffer Y⁺, 15 µl 100 mM DTT and 129 µl H₂O). After washing block T1.2, it was additionally cut with Eco31I (150 µl containing 1 µl 100 U/µl Eco31I, 15 µl buffer Y⁺ and 134 µl H₂O). The supernatant from block T1.2 was pipetted into the well containing block T1.1, and 1 µl T4 DNA ligase (30 U/µl) 15 µl 15 mM ATP, 15 µl 100 mM DTT was added. The ligation was allowed to proceed for 1 hour at 25° C. to produce the T2 product; T2.1. Correspondingly, another second order transposition product is generated by the same course of reactions for a fifth to eighth elongation block. This molecule is referred to as T7.2 and is cleaved with Eco31I. The cut T2.2 is released from the solid phase and transferred to the T2.1 reaction, preferably the reaction vessel which the T2.1 intermediate is contained in. Upon ligation, a third order transposition product is formed, which is called T3.1.

EXAMPLE 2

Alternative Semi Inverted Transposition with Eco31I and Esp3I

Using the Sloning procedure as described in patent application PCT/EP 03/11551, transposition anchors and splinkers were first assembled in several ligation/restriction/binding cycles (ligation: 150 µl at 25° C. for 15 to 30 minutes (1× buffer Y⁺, 10 mM DTT, 0.5 mM ATP), restriction in the same buffer supplemented with 100 µg/ml BSA with 15 to 100 units Eam1104I for 60 to 90 minutes at 37° C., binding in the same buffer for 15 minutes at 25° C.) to yield the elongation blocks (E1-4). Elongation blocks 1 and 4 were cut with Esp3I in 1×Y⁺ (by adding 200 U enzyme). All blocks were then bound to the appropriate plates. After binding, blocks E2 and E3 were cut with Eco31I (in 150 µl reaction volume containing 1 µl 100 U/µl Eco 31I, 15 µl 10× buffer Y⁺ and 134 µl H₂O). The supernatants from blocks E2 and E3 were pipetted into the wells containing blocks E1 and E4, respectively, and 1 µl T4 DNA ligase (30 U/µl) 15 µl 5 mM ATP, 15 µl 10 mM DTT and 2 µl Esp3I was added. The ligation and the Esp3I digestion were allowed to proceed simultaneously for 1 hour at 37° C. This is to ensure that the short double-stranded pieces (15 nucleotides on each strand, but only 11 base pairs overlapping) are not denatured by an inactivation step of 10 min at 65° C. The rest of the procedure is as that for the semi inverted transposition.

Literature Citations

The following references are those to which it is referred to in the present application. The references are given here in order to avoid any unnecessary repetition throughout the application text and shall be deemed completely recited each and any time referred to herein. Also the disclosure of said references shall be incorporated herein by reference.

Sekiya T, Brown E L, Belagaje R, Fritz H J, Gait M T, Lees R G, Ryan M J, Khorana H G, Norris K E. (1979)
Total synthesis of a tyrosine suppressor tRNA gene. XV. Synthesis of the promoter region. J Biol Chem. 254(13): 5781-6.
Sekiya T, Takeya T, Brown E L, Belagaje R, Contreras R, Fritz H J, Gait M J, Lees R G, Ryan M T, Khorana H G, Norris K E. (1979)
Total synthesis of a tyrosine suppressor transfer RNA gene. XVI. Enzymatic joinings to form the total 207-base pair-long DNA.
J Biol Chem. 254(13):5787-801.
Stabinsky, Yitzhak (1987)
Manufacture and expression of structural genes
U.S. Pat. No. 4,652,639
Jayaraman, Krishna, Burdick, Brent A, Oakes, Fred T. (1992)
Method of making double-stranded DNA sequences
U.S. Pat. No. 5,132,215
Richards, John H, Iverson; Sheila A., Perez, Dianne M. (1992)
Cassette method of gene synthesis
U.S. Pat. No. 5,093,251
Hegemann P (2002)
Method for producing nucleic acid polymers
U.S. Pat. No. 6,472,184
Strizhov, Nicolai, Koncz, Csaba, Schell, Jeff (2000)
Gene synthesis method
U.S. Pat. No. 6,110,668
Hoare D G, Koshland D E, Jr. (1967)
A Method for the Quantitative Modification and Estimation of Carboxylic Acid Groups in Proteins
J. Biol. Chem. 242: 2447-2453.
Johnsson B, Lofas S, Lindquist G. (1991)
Immobilisation of proteins to a carboxymethyldextran-modified gold surface for biospecific interaction analysis in surface plasmon resonance sensors.
Anal Biochem. 198:268-77.
Bolli M, Micura R, Eschenmoser A. (1997)
Pyranosyl-RNA: chiroselective self-assembly of base sequences by ligative oligomerization of tetranucleotide-2',3'-cyclophosphates (with a commentary concerning the origin of biomolecular homochirality).
Chem Biol. (4):309-20.
Serke S, Pachmann K (1988)
An immunocytochemical method for the detection of fluorochrome-labelled DNA probes hybridized in situ with cellular RNA.
J Immunol Methods. 112(2):207-11.
Kessler C, Holtke H E, Seibl R, Burg J, Muhlegger K. (1990)
Non-radioactive labeling and detection of nucleic acids. I. A novel DNA labeling and detection system based on digoxigenin: anti-digoxigenin ELISA principle (digoxigenin system).
Biol Chem Hoppe Seyler. 371(10):917-27.
Wu D Y, Wallace R B. (1989)
Specificity of the nick-closing activity of bacteriophage T4 DNA ligase.
Gene. 76(2):245-54.

The features of the present invention disclosed in the specification, the claims and/or the drawings may both separately and in any combination thereof be material for realising the invention in various forms thereof.

The invention claimed is:

1. A method for the manufacture of a nucleic acid molecule comprising the following steps:
   (a) providing a first at least partially double-stranded oligonucleotide, whereby the oligonucleotide comprises a first single-stranded overhang, and a first modification allowing the oligonucleotide to be immobilised to a surface, wherein the first modification comprises a second single-stranded nucleotide overhang, wherein the first oligonucleotide is a first part of a nucleic acid to be manufactured,
   (b) providing a second at least partially double-stranded oligonucleotide, which comprises a recognition site for a first type IIS restriction enzyme which cuts outside its recognition site, a second modification allowing the oligonucleotide to be coupled to a surface and a single-stranded overhang, wherein the second oligonucleotide is a second part of a nucleic acid to be manufactured,
   (c) ligating the first oligonucleotide and the second oligonucleotide via the first single-stranded overhang of the first oligonucleotide and the single-stranded overhang of the second oligonucleotide, generating a first ligation product, whereby the first ligation product comprises the first modification allowing the first ligation product to be immobilised to a surface, wherein the first modification of the first ligation product is the second single-stranded nucleotide overhang of the first oligonucleotide,
   (d) cutting the first ligation product with the first type IIS restriction enzyme thus releasing
   an elongated first at least partially double-stranded oligonucleotide having a first and a second single-stranded overhang, whereby the first single-stranded overhang is generated through the cutting of the restriction enzyme and whereby the second single-stranded overhang is the second single-stranded nucleotide overhang of the first at least partially double-stranded oligonucleotide of step (a), and
   a truncated second at least partially double-stranded oligonucleotide;
   (e) immobilising the truncated second at least partially double stranded oligonucleotide of step d), the unreacted second at least partially double-stranded oligonucleotide and/or the uncut first ligation product via the second modification to a surface;
   (f) repeating steps (a) to (e) at least once, whereby the elongated first at least partially double-stranded oligonucleotide of step (d) serves as the first at least partially double-stranded oligonucleotide in step (a), and is further elongated.

2. The method of claim 1, comprising the following step ca) immobilising the first ligation product to a surface via the first modification comprising the single-stranded overhang.

3. The method of claim 2, wherein the surface comprises a nucleic acid having a single-stranded stretch which is at least partially complementary to the first modification of the first ligation product comprising the single-stranded overhang.

4. The method of claim 1, 2 or 3, comprising the following step cb) washing the immobilised first elongation product; and cc) releasing the immobilised first elongation product from the surface.

5. The method of claim 4, wherein the length of the first single-stranded overhang of the first at least partially complementary oligonucleotide has a length of 1, 2, 3, 4 or 5 nucleotides.

6. The method of claim 5, wherein the first modification comprising the second single-stranded overhang of the first oligonucleotide allows for a stable hybridisation to the single-stranded stretch of the nucleic acid comprised on the surface.

7. The method of claim 6, wherein the hybridisation is stable under the reaction conditions of step cb).

8. The method of claim 7, wherein the modification comprising the second single-stranded overhang of the first oligonucleotide has a length from about 5 to 20 nucleotides, from about 10 to 20 nucleotides, from about 15 to 18 nucleotides, from about 5 to 10 nucleotides and from about 6 to 8 nucleotides, depending on the nature of the nucleotides.

9. The method of claim 1, wherein the second modification of the second at least partially double-stranded oligonucleotide is a biotin modification.

10. The method of claim 9, wherein the immobilisation of step e) occurs via interaction of the biotin and the surface, whereby the surface preferably comprises a biotin interaction group.

11. The method of claim 10, wherein the biotin interaction group is selected from the group comprising avidin, streptavidin, extravidin, mutants of each thereof and synthetic biotin binding sites.

12. The method of claim 11, wherein a part of the nucleic acid to be manufactured is part of the elongated first at least partially double-stranded oligonucleotide.

13. The method of claim 12, wherein steps a) to e) are repeated at least once, whereby the nucleotides transferred from the second and any further at least partially double-stranded oligonucleotides provided in step b) to the first at least partially double-stranded oligonucleotides are the nucleic acid to be manufactured or a part thereof.

* * * * *

SEQUENCE LISTING

<160> NUMBER OF SEQ ID NOS: 28

<210> SEQ ID NO 1
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
    T
<220> FEATURE:
<221> NAME/KEY: misc_feature
<222> LOCATION: (8)..(8)
<223> OTHER INFORMATION: n stands for any of the nucleotides A, G, C or
    T
<220> FEATURE:
<221> NAME/KEY: misc_feature
<222> LOCATION: (9)..(9)
<223> OTHER INFORMATION: n stands for any of the nucleotides A, G, C or
    T
<220> FEATURE:
<221> NAME/KEY: misc_feature
<222> LOCATION: (10)..(10)
<223> OTHER INFORMATION: n stands for any of the nucleotides A, G, C or
    T
<220> FEATURE:
<221> NAME/KEY: misc_feature
<222> LOCATION: (11)..(11)
<223> OTHER INFORMATION: n stands for any of the nucleotides A, G, C or
    T

<400> SEQUENCE: 1
cgtctcnnnn n                                                              11

<210> SEQ ID NO 2
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
    T
<220> FEATURE:
<221> NAME/KEY: misc_feature
<222> LOCATION: (8)..(8)
<223> OTHER INFORMATION: n stands for any of the nucleotides A, G, C or
    T
<220> FEATURE:
<221> NAME/KEY: misc_feature
<222> LOCATION: (9)..(9)
<223> OTHER INFORMATION: n stands for any of the nucleotides A, G, C or
    T
<220> FEATURE:
<221> NAME/KEY: misc_feature
<222> LOCATION: (10)..(10)
<223> OTHER INFORMATION: n stands for any of the nucleotides A, G, C or
    T
<220> FEATURE:
<221> NAME/KEY: misc_feature
<222> LOCATION: (11)..(11)
<223> OTHER INFORMATION: n stands for any of the nucleotides A, G, C or
    T

<400> SEQUENCE: 2
ggtctcnnnn n                                                              11

```
<210> SEQ ID NO 3
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T

<400> SEQUENCE: 3
gaagacnnnn nn                                                          12

<210> SEQ ID NO 4
<211> LENGTH: 14
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
```

```
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T

<400> SEQUENCE: 4
acctgcnnnn nnnn                                                          14

<210> SEQ ID NO 5
<211> LENGTH: 8
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T

<400> SEQUENCE: 5 gcagtgnn                                                                  8

<210> SEQ ID NO 6
<211> LENGTH: 8
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T

<400> SEQUENCE: 6 gcaatgnn                                                                  8

<210> SEQ ID NO 7
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
```

-continued

```
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T

<400> SEQUENCE: 7
gtatccnnnn nn                                                          12

<210> SEQ ID NO 8
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T

<400> SEQUENCE: 8
actgggnnnn n                                                           11

<210> SEQ ID NO 9
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
```

-continued

```
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T
<220> FEATURE:
<221> NAME/KEY: misc_feature
<222> LOCATION: (17)..(17)
<223> OTHER INFORMATION: n stands for any of the nucleotides A, G, C or
      T

<400> SEQUENCE: 9
ggcggannnn nnnnnnn                                                      17

<210> SEQ ID NO 10
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
```

-continued

```
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T

<400> SEQUENCE: 10
gaggagnnnn nnnnnn                                                   16

<210> SEQ ID NO 11
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
```

```
<220> FEATURE:
<221> NAME/KEY: misc_feature
<222> LOCATION: (15)..(15)
<223> OTHER INFORMATION: n stands for any of the nucleotides A, G, C or
      T

<400> SEQUENCE: 11
cacctgcnnn nnnnn                                                          15

<210> SEQ ID NO 12
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T
<220> FEATURE:
<221> NAME/KEY: misc_feature
<222> LOCATION: (17)..(17)
<223> OTHER INFORMATION: n stands for any of the nucleotides A, G, C or
      T

<400> SEQUENCE: 12
cagctcnnnn nnnnnnn                                                        17
```

```
<210> SEQ ID NO 13
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T

<400> SEQUENCE: 13
gctcttcnnn n                                                         11

<210> SEQ ID NO 14
<211> LENGTH: 10
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T

<400> SEQUENCE: 14 ctcttcnnnn                                                           10

<210> SEQ ID NO 15
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
```

```
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T

<400> SEQUENCE: 15
ggtctcnnnn n                                                           11

<210> SEQ ID NO 16
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T

<400> SEQUENCE: 16
cgtctcnnnn n                                                           11

<210> SEQ ID NO 17
<211> LENGTH: 14
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
```

```
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T

<400> SEQUENCE: 17
acctgcnnnn nnnn                                                        14

<210> SEQ ID NO 18
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T

<400> SEQUENCE: 18
gaagacnnnn nn                                                          12

<210> SEQ ID NO 19
<211> LENGTH: 8
<212> TYPE: DNA
<213> ORGANISM: Artificial
<220> FEATURE:
<223> OTHER INFORMATION: Synthetic
```

```
-continued

<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T

<400> SEQUENCE: 19 gcaatgnn                                                              8

<210> SEQ ID NO 20
<211> LENGTH: 8
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T

<400> SEQUENCE: 20 gcagtgnn                                                              8

<210> SEQ ID NO 21
<211> LENGTH: 11
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T

<400> SEQUENCE: 21
actgggnnnn n                                                         11

<210> SEQ ID NO 22
<211> LENGTH: 12
<212> TYPE: DNA
<213> ORGANISM: Artificial
```

```
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T

<400> SEQUENCE: 22
gtatccnnnn nn                                                           12

<210> SEQ ID NO 23
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
```

```
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T

<400> SEQUENCE: 23
gaggagnnnn nnnnnn                                                      16

<210> SEQ ID NO 24
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T
```

```
<220> FEATURE:
<221> NAME/KEY: misc_feature
<222> LOCATION: (17)..(17)
<223> OTHER INFORMATION: n stands for any of the nucleotides A, G, C or
      T

<400> SEQUENCE: 24
ggcggannnn nnnnnnn                                                      17

<210> SEQ ID NO 25
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n stands for any of the nucleotides A, G, C or
      T
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T
<220> FEATURE:
<221> NAME/KEY: misc_feature
<222> LOCATION: (16)..(16)
<223> OTHER INFORMATION: n stands for any of the nucleotides A, G, C or
      T
<220> FEATURE:
<221> NAME/KEY: misc_feature
<222> LOCATION: (17)..(17)
<223> OTHER INFORMATION: n stands for any of the nucleotides A, G, C or
      T

<400> SEQUENCE: 25
cagctcnnnn nnnnnnn                                                      17
```

```
<210> SEQ ID NO 26
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: n stands for any of the nucleotides A, G, C or
      T
<220> FEATURE:
<221> NAME/KEY: misc_feature
<222> LOCATION: (9)..(9)
<223> OTHER INFORMATION: n stands for any of the nucleotides A, G, C or
      T
<220> FEATURE:
<221> NAME/KEY: misc_feature
<222> LOCATION: (10)..(10)
<223> OTHER INFORMATION: n stands for any of the nucleotides A, G, C or
      T
<220> FEATURE:
<221> NAME/KEY: misc_feature
<222> LOCATION: (11)..(11)
<223> OTHER INFORMATION: n stands for any of the nucleotides A, G, C or
      T
<220> FEATURE:
<221> NAME/KEY: misc_feature
<222> LOCATION: (12)..(12)
<223> OTHER INFORMATION: n stands for any of the nucleotides A, G, C or
      T
<220> FEATURE:
<221> NAME/KEY: misc_feature
<222> LOCATION: (13)..(13)
<223> OTHER INFORMATION: n stands for any of the nucleotides A, G, C or
      T
<220> FEATURE:
<221> NAME/KEY: misc_feature
<222> LOCATION: (14)..(14)
<223> OTHER INFORMATION: n stands for any of the nucleotides A, G, C or
      T
<220> FEATURE:
<221> NAME/KEY: misc_feature
<222> LOCATION: (15)..(15)
<223> OTHER INFORMATION: n stands for any of the nucleotides A, G, C or
      T

<400> SEQUENCE: 26
cacctgcnnn nnnnn                                                          15

<210> SEQ ID NO 27
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: Sequence of Fig. 1.1

<400> SEQUENCE: 27
ctgaacggca agaagctttt gcgctcttcc gtt                                      33

<210> SEQ ID NO 28
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(27)
<223> OTHER INFORMATION: Sequence of Fig.1.5
```

-continued

```
<400> SEQUENCE: 28
aacggcaaga agcttttgcg ctcttcc                                              27
```